(12) United States Patent
Nichols et al.

(10) Patent No.: US 7,259,167 B2
(45) Date of Patent: Aug. 21, 2007

(54) ANTIMALARIAL AND ANTIPROLIFERATIVE PHARMACOPHORE MODELS, NOVEL TRYPTANTHRIN COMPOUNDS HAVING INCREASED SOLUBILITY, AND METHODS OF MAKING AND USING THEREOF

(75) Inventors: Daniel A. Nichols, Sparrows Point, MD (US); Rickey P. Hicks, Woodbridge, VA (US); Apurba K. Bhattacharjee, Silver Spring, MD (US)

(73) Assignee: United States of America as Represented by the Secretary of the Army, Washington, DC (US)

( * ) Notice: Subject to any disclaimer, the term of this patent is extended or adjusted under 35 U.S.C. 154(b) by 422 days.

(21) Appl. No.: 10/359,625

(22) Filed: Feb. 7, 2003

(65) Prior Publication Data

US 2004/0033934 A1 Feb. 19, 2004

Related U.S. Application Data

(60) Provisional application No. 60/396,911, filed on Jul. 17, 2002, provisional application No. 60/355,162, filed on Feb. 9, 2002.

(51) Int. Cl.
*A61K 31/535* (2006.01)
*A01N 43/58* (2006.01)
*A01N 43/60* (2006.01)
*C07D 471/04* (2006.01)
*C07D 471/22* (2006.01)

(52) U.S. Cl. ............... 514/257; 514/256; 514/250; 514/229.5

(58) Field of Classification Search ............ 514/256, 514/257, 250, 229.5
See application file for complete search history.

(56) References Cited

U.S. PATENT DOCUMENTS

| 4,522,811 A | 6/1985 | Eppstein et al. |
| 5,441,955 A | 8/1995 | Baker et al. |
| 6,284,772 B1 | 9/2001 | Pitzer et al. |
| 6,531,487 B2 | 3/2003 | Pitzer et al. |

OTHER PUBLICATIONS

Peter I. Trigg, et al., "The Current Global Malaria Situation", Malaria Parasite Biology, Pathogenesis and Protection, Ed. I.W. Sherman, ASM Press, Washington, DC, Chapter 2, pp. 11-22 (1998).
N.J. White, "Drug Resistance in Malaria", Br. Med. Bull. 54 (No. 3): 703-715 (1998).
Jeffrey A. Vroman, et al., "Current Progress in the Chemistry, Medicinal Chemistry and Drug Design of Artemisinin Based Antimalarials", Curr. Pharm. Design, 1999, 5, 101-138.
Apurba K. Bhattacharjee, et al., "Stereolectronic Properties of Antimalarial Artemisinin Analogues in Relatino to Neurotoxicity", Chem. Res. Toxicol. vol. 12, No. 5, pp. 422-428 (1999).
Shoji Eguchi, et al., "Short-Step Synthesis of Rutecarpine and Tryptanthrin Via Intramolecular AZA-Wittig Reaction", Heterocycles vol. 33, No. 1, pp. 153-156 (1992).
G. Honda, et al., "Isolation of Antifungal Principle Tryptanthrin, from *Strobilanthes cusia*", J. Med. Plant Res., Planta Medica, vol. 36, p. 85-86 (1979).
Lester A. Mitscher, et al., "Antimicrobial Agents from Higher Plants. New Synthesis and Bioactivity of Tryptanthrin (Indolo-[2, 1-b]—Quinazolin-6, 12-Dione) and its Analogues", Heterocycles, vol. 15, No. 2, pp. 1017-1021 (1981).
C.W. Bird, "The Structure of Methylisatoid", Tetrahedron, vol. 19, pp. 901-904 (1963).
Steven R. Meshnick, "From Quinine to Qinghaosu: Historical Perspectives", Malaria Parasite Biology, Pathogenesis and Protection, Ed. I.W. Sherman, ASM Press, Washington, DC, pp. 341-353 (1998).
Apurba K. Bhattacharjee, et al., "Analysis of Stereoelectronic Properties, Mechanism of Action and Pharmacophore of Synthetic Indolo [2,1-b] quinazoline-6, 12-dione Derivatives in Relation to Antileishmanial Activity Using Quantum Chemical, Cyclic Voltammetry and 3-D-QSAR CATALYST Procedures", Bioorg. Med. Chem. 10: (2002) 1979-1989.
Ingo Muegge, et al., "Simple Selection Criteria for Drug-like Chemical Matter", J. Med. Chem. vol. 44, No. 12, pp. 1841-1846 (2001).
Jan Bergman, et al., "The Structure and Properties of Some Indolic Constituents in *Couroupita guianensis* Aubl." Tetrahedron vol. 41, No. 14, pp. 2879-2881 (1985).
R. Kikumoto, et al., "The Reactions of Oxindoles and Isatin With Nitrobenzyl Chlorides", Tetrahedron vol. 22, pp. 3337-3343 (1966).
Paul G. Gassman, et al., "A General Method for the Synthesis of Isatins", J. Org. Chem., vol. 42, No. 8, pp. 1344-1348 (1977).
C.S. Marvel, et al., "Organic Syntheses", 2d. Blatt Ed. New York, pp. 327-330 (1941).
Frank D. Popp "The Chemistry of Isatin", Adv. Het. Chem. 18:1, pp. 1-59, (1975).
Harman S. Lowrie "3-Phenylcinnolines. I. Some Reactions and Derivatives of 3-Phenylcinnoline-4-Carboxylic Acids", J. Med. Chem. 9:664 (1966).
Henry E. Baumgarten, et al., "Cinnolines. IX. The Stolle-Becker Synthesis", J. Org. Chem., vol. 26, pp. 1536-1539 (1961).
Gary M. Coppola, "The Chemistry of Isatoic Anhydride", Synthesis, pp. 505-536 (1980).
Apurba K. Bhattacharjee, et al., "A 3D QSAR Pharmacophore Model and Quantum Chemical Structure-Activity Analysis of Chloroquine (CQ)-Resistance Reversal", J. Chem. Info. Comput. Sci., 42:1212-1220 (2002).

(Continued)

*Primary Examiner*—San-ming Hui
(74) *Attorney, Agent, or Firm*—Elizabeth Arwine

(57) ABSTRACT

Disclosed herein is a pharmacophore model for antimalarial activity and methods of making and using thereof. The pharmacophore comprises two hydrogen bond acceptor (lipid) functions and two hydrophobic (aromatic) functions. The pharmacophore model was made using a test set of tryptanthrin compounds which exhibit antimalarial activity. Also disclosed are tryptanthrin compounds having greater solubility and bioactivity as compared to prior art tryptanthrin compounds and methods of making and using thereof. Also disclosed are methods of treating malaria in a subject.

7 Claims, 18 Drawing Sheets

OTHER PUBLICATIONS

Apurba K. Bhattacharjee, et al., "Molecular Electronic Properties of a Series of 4-Quinolinecarbinolamines Define Antimalarial Activity Profile", J. Med. Chem. (1996) 39, pp. 4622-4629.

MIchael A. Riel, et al., "Efficacy of Proton Pump Inhibitor Drugs Against Plasmodium Falciparum In Vitro and Their Probable Pharmacophores" Antimicrob. Agents Chemother., vol. 46, No. 8, pp. 2627-2632.

M. Grigorov, et al., "A QSAR Study of the Antimalarial Activity of Some Synthetic 1,2,4-Trioxanes", J. Chem. Inf. Comput. Sci. vol. 37, pp. 124-130 (1997).

P.A. Greenridge, et al., "A Comparison of Methods for Pharmacophore Generation with the Catalyst Software and their Use for 3D-QSAR: Application to a Set of 4-Aminopyridine Thrombin Inhibitors", Mini Reviews in Medicinal Chemistry (2001) vol. 1, pp. 79-87.

Jonathan Greene, et al., "Chemical Function Queries for 3D Database Search", J. Chem. Inf. & Comp. Sci. vol. 34, pp. 1297-1308.

Yasuhisa Kurogi, et al., "Pharmacophore Modeling and Three-dimensional Database Searching for Drug Design Using Catalyst", Current Medicinal Chemistry, vol. 8, pp. 1035-1055, (2001).

A.F. Slater, et al., "Inhibition by chloroquine of a novel haem polymerase enzyme activity in malaria trophozoites", Nature, vol. 355, pp. 167-169 (1992).

Serge Moreau, et al., "A nuclear magnetic resonance study of the interactions of antimalarial drugs with prophyrins", Biochemical et. Biophysica Acta 840 (1985) pp. 107-116.

Steve L. Alam, et al., "Detailed NMR analysis of the heme-protein interactions in component IV Glycera dibranchiata monomeric hemoglobin-CO", J. Biomol. NMR vol. 11, pp. 119-133 (1998).

Charalampos G. Kalodimos, et al., "Multinuclear ($^{13}$C, $^{17}$O, $^{57}$Fe) NMR studies of carbonmonoxy heme proteins and synthetic model compounds" J. Inorg. Biochem. vol. 79, pp. 371-380 (2000).

Peter B. Crowley, et al., "Hydrophobic Interactions in a Cyanobacterial Plastocyanin—Cytochrome f Complex", J. Am. Chem. Soc. vol. 123, pp. 10444-10453 (2001).

J. Hill, "The activity of some antibiotics and long-acting compounds against the tissue stages of *Plasmodium berghei*", Ann. Trop. Med. Parasitol. vol. 69, pp. 421-427 (1975).

G. Honda, et al., "The Antimicrobial Specificity of Tryptanthrin", Planta Med. vol. 37, No. 2, pp. 172-174 (1979).

G. Honda, et al., "Isolation of an Antidermatophytic, Tryptanthrin from Indigo Plants, *Polygonum tinctorium* and *Isatis tinctoria*", Planta Med. vol. 38, No. 3, pp. 275-276 (1980).

K. Seifert, et al., "Insecticidal and Fungicidal Compounds from *Isatis tinctoria*", Z Naturforsch vol. 49 (1-2) pp. 44-48 (1994).

Tomoo Hosoe, et al., "Isolation of a new potent cytotoxic pigment along with indigotin from the pathogenic basidiomycetous fungus *Schizophyllum commune*", Mycopathlogia vol. 146 (1), pp. 9-12 (1999).

Tetsuo Kimoto, et al., "Cytotix effects of Substances in Indigo Plant (*Polygonum tinctorium* Lour) on malignant tumor cells", Natural Medicines vol. 53 (2), pp. 72-79 (1999).

Yonghong L., et al., "Studies on in vitro Anticancer Activity of Tryptanthrin B", Chinese Traditional and Herbal Drugs, vol. 31 (7), pp. 531-545 (2000).

Satomi Koya-Miyata, et al., "Prevention of Azoxymethane-induced Intestinal Tumors by a crude Ethyl Acetate-extract and Tryptanthrin Extracted from *Polygonum tinctorium* Lour", Anticancer Research vol. 21 (5) pp. 3295-3300 (2001).

Tetsuo Kimoto, et al., "Cell differentiation and apoptosis of monocytic and promyelocytic leukemia cells (U-937 and HL-60) by tryptanthrin, an active ingredient of *Polygonum tinctorium* Lour", Pathol. Int. vol. 51 (5), pp. 315-325 (2001).

Mari Kataoka, et al., "Antibacterial action of tryptanthrin and kaempferol, isolated from the indigo plant (*Polygonum tinctorium* Lour.) against Helicobacter pylori-infected Mongolian gerbils", J. Gastroenterology, vol. 36, pp. 5-9 (2001).

Mark J. Micallef, et al., "The natural plant product tryptanthrin ameliorates dextran sodium sulfate-induced colitis in mice", Int. Immunopharmacol 2 (4), pp. 565-578 (treatment of colitis) (2002).

John Scovill, et al, "Antitrypanosomal Activities of Tryptanthrins", Antimicrob. Agents Chemother. 46(3), pp. 882-883 (antitrypanosomal activity) (2002).

Robert E. Desjardins, et al, "Quantitative Assessment of Antimalarial Activity in Vitro by a Semiautomated Microdilution Technique", Antimicrob. Agents Chemther vol. 16, pp. 710-718 (1979).

J.D. Chulay, et al, "Plasmodium falciparum: Assessment of in Vitro Growth by [$^3$H] Hypoxanthine Incorporation", Exp. Parasitol., vol. 55, pp. 138-146 (1983).

A.K. Bhattacharjee, "Electrostatic potential profiles may guide cation-pi interaction in antimalarials chloroquine and mefloquine: an ab initio quantum chemical study", Bioorg. Med. Chem. vol. 10, pp. 1979-1989 (2002).

Jingtao Wang, et al., "Solution NMR Determination of the Seating(s) of Meso-nitro-etioheme-1 in Myoglobin: Implications for Steric Constraints to Meso Position Access in Heme Degradation by Coupled Oxidation", J. Am. Chem. Soc., vol. 123, pp. 8080-8088 (2001).

Sandro Mecozzi, "Cation-ηinteractions in Simple Aromatics: electrostatics Provide a predictive Tool", J. Am. Chem. Soc., vol. 118, pp. 2307-2308 (1996).

Michael J.S. Dewar, et al., "AM1: A New General Purpose Quantum Mechanical Molecular Model", J. am. Chem. Soc., vol. 107, pp. 3902-3909 (1985).

Malcolm R. Smyth, et al., "Analytical Voltammetry", Elsevier: New York (1992): Chapter 1.

Lisa A. Collins, et al., "Microplate Alamar Blue Assay versus BACTEC 460 System for High-Throughput Screrening of Compounds against *Mycobacterium tuberculosis* and *Mycobacterium avium*", Antimicrob. Agents Chemother, vol. 41, pp. 1004-1009 (1997).

Michael C. Alley, et al., "Feasibility of Drug Screening with Panels of Human Tumor Cell Lines Using a Microculture Tetrazolium Assay", Cancer Research, vol. 48, pp. 589-601 (1988).

Michael R. Grever, et al., "The National Cancer Institute: Cancer Drug Discovery and Development Program", Seminars in Oncology 19(6), pp. 622-638 (1992).

Michael R. Boyd, et al., "Some Practical Considerations and Applications of the National Cancer Institute in Vitro Anticancer Drug Discovery Screen", Drug Development Research, vol. 34, pp. 91-109 (1995).

Melinda G. Hollingshead, et al., "In Vivo Cultivation of Tumor Cells in Hollow Fibers", Life Sciences, vol. 57, No. 2, pp. 131-141 (1995).

Notification of Transmittal of the International Search Report or the Declaration (Form PCT/ISA/220) issued for PCT/US03/03517.

International Search Report (Form PCT/ISA/210) issued for PCT/US03/03517.

Plot of Max proton Dd vs. Hemin concentration

ANTIMALARIAL AND ANTIPROLIFERATIVE PHARMACOPHORE MODELS, NOVEL TRYPTANTHRIN COMPOUNDS HAVING INCREASED SOLUBILITY, AND METHODS OF MAKING AND USING THEREOF

CROSS REFERENCE TO RELATED APPLICATIONS

This application claims the benefit of U.S. Provisional Patent Application Nos. 60/355,162 filed Feb. 9, 2002, and No. 60/396,911, filed Jul. 17, 2002, which name Daniel A. Nichols, Rickey P. Hicks, and Apurba K. Bhattacharjee as joint inventors and are herein incorporated by reference in its entirety.

ACKNOWLEDGMENT OF GOVERNMENT SUPPORT

This invention was made by employees of the United States Army. The government has rights in the invention.

BACKGROUND OF THE INVENTION

1. Field of the Invention

The present invention generally relates to a pharmacophore for antimalarial activity. In particular, the present invention relates to a pharmacophore derived from tryptanthrin compounds and how to increase the solubility and bioavailability of the compounds.

2. Description of the Related Art

The current global situation with respect to malaria indicates that about two billion people are exposed to the disease and of these 400 million people are already infected. See Trigg, P. I., and A. V. Kondrachine (1998) The Current Global Malaria Situation, Chapter 2, p. 11-22, in MALARIA PARASITE BIOLOGY, PATHOGENESIS AND PROTECTION. Ed. I. W. Sherman, ASM Press, Washington, D.C. Each year between 100 to 200 million new cases of infection are reported and approximately 1 to 2 million people die due to malaria. The situation is rapidly worsening mainly due to non-availability of effective drugs and development of drug resistance of a large number of non-immune people in areas where malaria is frequently transmitted. See White, N. J. (1998) Br. Med. Bull. 54:703-715.

In an increasingly wide geographic area, both *Plasmodium falciparum* and *Plasmodium vivax* have been developing resistance to chloroquine, the most successful antimalarial drug in the past several decades. Mefloquine and doxycycline, the two other frontline drugs for the treatment and prevention of malaria are becoming increasingly ineffective. See Vroman, J. A. et al. (1999) Curr. Pharm. Design 5:101-138. Artemisinin analogs such as artesunate and arteether were later introduced that are found to be quite effective, particularly against drug-resistant *P. falciparum* but observations of drug-induced and dose-related neurotoxicity in animals have raised concern about the safety of these compounds for human use. See Bhattacharjee, A. K. and J. M. Karle (1999) Chem. Res. Toxicol. 12: 422-428. Therefore, much effort and attention are needed for the discovery and development of new and less toxic antimalarial drugs.

SUMMARY OF THE INVENTION

The present invention generally relates to a pharmacophore model for antiproliferative, antibacterial, antifungal, or antiprotozoal activity. In preferred embodiments, the pharmacophore of the present invention is a pharmacophore model for antimalarial activity.

In some embodiments, the present invention relates to a pharmacophore for antiproliferative, antibacterial, antifungal, or antiprotozoal activity of a compound comprising two hydrogen bond acceptor (lipid) functions and two hydrophobic (aromatic) functions.

In some embodiments, the pharmacophore of the present invention is made by (a) generating a set of three-dimensional conformers for each of the compounds in a training set comprising at least five compounds known to exhibit an activity, (b) correlating each of the compounds of the training set with at least one observed $IC_{50}$ value of the activity, (c) generating from the set of three-dimensional conformers at least one hypothesis, (d) calculating the activity for each conformer of step (a) towards the hypothesis, (e) calculating the total cost for the hypothesis, and (f) selecting the hypothesis with the lowest cost as the pharmacophore. In some preferred embodiments, the activity is antiproliferative, antibacterial, antifungal, or antiprotozoal activity, preferably antimalarial activity. In some preferred embodiments, at least one of the compounds known to exhibit the activity is a tryptanthrin compound. In some embodiments, the steps are carried out using a molecular modeling software program such as CATALYST®. In some preferred embodiments, the observed $IC_{50}$ value of antimalarial activity ranges from about 0.4 ng/ml to about 50,000 ng/ml. In some preferred embodiments, the energy range of the set of three-dimensional conformers is about 0 to about 25 Kcal/mole.

In some preferred embodiments, the pharmacophore of the present invention comprises the following X, Y, and Z coordinates of the hydrogen bond acceptor (lipid) functions and the hydrophobic (aromatic) functions:

| Coordinates | HBA lipid | | HBA lipid | | | |
|---|---|---|---|---|---|---|
| | First Focal Point | Second Focal Point | First Focal Point | Second Focal Point | Hydrophobic | Hydrophobic |
| X | 1.59 | 1.76 | −1.05 | −1.83 | 5.89 | −4.69 |
| Y | 2.40 | 4.83 | 0.51 | 3.29 | 0.40 | −1.17 |
| Z | −2.04 | −3.83 | −2.00 | −2.80 | 0.82 | −1.07 |

In some embodiments, the pharmacophore of the present invention comprises a root mean square equivalent functions of less than about 3.0 Å of the hydrogen bond acceptor (lipid) functions and the hydrophobic (aromatic) functions of the following X, Y, and Z coordinates of the hydrogen bond acceptor (lipid) functions and the hydrophobic (aromatic) functions:

| Coordinates | HBA lipid | | HBA lipid | | | |
| --- | --- | --- | --- | --- | --- | --- |
| | First Focal Point | Second Focal Point | First Focal Point | Second Focal Point | Hydrophobic | Hydrophobic |
| X | 1.59 | 1.76 | −1.05 | −1.83 | 5.89 | −4.69 |
| Y | 2.40 | 4.83 | 0.51 | 3.29 | 0.40 | −1.17 |
| Z | −2.04 | −3.83 | −2.00 | −2.80 | 0.82 | −1.07 |

In preferred embodiments, the root mean square is less than about 1.5 Å, preferably less than about 1.0 Å, more preferably, less than about 0.5 Å.

In some embodiments, the present invention provides a method for screening a candidate compound for antiproliferative, antibacterial, antifungal, or antiprotozoal activity which comprises (a) finding the best fit of the candidate compound to the pharmacophore of the present invention, and (b) calculating the activity value for the candidate compound. In some preferred embodiments, the best fit is determined using a fast-fit algorithm, a principle component analysis, a partial least squares technique, a linear regression technique, or a non-linear regression technique. In some preferred embodiments, the compound exhibits antimalarial activity.

In some embodiments, the present invention provides a compound having antiproliferative, antibacterial, antifungal, or antiprotozoal activity identified by the method of screening candidate compounds according to the present invention. In some embodiments, the present invention provides a pharmaceutical composition comprising a compound having antiproliferative, antibacterial, antifungal, or antiprotozoal activity identified by the method of screening candidate compounds according to the present invention and a pharmaceutically acceptable carrier. In some preferred embodiments, the compound exhibits antimalarial activity.

In some embodiments, the present invention provides a method of treating, preventing, or inhibiting malaria in a subject which comprises administering to the subject a therapeutically effective amount of the compound of identified by the method of screening candidate compounds for antimalarial activity according to the present invention or a pharmaceutical composition comprising a therapeutically effective amount of a compound of identified by the method of screening candidate compounds for antimalarial activity and a pharmaceutically acceptable carrier.

In some embodiments, the present invention provides a method of treating, preventing, or inhibiting malaria in a subject which comprises inhibiting or modulating the haem polymerase of the *Plasmodium falciparum* organisms present in the subject.

In some embodiments, the present invention provides a method of optimizing hemin binding affinity of a tryptanthrin compound which comprises changing or modulating the substituent on the 8-position of the tryptanthrin compound.

In some embodiments, the present invention provides a method of treating, preventing, or inhibiting malaria in a subject which comprises administering to the subject a therapeutically effective amount of at least one aminoquinazoline compound having the following structural formula A:

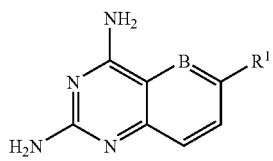

(A)

wherein B is C or N;
R$^1$ is S—R$^2$ or

wherein R$^2$ is a substituted or unsubstituted cycloalkyl group, a substituted or unsubstituted heterocycloalkyl group, a substituted or unsubstituted aryl group or a substituted or unsubstituted heteroaryl group. In some preferred embodiments, the compound is 2,4-diamino-6-(naphthalen-1-ylsulfanyl)pyrido(3,2-d)pyrimidine; 2,4-diamino-6-(3,4-dichlorophenylsulfonyl)quinazoline; 2,4-diamino-6-(4-bromo-3-methylphenylsulfonyl)quinazoline; 2,4-diamino-6-(3-methoxyphenylsulfonyl)quinazoline; or 2,4-diamino-6-(naphthalen-2-ylsulfonyl)quinazoline.

In some embodiments, the present invention provides a method of determining the antimalarial activity or potency of a candidate compound which comprises (a) generating three-dimensional descriptors for the candidate compound, (b) inputting the three-dimensional descriptors into an equation relating to the observed antimalarial activity of a set of antimalarial compounds to a set of three-dimensional descriptors for the set of antimalarial compounds, and (c) solving the equation for the antimalarial activity or potency of the candidate compound corresponding to the three-dimensional descriptors of step (a).

In some embodiments, the present invention provides a method of increasing the solubility, bioavailability, or both of a tryptanthrin compound which comprises dissolving the tryptanthrin compound in a solvent having at least one N—H, OH, or (hetero)aromatic function, adding the solution to an aqueous solution, and removing the solvent by evaporation. In some preferred embodiments, the solvent is pyrrole, indole, pyridine, isoquinoline, nitrobenzene, aniline, N-methylbenzylamine, piperidine, pyrrolidine, phenol, benzyly alcohol, benzoic acid, or 1,4-dioxane. In some preferred embodiments, the aqueous solution is deionized water. In some preferred embodiments, the tryptanthrin compound has the following structural formula (II)

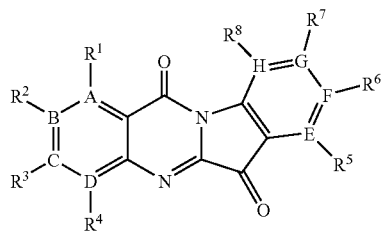

(II)

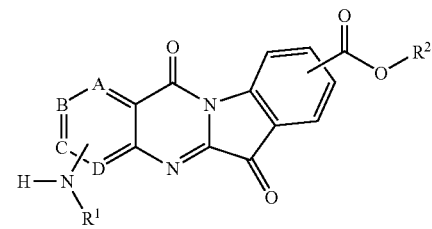

(IV)

wherein A, B, C, D, E, F, G and H are each independently selected from carbon and nitrogen, or A and B or C and D can be taken together to be nitrogen or sulfur, with the proviso that not more than three of A, B, C, D, E, F, G and H are other than carbon; wherein $R^1$ through $R^8$ are each independently selected from the group consisting of, but not limited to, the halogens (F, Cl, Br, and I), alkyl groups, trifluoromethyl groups, methoxyl groups, the carboxy methyl or carboxy ethyl group ($COOCH_3$ or $COOCH_2CH_3$), nitro, aryl, heteroaryl, cyano, amino, dialkylaminoalkyl, 1-(4-alkylpiperazinyl), and the pharmaceutically acceptable salts thereof.

In some embodiments, the present invention provides a method of treating, preventing, or inhibiting a disease or disorder associated with cell proliferation, bacterial infection, fungal infection, or protozoal infection, antifungal, or antiprotozoal in a subject which comprises administering to the subject a therapeutically effective amount of at least one tryptanthrin compound made by the method of increasing the solubility or bioavailability according to the present invention, or a pharmaceutical composition comprising at least one tryptanthrin compound made by the method of increasing the solubility or bioavailability according to the present invention. In some preferred embodiments, the disease or disorder related to cell proliferation is cancer, papillomas, acute or chronic inflammation, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, inflammatory bowel disease, or silicosis. In some preferred embodiments, the cancer is leukemia, CNS cancer, renal cancer, non-small cell lung cancer, melanoma, prostate cancer, colon cancer, ovarian cancer, or breast cancer. In some preferred embodiments, the bacterial infection is *Streptococcal, Staphylococcal*, bacterial meningitis, *Yersinia pestis, Enterobacter, Helicobacter, Bacillus anthracis, Escherichia coli, Mycobacterium*, preferably *Mycobacterium tuberculosis*. In some preferred embodiments, the fungal infection is histoplasmosis, coccidioidomycosis, blastomycosis, paracoccidioidomycosis, sporotrichosis, cryptococcosis, candidiasis, aspergillosis, or mucormycosis. In some preferred embodiments, the protozoal infection is malaria, leishmaniasis, or trypanosomiasis.

In some embodiments, the present invention provides a tryptanthrin compound having the following structural formula (IV)

wherein A, B, C, and D are each independently selected from the group consisting of C, N, and S;

$R^1$ and $R^2$ are each independently selected from the group consisting of polypeptides, polyamines, polyethers or -L-$R^3$ wherein L is a linker and $R^3$ is substituted or unsubstituted

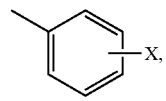

substituted or unsubstituted

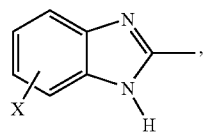

substituted or unsubstituted

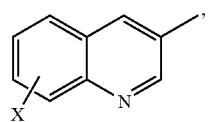

wherein X is one or more substituents selected from the group consisting of alkyl, hydroxyl, alkoxy, acyl, amino, alkylamino, dialkylamino, alkoxycarbonyl, carboxyl, carbamoyl, alkylaminocarboxyl, dialkylaminocarboxyl, alkylthio or mercapto and the linker comprises about 2 to about 18 carbon, nitrogen, oxygen or sulfur atoms in its chain selected from the group consisting of alkyl, alkylamino, dialkylamino, alkoxyl, alkoxycarbonyl, alkylaminocarbonyl, dialkylaminocarbonyl, alkylthio, and carbamoyl groups.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein:

FIG. 12 shows the electron density maps of selected compounds at approximately 1.40-1.45 angstrom (-1 Kcal/mol) away from the van der Waal's surface.

FIGS. 13A and 13B show the first redox potential.

FIGS. 13C and 13D show the second redox potential.

FIGS. 13E and 13F show the lowest unoccupied molecular orbital (LUMO) energy.

FIGS. 13A, 13C, and 13E show the C6 carbonyl.

FIGS. 13B, 13D, and 13F show the C12 carbonyl.

DETAILED DESCRIPTION OF THE INVENTION

Figure 1:
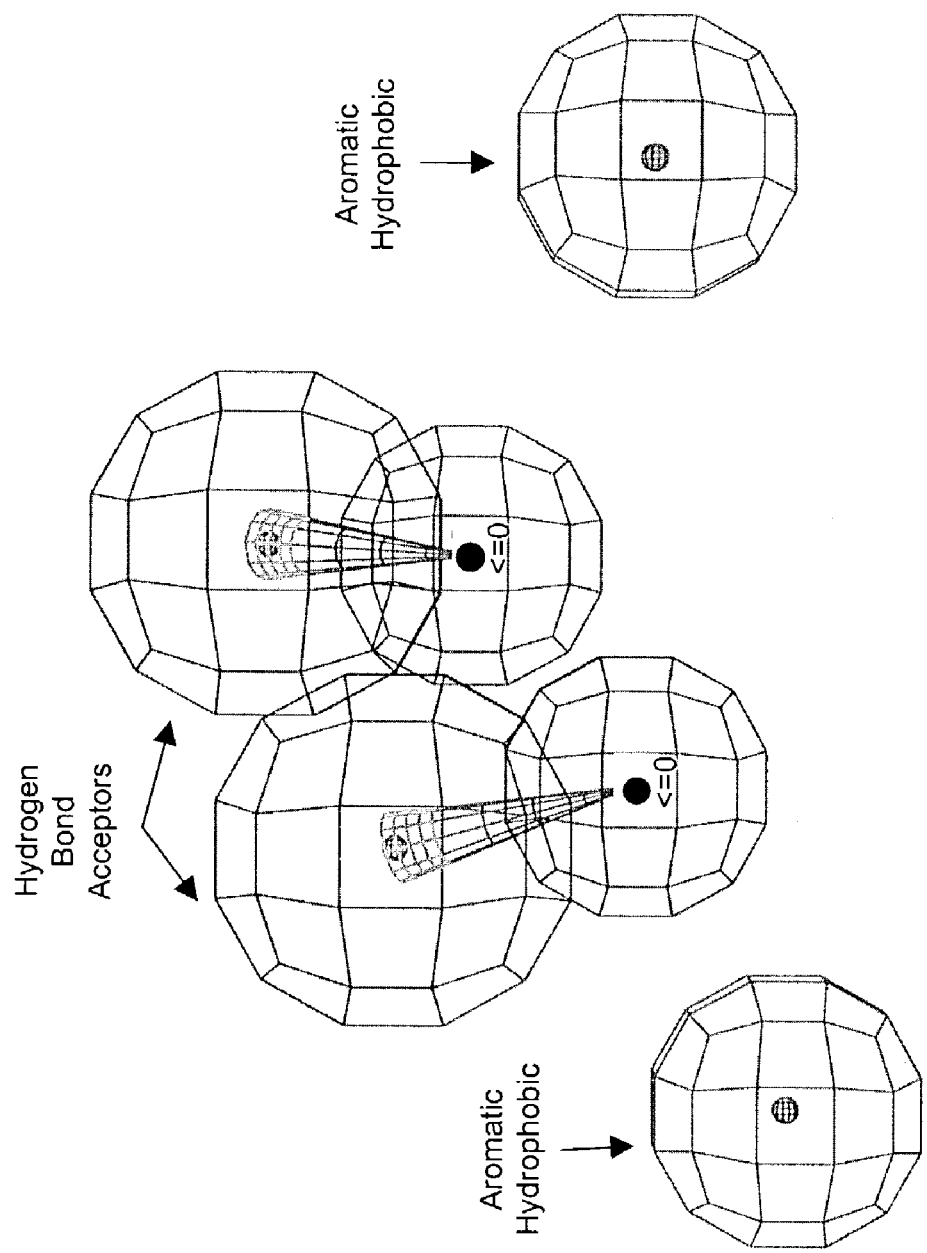
FIG. 1 represents the pharmacophore model of the present invention that is characterized by two hydrogen bond acceptor (lipid) functions and two hydrophobic (aromatic) functions.

Tryptanthrin (indolo(2,1-b)quinazoline-6,12-dione) is an alkaloid isolated from the Taiwanese medicinal plant, *Strobilanthes cusia*. See U.S. Pat. No. 5,441,955; Eguchi, S., et al. (1992) Heterocycle 33:153-156; Honda, G., and M. Tabata (1979) J. Med. Plant Res., Planta Medica, 36:85-86; Mitscher, L. A., et al. (1981) Heterocycle 15:1017-1021.

Tryptanthrin has the following structural formula (I):

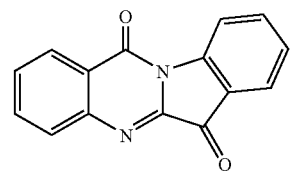

(I)

Tryptanthrins have a long history and are known to possess activity against a variety of pathogenic bacteria, particularly the causative agent of tuberculosis. See Bird, C. W. (1963) Tetrahedron 19:901-904; Eguchi, S., et al. Heterocycles 33:153-156; Honda, G., and M. Tabata (1979) J. Med. Plant Res., Planta Medica 36:85-86; Meshnick, S. R. (1998) MALARIA PARASITE BIOLOGY, PATHOGENESIS AND PROTECTION. ed. I. W. Sherman, ASM Press, Washington, D.C., pp. 341-353; and Mitscher, L. A., et al. (1981) Heterocycles 15:1017-1021. The parent compound, indolo(2,1-b)quinazoline-6,12-dione, can also be produced by *Candida lipolytica* when grown in media containing an excess of tryptophan, which is why the compound is also called tryptanthrin.

As used herein, "tryptanthrin compounds" are those compounds that have the structural formula I as a core structure. The tryptanthrin compounds used herein were obtained from PathoGenesis Corporation (Seattle, Wash., now owned by Chiron, Emeryville, Calif.) tryptanthrin compounds may be synthesized or obtained by methods known in the art. See U.S. Pat. Nos. 5,441,955 and 6,284,772, which are herein incorporated by reference.

For example, tryptanthrin compounds may be extracted from a number of plants across the world, which include *Isatis tinctoria, Polygonum tinctorium*, and *Wrighta tinctoria*. Alternatively, tryptanthrin compounds may be synthesized by base-catalyzed condensation of substituted isatins and substituted isatoic anhydrides through a convenient one-step flexible synthesis as previously reported. See U.S. Pat. No. 5,441,955; and Bhattacharjee, A. K., et al. (2002) Bioorg. Med. Chem. 10: 1979-1989, which are herein incorporated by reference. Additionally, a number of other synthetic routes for making tryptanthrin compounds that are known in the art may be used. See e.g. Muegge, I., et al.

(2001) J. Med. Chem. 44:1841; Bergman, J., et al. (1985) Tetrahedron 41:2879; Mitscher, L. A., et al. (1981) Heterocycles 15:1017; Eguchi, S. et al. (1992) Heterocycles 33:153; and Kikumoto, R. (1966) Tetrahedron 22:3337, which are herein incorporated by reference.

Typically, tryptanthrin compounds are constructed from derivatives of isatoic anhydride (a) and isatins (b) having the following general structural formulas:

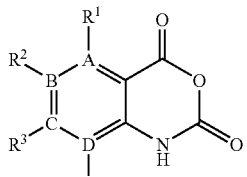

(a)

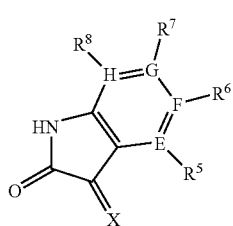

(b)

to give tryptanthrin (I) and derivatives thereof (II) having the following general structural formulas:

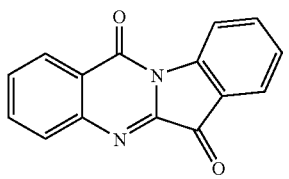

(I)

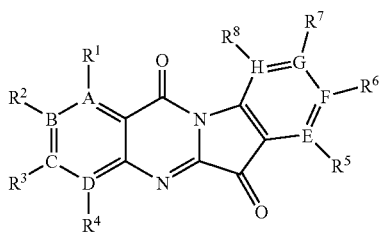

(II)

wherein A, B, C, D, E, F, G and H are each independently selected from carbon and nitrogen, or A and B or C and D can be taken together to be nitrogen or sulfur, with the proviso that not more than three of A, B, C, D, E, F, G and H are other than carbon; wherein $R^1$ through $R^8$ are each independently selected from the group consisting of, but not limited to, the halogens (F, Cl, Br, and I), alkyl groups, trifluoromethyl groups, methoxyl groups, the carboxy methyl or carboxy ethyl group ($COOCH_3$ or $COOCH_2CH_3$), nitro, aryl, heteroaryl, cyano, amino, dialkylaminoalkyl, 1-(4-alkylpiperazinyl), and the pharmaceutically acceptable salts and prodrugs thereof.

Isatins may be commercially obtained or made by methods known in the art. See e.g. Gassman, P. G., et al. (1977) J. Org. Chem. 42:1344; Marvel, C. S. and Hiers, G. S. (1941) Organic Syntheses, 2d. Blatt ed. New York, pp 327-330; Popp, F. D. (1975) Adv. Het. Chem. 18:1; Lowrie, H. S. (1966) J. Med. Chem. 9:664; and Baumgarten, H. E. and Furnas, J. L. (1961) J. Org. Chem. 26:1536, which are herein incorporated by reference. Likewise, isatoic anhydrides may be commercially obtained or made by methods known in the art. See e.g. Coppola, G. M. (1980) Synthesis 505, which is herein incorporated by reference.

A set of tryptanthrin compounds was screened for antimalarial activity according to Example 1. The tryptanthrin compounds displayed remarkable in vitro antimalarial activity against sensitive and multidrug-resistant strains of P. falciparum. See U.S. Pat. No. 6,284,772, which is herein incorporated by reference. The more potent tryptanthrin compounds exhibit $IC_{50}$ values in the range of about 0.43 to about 10 ng/ml. Furthermore, the tryptanthrin compounds are also found to be highly potent against strains of P. falciparum that are up to about 5000-fold resistant to atovoquone, about 50-fold resistant to chloroquine, and about 20-fold resistant to mefloquine. In other words, tryptanthrin compounds exhibit remarkable potent in vitro activity (below about 100 ng/ml) when tested against sensitive and multidrug-resistant malaria. Since tryptanthrin compounds are well tolerated in both macrophage and neuronal lines in in vitro toxicity studies, tryptanthrin compounds may be used for the chemotherapeutic treatment of malaria.

To further improve its in vitro efficacy, a series of additional tional azatryptanthrin compounds incorporating one to two nitrogen atoms in the A ring were synthesized and tested. Surprisingly, many of these tryptanthrin compounds showed high efficacy against P. falciparum and P. vivax. See U.S. Pat. No. 5,441,955; and U.S. Pat. No. 6,284,772, which are herein incorporated by reference.

To better understand the mechanism of action and to aid in the design and synthesis of new antimalarial therapeutic agents, the structure-activity relationships of tryptanthrin compounds were evaluated in order to develop a three-dimensional chemical feature based pharmacophore model for compounds that exhibit antimalarial activity. See Bhattacharjee, A. K., et al. (2002) A 3D QSAR Pharmacophore Model and Quantum Chemical Structure Activity Analysis of Chloroquine(CQ)-Resistance Reversal. J. Chem. Info. Comput. Sci. 42:1212-1220; Bhattacharjee, A. K., et al. (2002) Bioorg. Med. Chem. 10:1979-1989; Bhattacharjee, A. K., and J. M. Karle (1996) J. Med. Chem. 39: 4622-4629; and Riel, M. A. et al. (2002) Antimicrob. Agents Chemother. 46:2627-2632, which are herein incorporated by reference. Although CATALYST® 4.6 software (Accelrys Inc., San Diego, Calif.) was used for 3D QSAR analysis and pharmacophore generation, other methods known in the art such as those described in PHARMACOPHORE PERCEPTION, DEVELOPMENT, AND USE IN DRUG DESIGN (2000) Ed. Osman F. Gunner, International University Line, La Jolla, Calif., may be used according to the present invention.

As disclosed in Example 2, molecular modeling software, CATALYST® 4.6 software (Accelrys Inc., San Diego, Calif.) was used to construct a three-dimensional QSAR pharmacophore model for the antimalarial activities exhibited by tryptanthrin compounds. A training set of 17 structurally diverse indolo(2,1-b)quinazoline-6,12-dione compounds analogues having a broad range of antimalarial activities shown in Table 1 were used to construct the pharmacophore model. Although more or less compounds in the training set may be used, in preferred embodiments, about 15 to about 20 chemically diverse molecules with biological activity covering 4 to 5 orders of magnitude for the training set are used.

TABLE 1

(III)

| | R¹ | R² | R³ | R⁴ | R⁵ | R⁶ | R⁷ | R⁸ | R⁹ | R¹⁰ | X | Y | D |
|---|---|---|---|---|---|---|---|---|---|---|---|---|---|
| TRAINING SET | | | | | | | | | | | | | |
| 1 | CH | CH | CH | —N= | O | O | CH | C—Cl | CH | CH | C=R⁶ | C=R⁵ | C |
| 2 | CH | —N= | C—F | CH | O | O | CH | C—Cl | CH | CH | C=R⁶ | C=R⁵ | C |
| 3 | CH | CH | CH | CH | O | O | CH | C—CH₂CH₃ | CH | CH | C=R⁶ | C=R⁵ | C |
| 4 | CH | —N= | C—N<(CH₂)₄>N—CH₃ | —N= | O | O | CH | C—CHC₇H₁₆ | CH | CH | C=R⁶ | C=R⁵ | C |
| 5 | CH | —N= | C—CH₃ | CH | O | O | CH | CH | CH | CH | C=R⁶ | C=R⁵ | C |
| 6 | —N= | CH | CH | CH | O | O | CH | CCHC₇H₁₆ | CH | CH | C=R⁶ | C=R⁵ | C |
| 7 | CH | CH | CH | —N= | O | O | CH | C—F | CH | CH | C=R⁶ | C=R⁵ | C |
| 8 | —N= | CH | C—F | C—OCH₃ | O | C-phenyl | CH | C—F | CH | CH | C=R⁶ | C=R⁵ | C |
| 9 | CH | CH | CH | CH | O | O | CH | CH | C—N<(CH₂)₄>N—CH₃ | CH | C=R⁶ | C=R⁵ | C |
| 10 | CH | CH | CH | CH | O | O | CH | CH | CH | CH | O | C=R⁵ | C |
| 11 | —N= | CH | CH | CH | O | O | CH | CH | C—Cl | CH | S | C=R⁵ | C |
| 12 | CH | CH | CH | —N= | O | indole | CH | CH | CH | CH | C=R⁶ | C=R⁵ | C |
| 13 | —N= | CH | C—F | CH | O | dioxane | CH | CH | CH | CH | C=R⁶ | C=R⁵ | C |
| 14 | —N= | C—OH | CH | C—OH | O | O | CH | C—I | CH | CH | C=R⁶ | C=R⁵ | C |
| 15 | CH | CH | CH | CH | O | O | CH | C—Br | CH | CH | C=R⁶ | C=R⁵ | C |
| 16 | CH | CH | CH | CH | O | O | CH | CH | CH | CH | C=R⁶ | C=R⁵ | C |
| 17 | CH | CH | CH | CH | O | O | CH | CH | CH | CH | C=R⁶ | C=R⁵ | C |
| TEST SET | | | | | | | | | | | | | |
| 1* | CH | —N= | CH | CH | O | O | CH | C—C₈H₁₇ | CH | CH | C=R⁶ | C=R⁵ | C |
| 2' | CH | CH | CH | —N= | O | O | CH | C—Cl | CH | CH | C=R⁶ | C=R⁵ | C |
| 3' | CH | CH | CH | CH | O | O | CH | CH | CH | CH | C=R⁶ | C=R⁵ | C |
| 4' | CH | —N= | C—S—C₂H₄OH | CH | O | O | CH | C—C₄H₉ | CH | CH | C=R⁶ | C=R⁵ | C |
| 5' | CH | —N= | CH | CH | O | O | CH | C₆H₅ | CH | CH | C=R⁶ | C=R⁵ | C |
| 6' | CH | CH | CH | C—OCH₃ | O | O | CH | CH | CH | CH | C=R⁶ | C=R⁵ | C |
| 7' | CH | CH | CH | —N= | O | O | C—Cl | CH | CH | CH | C=R⁶ | C=R⁵ | C |
| 8' | CH | —N= | CH | C—OCH₃ | O | O | CH | C—CHOCH₃C—(CH₃)₂ | CH | CH | C=R⁶ | C=R⁵ | C |
| 9' | CH | CH | CH | CH | O | O | CH | C—OCF₃ | CH | CH | C=R⁶ | C=R⁵ | C |
| 10' | CH | CH | CH | —N= | O | O | CH | C—I | CH | CH | C=R⁶ | C=R⁵ | C |
| 11' | CH | —N= | CH | C—OCH₃ | O | O | CH | C—Br | CH | CH | C=R⁶ | C=R⁵ | C |
| 12' | CH | CH | C-piperidine | CH | O | O | CH | C—Cl | CH | CH | C=R⁶ | C=R⁵ | C |
| 13' | CH | —N= | CNCH₃(CH₂)₂OH | CH | O | O | CH | CH | CH | CH | C=R⁶ | C=R⁵ | C |
| 14' | CH | CH | CH | CH | O | O | CH | CH | CH | CH | C=R⁶ | C=R⁵ | C |
| 15' | CH | C—CH₃ | CH | CH | O | O | CH | CH | CH | CH | C=R⁶ | C=R⁵ | C |

The antimalarial biological activity of the 17 tryptanthrin compounds in the training set covers a broad range of activity, from an $IC_{50}$ of 0.4 ng/ml to 50,000 ng/ml. Although two P. falciparum malaria parasite clones, designated as Sierra Leone (D6) and Indochina (W2) were used in the susceptibility testing as disclosed in Example 1, the $IC_{50}$ values obtained from the W2 clones were used as the activity parameter to develop the pharmacophore model as the D6 clone results closely paralleled the W2 clones. See U.S. Pat. No. 6,284,772, which is herein incorporated by reference.

The structures of the training set were either imported into or edited within CATALYST® by assembling the structural fragments and energy minimized to the closest local minimum using the CHARMM-like force field. Molecular flexibility was taken into account by considering each compound as an ensemble of conformers representing different accessible areas in a three dimensional space. The "best searching procedure" was applied to select representative conformers within about 20 kcal/mol above the calculated global minimum. See Grigorov, M., et al. (1995) J. Chem. Inf. Comput. Sci. 35:285-304, which is herein incorporated by reference.

Hypothesis generation was carried out with the training set of 17 tryptanthrin compounds by methods known in the art. See Greenridge, P. A. and J. Weiser (2001) Mini Reviews in Medicinal Chemistry 1:79-87; Grigorov, M., et al. (1995) J. Chem. Inf. Comput. Sci. 35:285-304; which are herein incorporated by reference.

FIG. 1 represents the statistically most relevant hypothesis which is characterized by two hydrogen bond acceptor (lipid) functions and two hydrophobic (aromatic) functions. See Greene et al. (1994) J. Chem. Inf. & Comp. Sci. 34:1297-1308, which is herein incorporated by reference. The coordinates of the pharmacophore model represented by FIG. 1 are set forth in angstroms in Table 2 and define the relative relationship between the features.

invention is intended to encompass any model, after optimal superposition of the models, comprising the identified features and having a root mean square of equivalent features of less than about 3.0 Å. More preferably, the pharmacophore model of the present invention encompasses any model comprising the features identified herein and having a root mean square of equivalent features of less than about 1.5 Å, even more preferably, less than about 1.0 Å, and most preferably less than about 0.5 Å.

As those of skill in the art will readily recognize, chemically different substructures can present certain identical three-dimensional space-filling features, and accordingly, the models of the present invention comprise features that may or may not correspond to actual functional groups in any given antimalarial or antiproliferative compound. Additionally, since compounds having different structural formulas may have the same or similar pharmacophore hypotheses, the compounds of the present invention are not limited to compounds having the structural formula (I), (II), or (III).

CATALYST software allows mapping of all functions generated in a pharmacophore to the more potent analogues and fewer or none in the less potent analogues of the training set through conformational energy and best-fit scoring calculations. The technique involves a 3D screening of all the conformations of the molecule by matching the pharmacophore features. See Kurogi, Y. and O. F. Gunner (2001) Current Medicinal Chemistry 8:1035-1055, which is herein incorporated by reference.

Figure 2A:
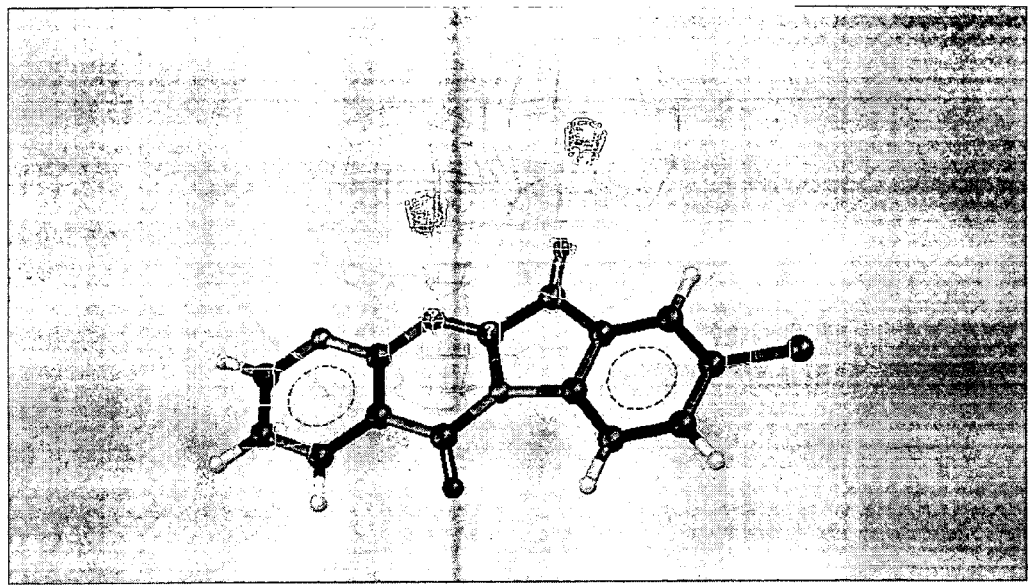
FIG. 2A shows compound 1 mapped to the pharmacophore model of the present invention.
Figure 2B:
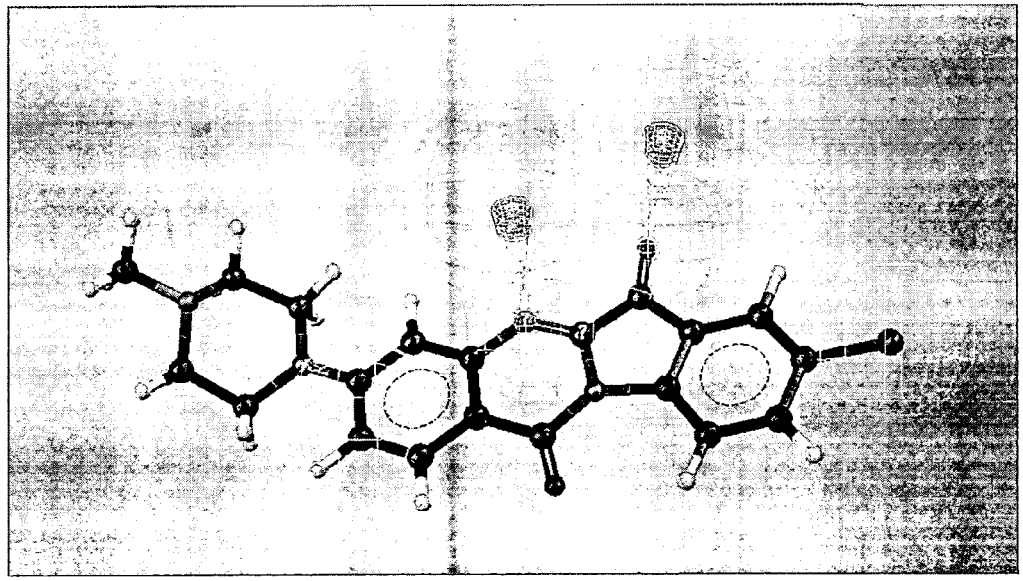
FIG. 2B shows compound 4 mapped to the pharmacophore model of the present invention.
Figure 2C:
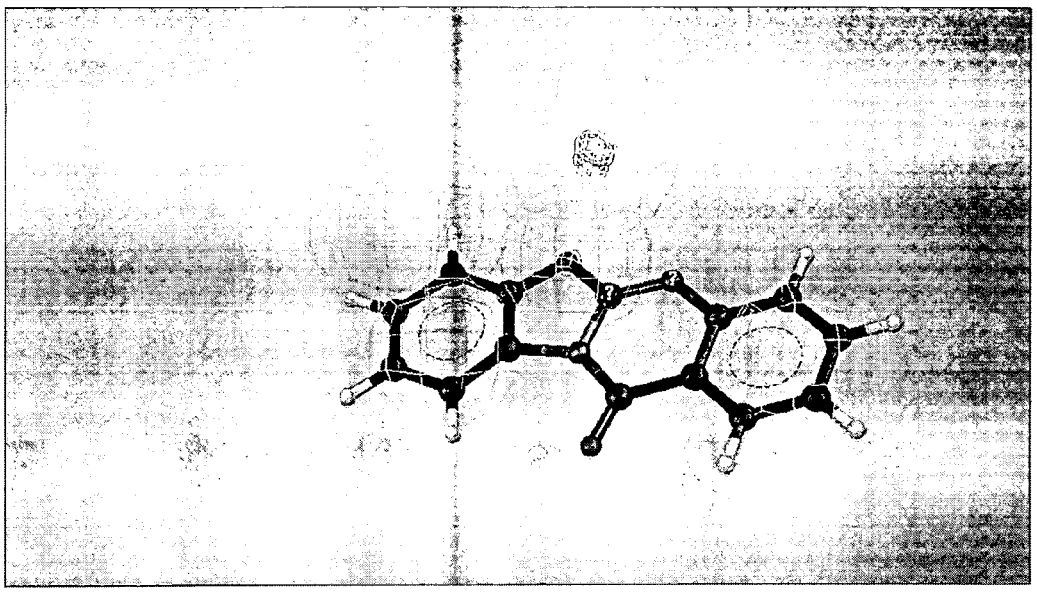
FIG. 2C shows compound 11 mapped to the pharmacophore model of the present invention.
Figure 2D:
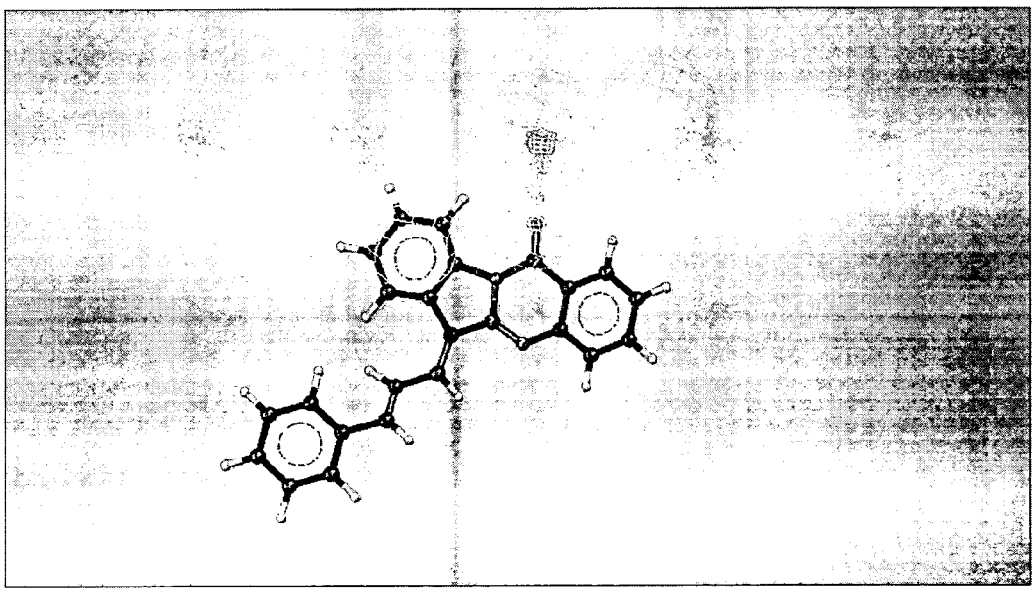
FIG. 2D shows compound 16 mapped to the pharmacophore model of the present invention.

The highly potent analogues of the series of tryptanthrin compounds map all the functional features of the best hypothesis with high scores, whereas the less potent compounds either do not map at all or map fewer of the features. For example, the more potent analogs of the training set such as compounds 1 and 4 map well with the statistically most significant hypothesis (FIGS. 2A & 2B) whereas, the less potent analogues such as compounds 11 and 16 do not map adequately with the hypothesis (FIGS. 2C & 2D).

TABLE 2

| Coordinates | HBA lipid | | HBA lipid | | | |
|---|---|---|---|---|---|---|
| | First Focal Point | Second Focal Point | First Focal Point | Second Focal Point | Hydrophobic | Hydrophobic |
| X | 1.59 | 1.76 | −1.05 | −1.83 | 5.89 | −4.69 |
| Y | 2.40 | 4.83 | 0.51 | 3.29 | 0.40 | −1.17 |
| Z | −2.04 | −3.83 | −2.00 | −2.80 | 0.82 | −1.07 |

The coordinates are dependent upon the particular coordinate system used, and those skilled in the art will recognize that, although rotation and translation of these coordinates may change the specific values of these coordinates, they will in fact define the pharmacophore model of the present invention. The pharmacophore model of the present Two critical sites such as one hydrogen bond acceptor site and one aromatic hydrophobic site appear to be missing in the less potent analogues (FIGS. 2C & 2D). The estimated activity values along with the experimentally determined $IC_{50}$ values for antimalarial activity of the compounds along with the respective error ratios are presented in Table 3.

TABLE 3

Estimated and experimentally determined activity values of the training set and the test set compounds*

| Training set (compd) | $IC_{50}$ (expt.) | $IC_{50}$ (est.) | Error** | Test set (compd) | $IC_{50}$ (expt.) | $IC_{50}$ (est) | Error** |
|---|---|---|---|---|---|---|---|
| 1 | 0.43 | 1.3 | 2.9 | 1' | 7.6 | 19.0 | 2.5 |
| 2 | 0.73 | 1.6 | 2.1 | 2' | 262.9 | 170.0 | −1.5 |
| 3 | 1.8 | 17.0 | 9.4 | 3' | 403.0 | 320.0 | −1.2 |
| 4 | 2.7 | 2.3 | −1.2 | 4' | 1.9 | 1.6 | −1.2 |
| 5 | 11.2 | 70.0 | 6.3 | 5' | 8.5 | 17.0 | 2.0 |

TABLE 3-continued

Estimated and experimentally determined activity values of the training set and the test set compounds*

| Training set (compd) | IC$_{50}$ (expt.) | IC$_{50}$ (est.) | Error** | Test set (compd) | IC$_{50}$ (expt.) | IC$_{50}$ (est) | Error** |
|---|---|---|---|---|---|---|---|
| 6 | 69.0 | 260 | 3.7 | 6' | 7.2 | 17.0 | 2.3 |
| 7 | 120.0 | 23.0 | −5.2 | 7' | 126.0 | 180.0 | 1.4 |
| 8 | 354.3 | 3900 | 11.0 | 8' | 3.8 | 19.0 | 5.0 |
| 9 | 572.9 | 740.0 | 1.3 | 9' | 11.5 | 11.0 | −1.0 |
| 10 | 734.3 | 170.0 | −4.4 | 10' | 1.7 | 1.9 | 1.2 |
| 11 | 50000 | 13000 | −3.9 | 11' | 1.8 | 1.6 | −1.2 |
| 12 | 15626 | 12000 | −1.3 | 12' | 7.7 | 2.7 | −2.8 |
| 13 | 263.0 | 170.0 | −1.5 | 13' | 34.0 | 51.0 | 1.5 |
| 14 | 2589 | 190.0 | −13.0 | 14' | 6.3 | 1.8 | −3.5 |
| 15 | 8780 | 12000 | 1.4 | 15' | 263.8 | 560.0 | 2.1 |
| 16 | 4423 | 12000 | 2.7 | | | | |
| 17 | 6902 | 210.0 | −33.0 | | | | |

*IC$_{50}$ all values are given in ng/ml.
**Values in the error column represent the ratio of the estimated activity to measured activity, or its negative inverse if the ratio is less than one.
The error ratio is defined as the ratio of the estimated activity to measured activity, or its negative inverse if the ratio is less than one within the range of uncertainty 3.

As provided in Example 3, the pharmacophore model was cross-validated by generating a test set of 15 different indolo(2,1-b)quinazoline-6,12-dione analogues compounds which are provided in Table 1. The test set compounds were screened for antimalarial activity against D6 and W2 clones of *P. falciparum* identical to the original training set in vitro. This test set was not used for automatic generation of the pharmacophore and thus, the test set of the tryptanthrin compounds were not used in determining the features of the pharmacophore generated from the original training set.

Figure 3:
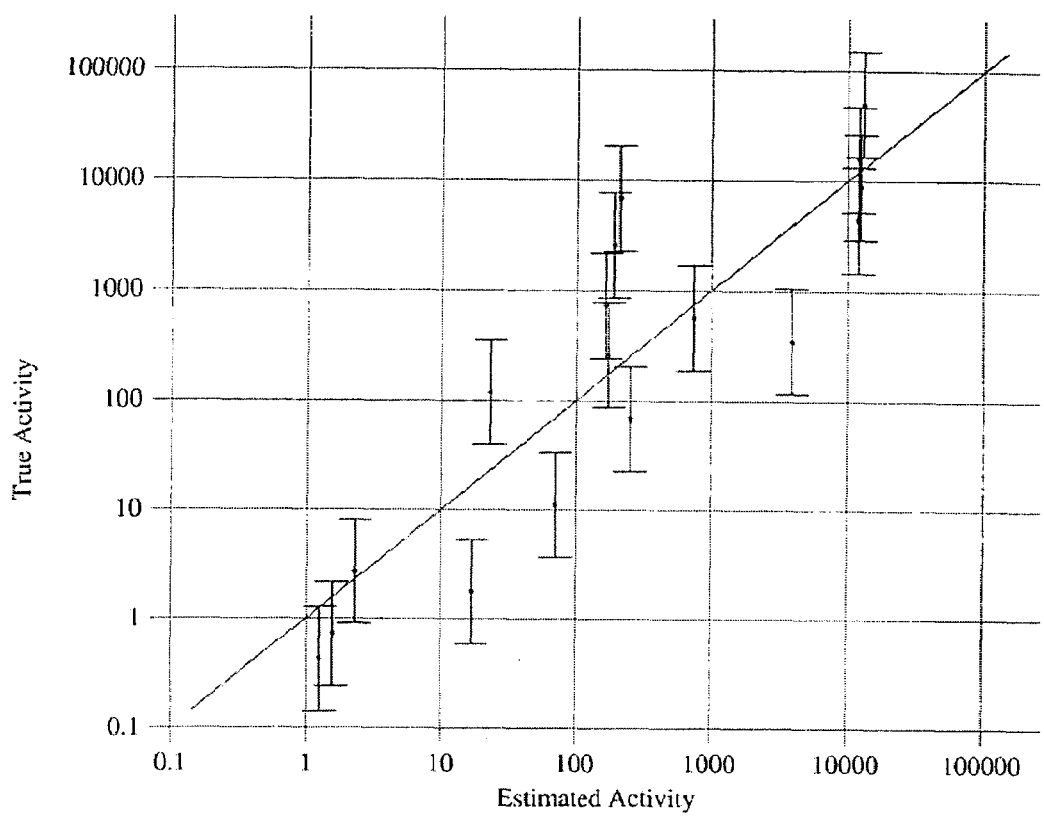
FIG. 3 shows a plot of the experimentally determined $IC_{50}$ values versus the calculated antimalarial activities.
Figure 4A:
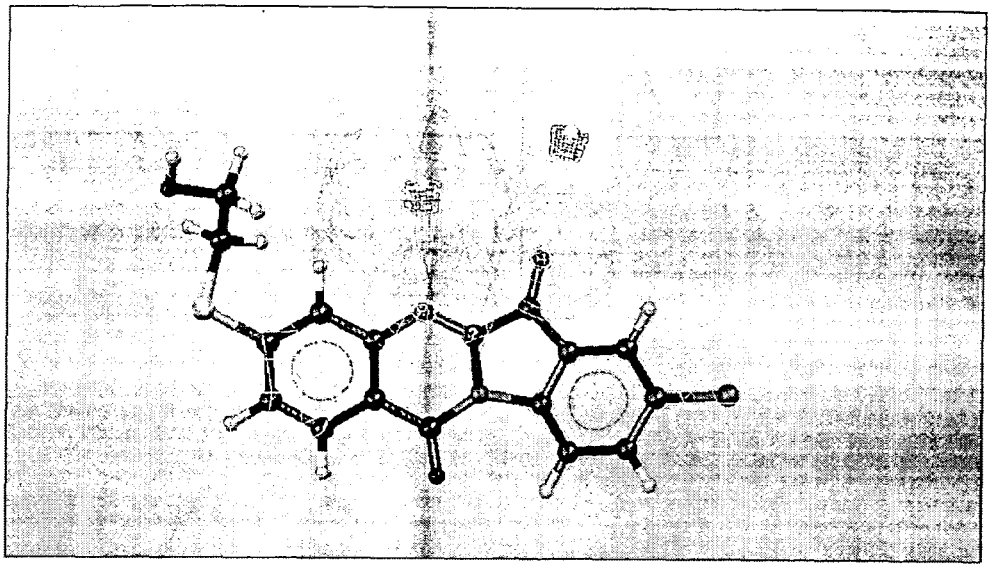
FIG. 4A shows compound 4' mapped to the pharmacophore model of the present invention.
Figure 4B:
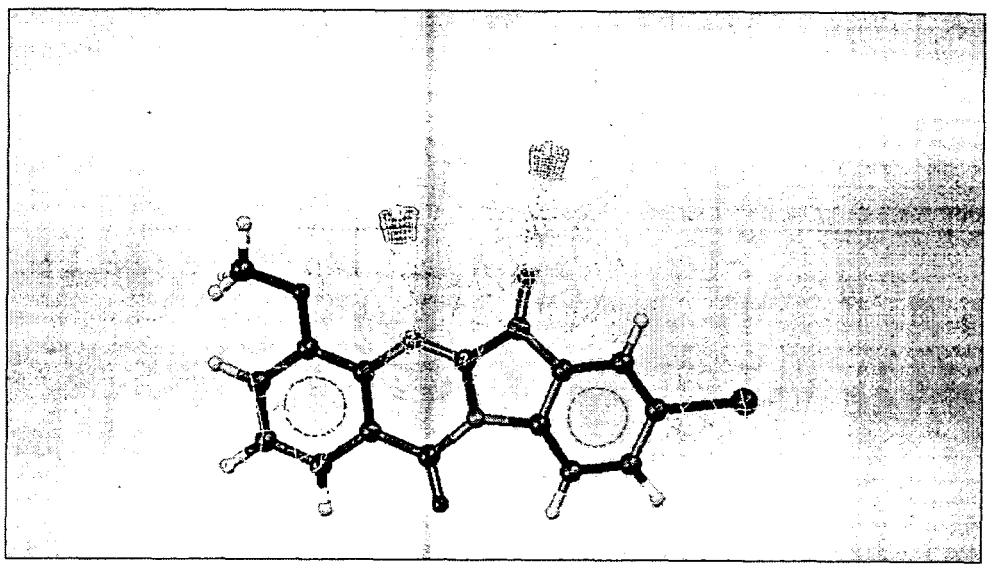
FIG. 4B shows compound 11' mapped to the pharmacophore model of the present invention.

FIG. 3 shows a plot of the experimentally determined IC$_{50}$ values of the training set compounds versus the calculated antimalarial activities and demonstrates a good correlation (R=0.89) within the range of uncertainty 3, indicating the predictive power of the hypothesis. As observed in the training set, the more potent analogues of the test set such as compounds 4' & 11' map well (FIGS. 4A & 4B) with the pharmacophore whereas, the less potent analogues of the test set do not map adequately.

As provided in Example 4, the validity of the pharmacophore model to other commonly used antimalarial drugs was examined. The pharmacophore features were mapped onto a series of eight antimalarial drugs, quinine, chloroquine, mefloquine, primaquine, hydroxychloroquine, pyrimethamine, sulfadoxine, and doxycycline, which are currently used in the United States. See Vroman, J. A. et al. (1999) Curr. Pharm. Design 5:101-138, which is herein incorporated by reference. The pharmacophore maps significantly well with quinine and onto a few well-known antimalarial drugs to varying degrees.

There are 3 parameters such as the "best-score fit", estimate of activity, and conformational energy costs are involved in the present case to assess the quality of the pharmacophore mapping. Considering all three parameters, quinine maps significantly well on the pharmacophore and no other drug tested maps as well.

The mapping of a pharmacophore on the three-dimensional structure of molecule (drug) is carried out by means of a few calculations. The compound to be mapped to a pharmacophore is converted to a three-dimensional configuration and all its conformations with energies are stored in a computer which then performs the analytical calculations which compares the three-dimensional comformers of the compound being mapped and the pharmacophore. Perfect mapping means that the features of the pharmacophore matches exactly with at least one of the conformers of the compound. "Best-fit scores" indicate the degree of matching, conformational energy indicates how much of energy would be spent by the molecule to match the pharmacophore, and estimate of activity is the prediction of activity should the compound be a member of the training set from the pharmacophore was originally developed.

The "best-fit scores", the predicted activity and the conformational energy costs of the antimalarial agents by mapping onto the pharmacophore model are presented in Table 4.

TABLE 4

"Best-Fit" Scores, Estimated Activity and Conformational Energies of Commonly Used Antimalarial Drugs in the United States by Mapping on the Pharmacophore

| Drug | Best-Fit Score | Estimated Activity (ng/ml) | Conformational Energy Costs (kcal/mol) |
|---|---|---|---|
| Quinine | 8.6 | 1.3 | 0.0 |
| Chloroquine (CQ) | 6.5 | 140.0 | 11.2 |
| Mefloquine | 7.0 | 50.0 | 5.1 |
| Primaquine | 6.8 | 82.0 | 2.6 |
| Hydroxy-CQ | 7.3 | 23.0 | 14.6 |
| Pyrimethamine | 4.6 | 12000.0 | 0.0 |
| Sulfadoxine | 7.0 | 49.0 | 6.3 |
| Doxycycline | 6.3 | 23.0 | 0.0 |

Figure 5A:
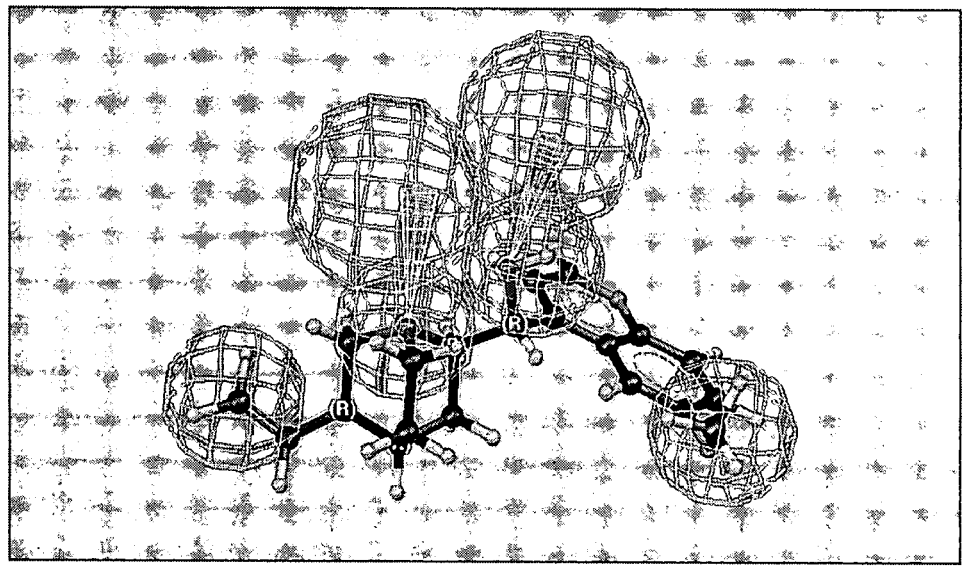
FIG. 5A shows quinine mapped to the pharamacophore model of the present invention.
Figure 5B:
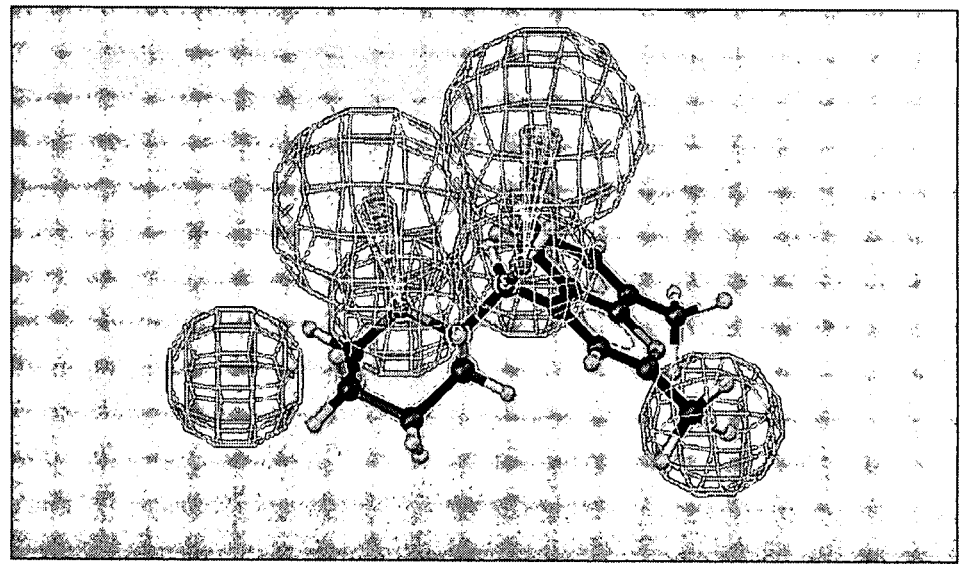
FIG. 5B shows mefloquine mapped to the pharamacophore model of the present invention.
Figure 5C:
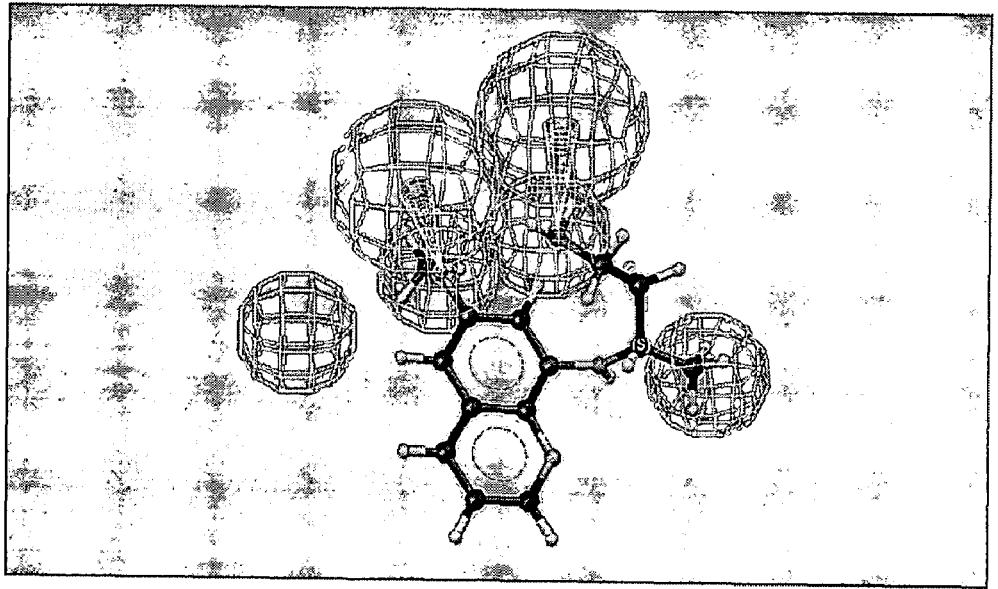
FIG. 5C shows primaquine mapped to the pharamacophore model of the present invention.
Figure 5D:
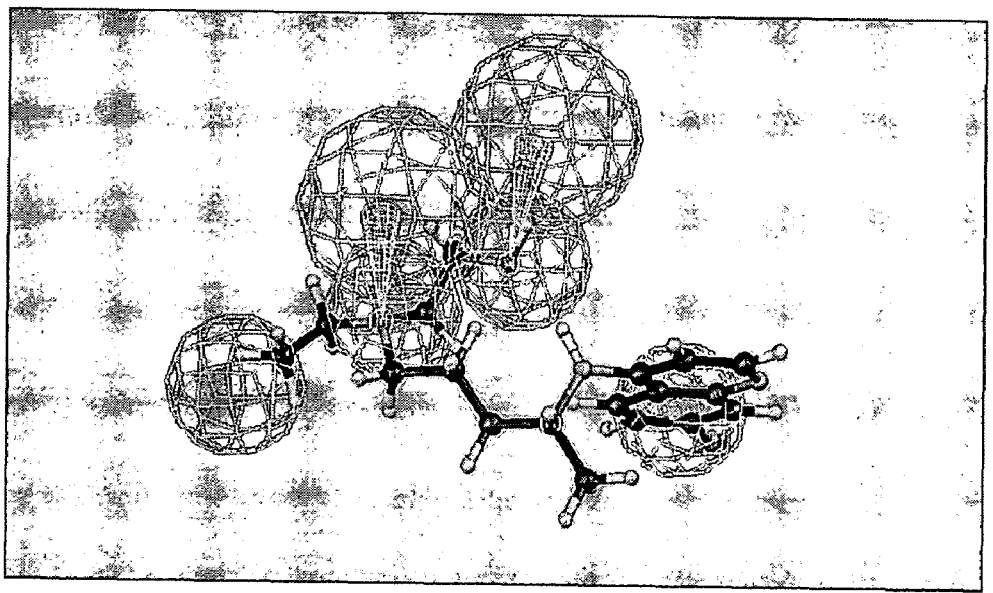
FIG. 5D shows hydroxychloroquine mapped to the pharamacophore model of the present invention.
Figure 5E:
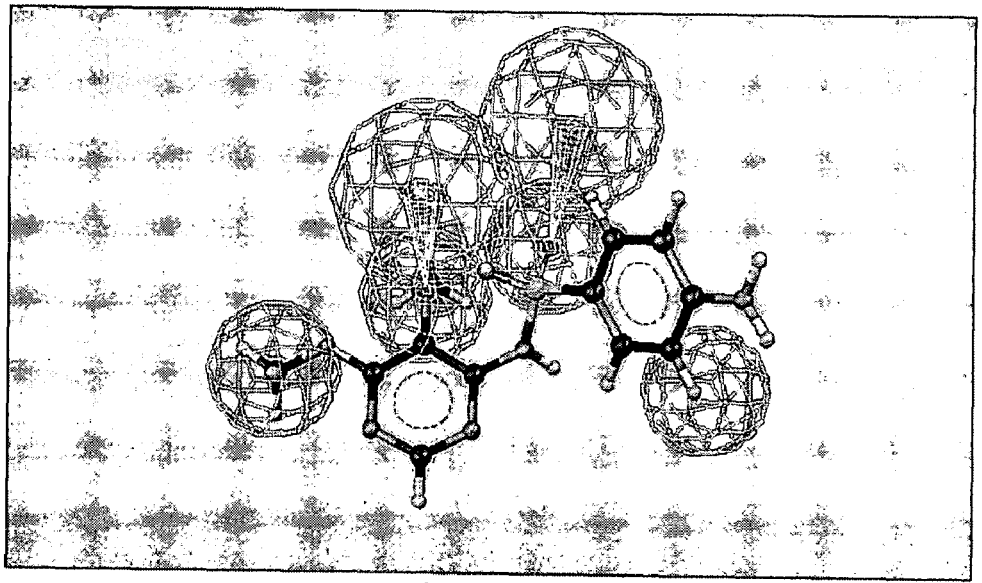
FIG. 5E shows sulfadoxine mapped to the pharamacophore model of the present invention.
Figure 5F:
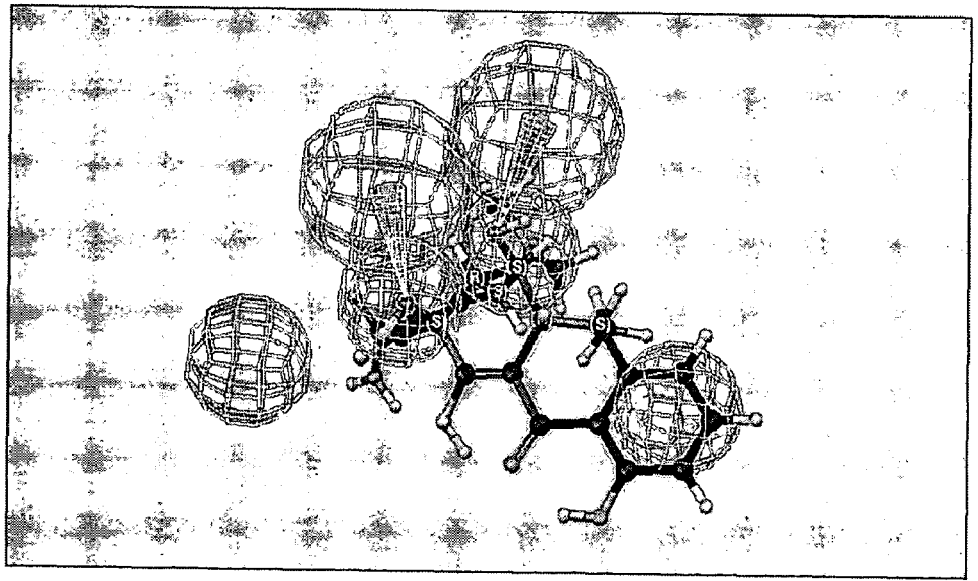
FIG. 5F shows doxycycline mapped to the pharamacophore model of the present invention.
Figure 5G:
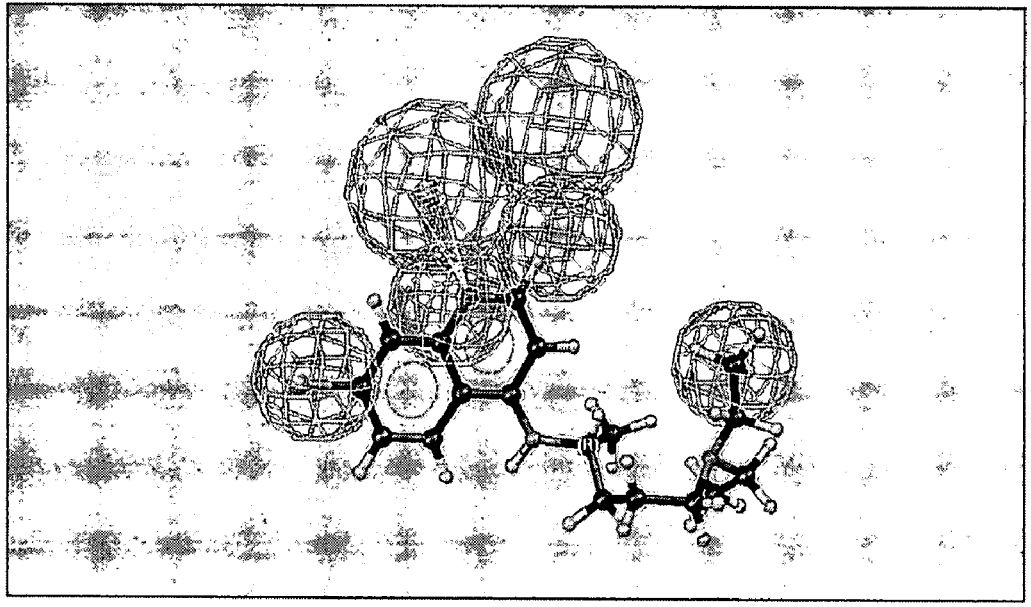
FIG. 5G shows chloroquine mapped to the pharamacophore model of the present invention.
Figure 5H:
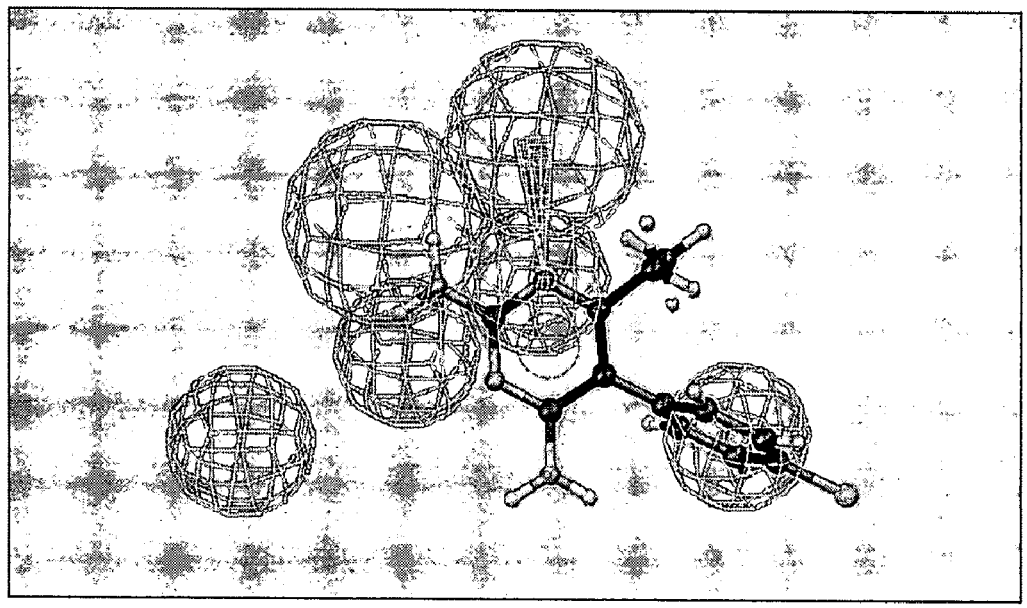
FIG. 5H shows pyrimethamine mapped to the pharamacophore model of the present invention.

Surprisingly, except for quinine, no other drug of the series appears to map well with the pharmacophore (FIG. 5A). Mefloquine (FIG. 5B), primaquine (FIG. 5C), hydroxychloroquine (FIG. 5D), sulfadoxine (FIG. 5E), and doxycycline (FIG. 5F) map the two hydrogen-bond acceptor sites and one of the two hydrophobic sites whereas, chloroquine (FIG. 5G) and pyrimethamine (FIG. 5H) map only one of the two hydrogen-bond acceptors and both the hydrophobic sites do not map at all.

Quinine and other antimalarials that comprise quinoline, including chloroquine, have shown varying capacity to inhibit haem polymerase extracted from *P. falciparum* tropozoites. See Slater, A. F. G. and A. Cerami (1992) Nature 355:167-169; Meshnick, S. R. (1998) From quinine to qinghaosu: historical perspectives, Chapter 24, p. 341-353 in MALARIA PARASITE BIOLOGY, PATHOGENESIS AND PROTECTION Ed. I. W. Sherman, ASM Press, Washington, D.C. Since quinine appears to map the pharmacophore remarkably well and other antimalarials that comprise quinoline appear to map in varying degrees to the pharmacophore model of the present invention, tryptanthrin compounds may target, interact, bind, affect, or modulate haem polymerase, hemin binding studies including NMR analysis was conducted.

As provided in Example 5, the hemin binding affinity for a series of tryptanthrin compounds with functional groups at the 8-position with different electron donating/withdrawing characteristics corresponding with the pharmacophore model of the present invention was determined by $^1$H NMR. The binding interaction was measured as a function of the induced up-field shift in the chemical shift as a function of increasing hemin concentration. $^1$H spectra of selected compounds each analog with an increasing concentration of hemin were collected and analyzed for the effect of the pseudocontact shifts.

Figure 6:
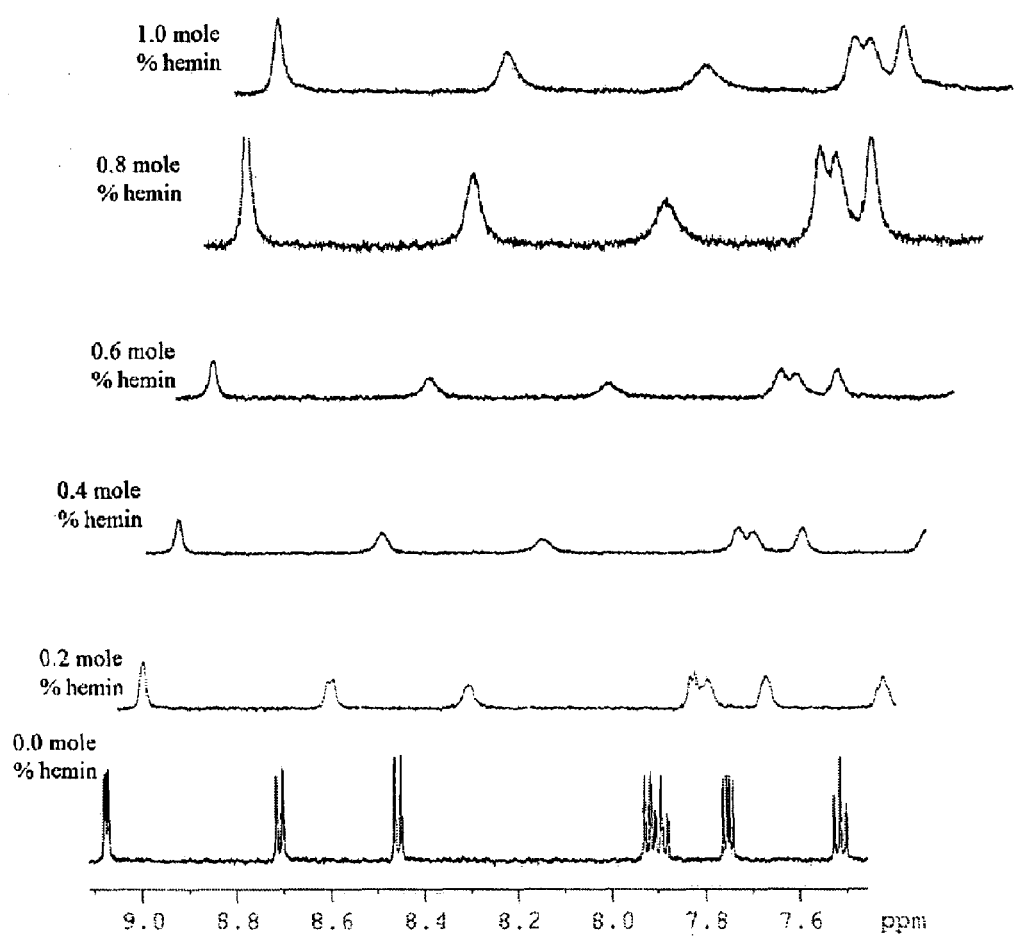
FIG. 6 is a $^1H$ spectrum for the tryptanthrin compound DN49.

It is well known that bio-molecules containing the paramagnetic species $Fe^{+3}$ induce via pseudocontact effect (a thru-space paramagnetic interaction, similar to the thru-space diopolar interaction or NOE) up-field chemical shifts of the $^1$H, $^{13}$C, $^{15}$N atoms of bound ligands. See Serge Moreau et al. (1985) Biochemica et. Biophysica Acta 107-116; Alam, S. L., et al. (1998) J. Biomol. NMR 11:119-133; and Kalodimos, C. G., et al. (2000) J. Inorg. Biochem. 79:371-380, which are herein incorporated by reference. The pseudocontact effect exhibits a distance dependence of $r^{-3}$ and is therefore effective at greater distances. See Crowley, P. B., et al. (2001) J. Am. Chem. Soc. 123:10444-10453, which is herein incorporated by reference. Consequently, the closer a particular proton on the ligand is to the $Fe^{+3}$ atom, the greater the induced Δδ. An example of the $^1$H spectra obtain for a tryptanthrin compound designated DN49 is shown in FIG. 6.

Figure 7:
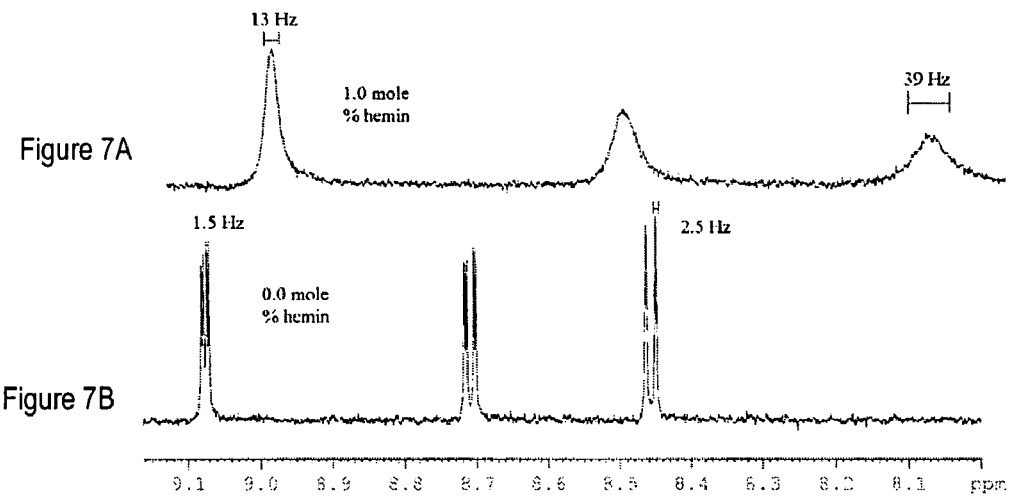
FIG. 7 shows the hemin induced pseudocontact chemical shifts in the tryptanthrin compound DN49.

In addition to the induced up-field shifts in chemical shifts, protons close to the $Fe^{+3}$ atom will experience a greater line-broadening than those protons that are further away and experience a much smaller Δδ. An example of this for DN49 is given in FIG. 7. The maximum observed Δδ and the resulting concentration dependence (slope) for each of the six tryptanthrin compound analogs are provided in Table 5.

TABLE 5

Hemin Induced Pseudocontact Chemical Shifts

| Compound | Maximum induced Δδ (ppm) | Concentration dependence Δδ (ppm/mole %) |
|---|---|---|
| DN9 | 0.462 | 0.08951 |

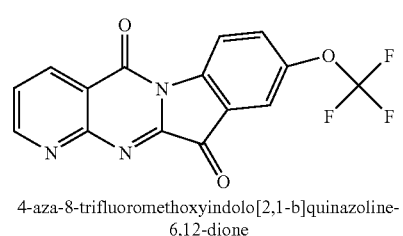

4-aza-8-trifluoromethoxyindolo[2,1-b]quinazoline-6,12-dione

| Compound | Maximum induced Δδ (ppm) | Concentration dependence Δδ (ppm/mole %) |
|---|---|---|
| DN23 | 0.208 | 0.11897 |

4-aza-8-methoxyindolo[2,1-b]quinazoline-6,12-dione

| | | |
|---|---|---|
| DN40 | 1.538 | 0.41595 |

4-aza-8-nitroindolo[2,1-b]quinazoline-6,12-dione

| | | |
|---|---|---|
| DN48 | 0.389 | 0.11897 |

4-aza-9-chloroindolo[2,1-b]quinazoline-6,12-dione

| | | |
|---|---|---|
| DN49 | 0.558 | 0.09778 |

4-azaindolo[2,1-b]quinazoline-6,12-dione

| | | |
|---|---|---|
| DN63 | 0.360 | 0.13656 |

4-aza-8-fluoroindolo[2,1-b]quinazoline-6,12-dione

Figure 8:
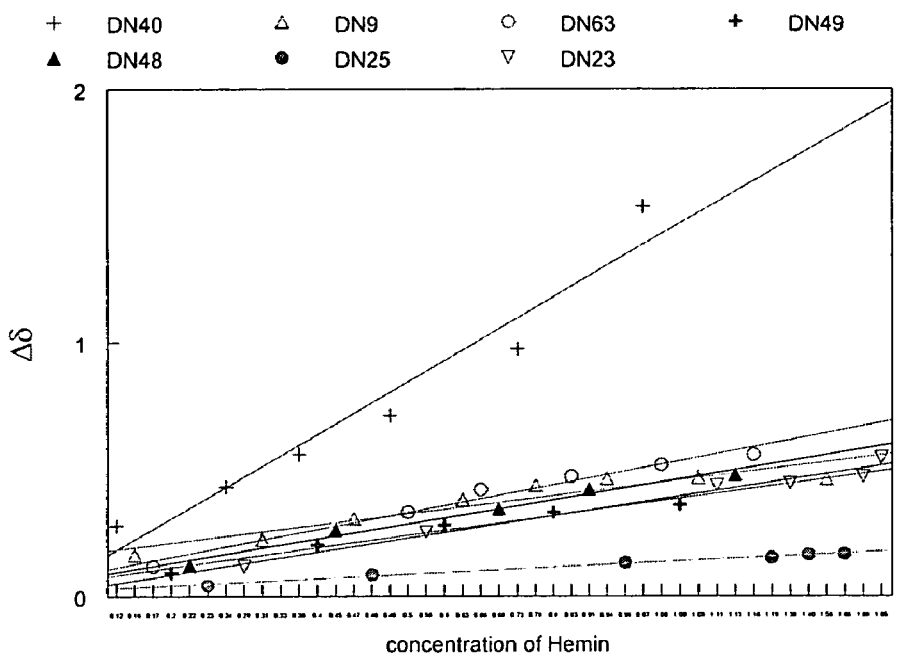
FIG. 8 provides plots of $\Delta\delta$ versus hemin concentration for various tryptanthrin compounds.
Figure 9:
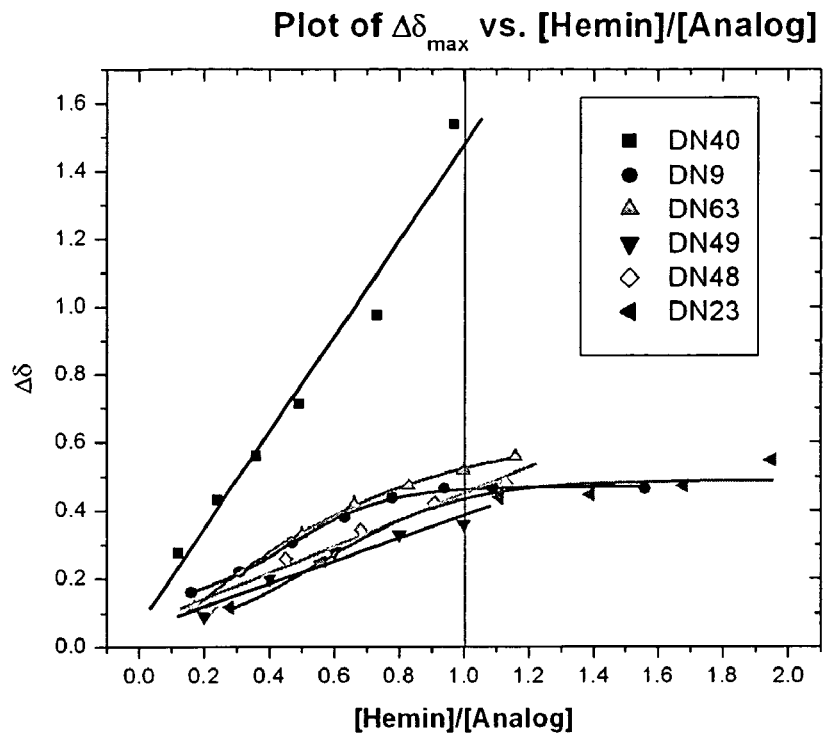
FIG. 9 is a plot of the concentration dependence of the five tryptanthrins listed in Table 5 versus the σ*, electron donating and withdrawing characteristics of seven substituents at position 8.
Figure 10A:
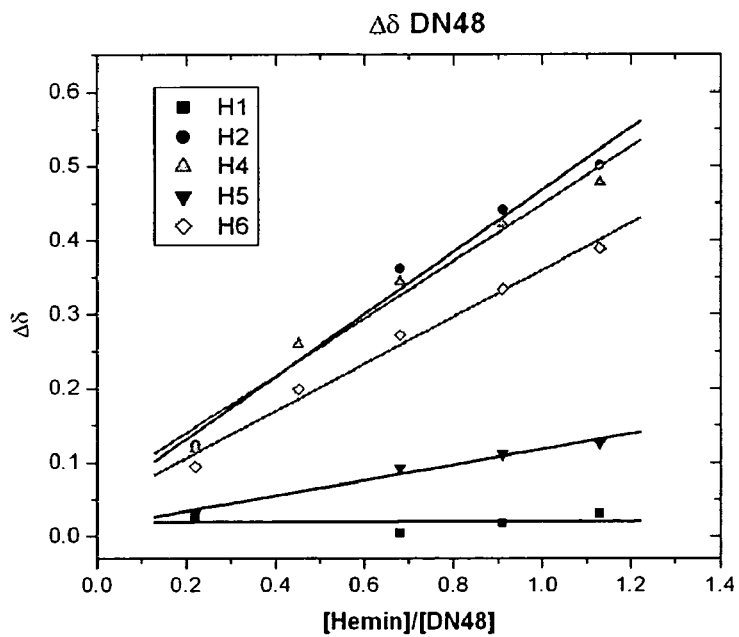
FIG. 10 shows how each tryptanthrin compound with different substituents at position 8 binds hemin with a different orientation.
Figure 10B:
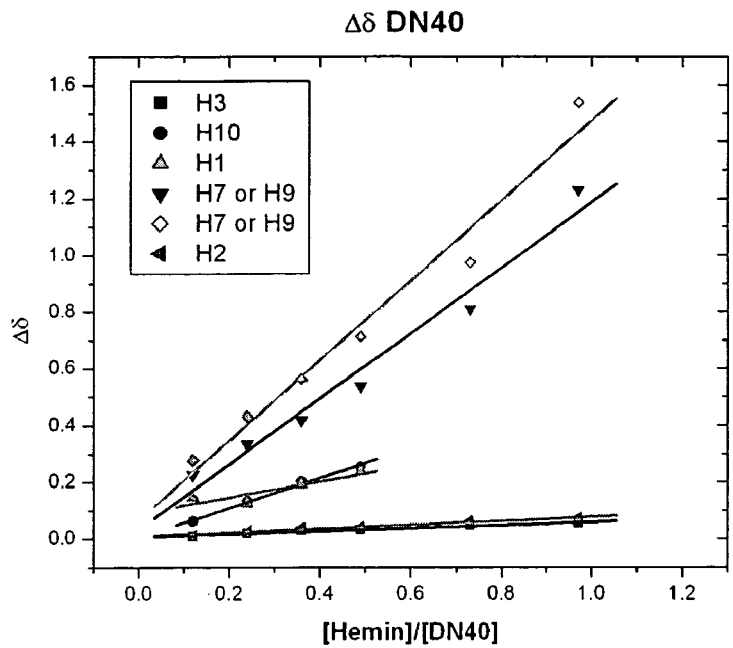
Figure 10C:
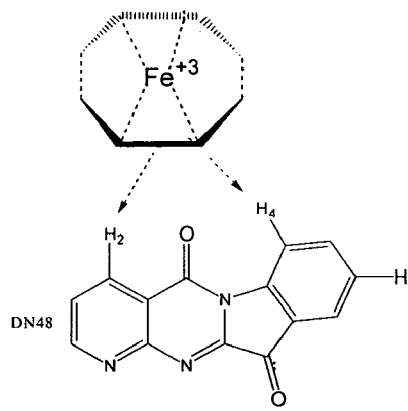
Figure 10C:
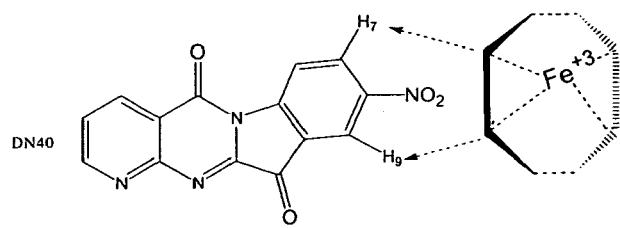

The concentration dependence is obtained by plotting Δδ v. hemin concentration is shown in FIG. 8. FIG. 9, which shows plots of the concentration dependence of each compound listed in Table 5 versus the σ*, electron donating and withdrawing characteristics of six substituents at position 8, indicates a clear relationship of the inductive electron withdrawing/donating character of the functional groups with hemin binding affinity versus the σ*, electron donating and withdrawing characteristics of seven substituents at position 8, indicates a clear relationship of the inductive electron withdrawing/donating character of the functional groups with hemin binding affinity.

Five of the six analogs listed in Table 5 exhibited very similar pseudocontact shifts in both magnitude and in the positions of the protons experiencing the maximum Δδ. However, for DN40 the magnitude and the positions of the protons experiencing the maximum Δδ are different from the other five analogs. It must be remembered that the protons that are closes to the $Fe^{+3}$ atom will experience the greatest pseudocontact shifts (Δδ). Thus, this observation implies that DN40 interacts with the $Fe^{+3}$ of hemin in a different orientation than the other five analogs. The rationale for this conclusion is given in FIG. 10.

In FIG. 10, plots of the pseudocontact shifts for each of the protons on DN48 (FIG. 10A) and DN40 (FIG. 10B) are given. As can be seen from these plots the magnitude of the maximum pseudocontact shift for DN40 is approximately 3 times greater than the maximum pseudocontact shift for DN48. This observation indicates that the proton on DN40 which experiences the maximum pseudocontact shift is much closer in space to the $Fe^{+3}$ atom of hemin than the proton on DN48 which experiences the maximum pseudocontact shift. Thus DN40 forms a more tightly bound complex with the $Fe^{+3}$ atom of hemin than does DN48. FIG. 10C shows the structures of DN40 and DN48 with the two protons in each compound that experience the maximum pseudocontact shifts. As can be seen in the Figure, in the case of DN48 the proton labeled $H_2$ on the A ring and the proton labeled $H_4$ on the D ring of the tryptanthrin experience the maximum pseudocontact shifts and thus are the closest to the $Fe^{+3}$ atom of hemin. Thus the tryptanthrin molecule is oriented relative to the hemin as shown. In the case of DN40 the protons labeled H7 and H9 both on the D ring of the tryptanthrin experience the maximum pseudocontact shifts and are thus the closest to the $Fe^{+3}$ atom of hemin. Therefore, for DN40 tryptanthrin-molecule is oriented relative to the hemin as shown.

Figure 11A:
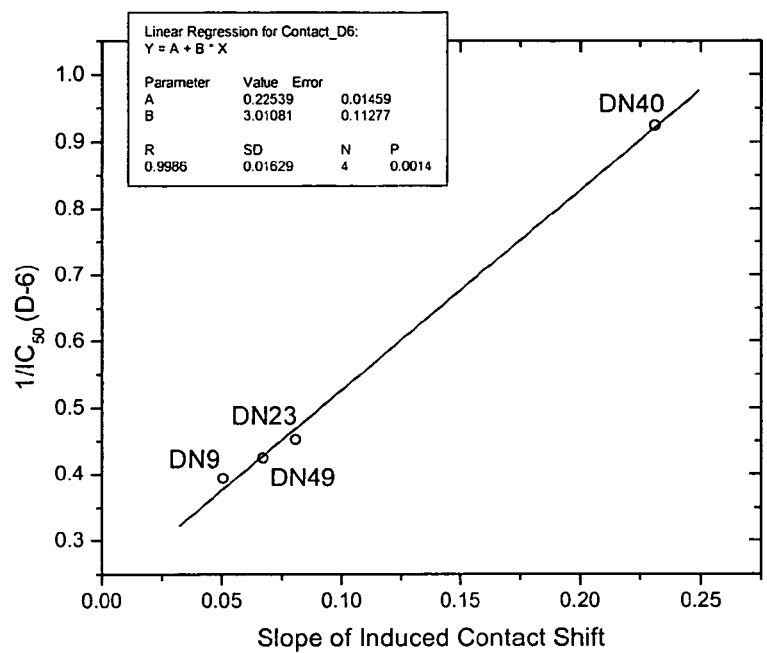
FIG. 11A shows the plots of the biological activity for four of seven analogs v. the concentration dependence of the hemin binding for D6 and indicates that the biological activity is related to hemin binding affinity.
Figure 11B:
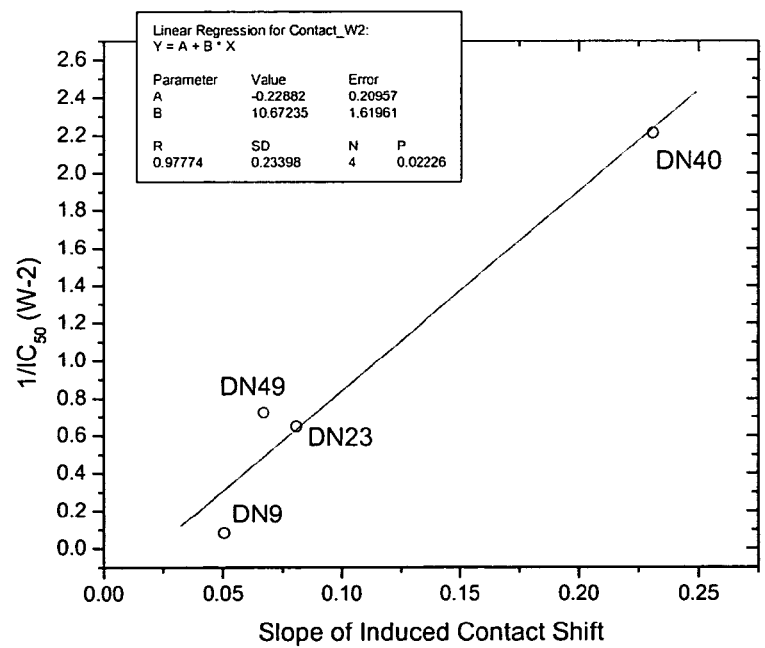
FIG. 11B shows the plots of the biological activity for four of seven analogs v. the concentration dependence of the hemin binding for W2 and indicates that the biological activity is related to hemin binding affinity.

FIG. 11A shows the plots of the biological activity (represented by $1/IC_{50}$) for four of seven compounds (Table 5) versus the concentration dependence of the hemin binding in D6 and FIG. 11B shows similar results for W2. The plot shows an excellent correlation between the biological activity and hemin binding affinity of tryptanthrin compounds, and thereby indicates hemin binding as a likely mode of action of antimalarial compounds that fit or map well to the pharmacophore of the present invention.

In order to provide a theoretical model for the NMR observations, the cation binding affinities of the D ring for four tryptanthrin compounds using sodium ion as the cationic probe were calculated.

Ab initio quantum chemical method at restricted HF level with 6-31G** doubly polarized basis set was used for complete optimization of geometry of the sodium-tryptanthrin complexes and the uncomplexed tryptanthrin molecules.

Shown in Table 6 are the HF/6-31G** calculated relative binding energies (Bes) and atomic charges of few selected atoms in the D ring of the tryptanthrin compounds.

TABLE 6

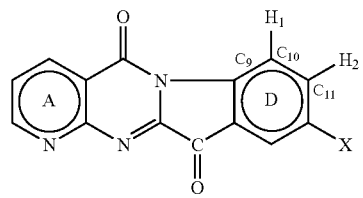

| Compd | —X | Total Atomic Charges | | | | | Relative BE (kcal/mol) | Hemin Binding affinity | Distance Fe..H in min energy docked structures | |
| | | C9 | C10 | C11 | H1 | H2 | | | H1 | H2 |
|---|---|---|---|---|---|---|---|---|---|---|
| 1 | —NO2 | 0.42 | −0.21 | −0.15 | 0.3 | 0.29 | 35.5 | 0.045 | 5.2 | 4.1 |
| 2 | —F | 0.38 | −0.18 | −0.26 | 0.29 | 0.24 | 18.8 | 0.015 | 7.4 | 9.0 |
| 3 | —H | 0.39 | −0.2 | −0.18 | 0.28 | 0.22 | 16.5 | 0.01 | 6.9 | 8.6 |
| 4 | —OCH3 | 0.37 | −0.18 | −0.23 | 0.28 | 0.23 | 17.4 | 0.012 | 9.4 | 12.3 |

As shown in Table 6, the nitro-substituted tryptanthrin compound has the strongest cation binding affinity with the D ring as compared with the rest of the tryptanthrin compounds. In particular, the nitro-substituted tryptanthrin compound has a cation binding affinity of about 16 kcal/mol more strongly than next strongest, the fluoro-substituted tryptanthrin compound. The fluoro-substituted tryptanthrin compound binds to sodium ion by about 2.3 kcal/mol more strongly than the unsubstituted tryptanthrin compound and by about 1.4 kcal/mol from the electron donating —OCH3 substituted tryptanthrin compound.

These hemin binding affinity results, i.e. hemin induced pseudocontact chemical shifts, for the tryptanthrin compounds indicate a clear consistency with the theoretical sodium binding affinities. In addition, these results indicate stronger interaction of hemin with the protons associated with the D ring, particularly H1 and H2. Interestingly, the calculated atomic charges on these protons as well as the three associated carbon atoms in the nitro-substituted analog differ significantly from the others. The location of the cation (sodium ion) in the optimized geometry of the sodium-azotryptanthrin complexes of both nitro- and fluoro-substituted analogues is by the C10/C11 atom in the D ring which corroborates the NMR evidence of stronger hemin interaction at these positions. The position of cation (sodium ion) in the optimized geometry of the other two complexes is found by the centroid of the D ring.

Figure 12A:
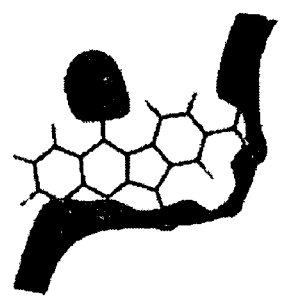
FIG. 12A is 4-aza-8-nitroindolo[2,1-b]quinazoline-6,12-dione.
Figure 12B:
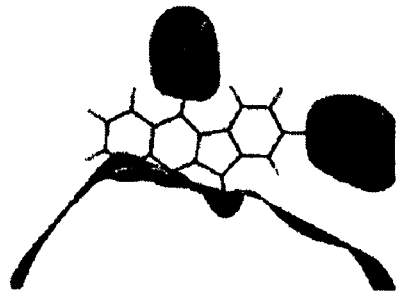
FIG. 12B is 4-aza-8-fluoroindolo[2,1-b]quinazoline-6,12-dione.
Figure 12C:
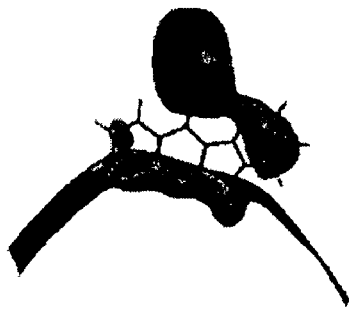
FIG. 12C is 4-azaindolo[2,1-b]quinazoline-6,12-dione.
Figure 12D:
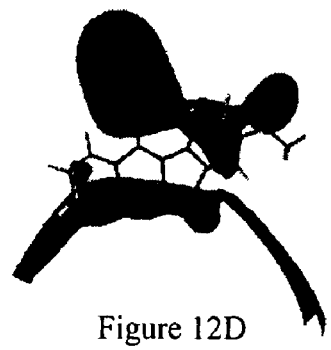
FIG. 12D is 4-aza-8-methoxyindolo[2,1-b]quinazoline-6,12-dione.

The molecular electrostatic potential (MEP) profiles of the uncomplexed tryptanthrin compounds at −1.0 kcal/mol appear to guide the site of interaction with the cation. FIG. 12 shows the electron density maps of selected compounds at approximately 1.40-1.45 angstrom (−1 Kcal/mol) away from the van der Waal's surface. FIG. 12A is 4-aza-8-nitroindolo[2,1-b]quinazoline-6,12-dione. FIG. 12B is 4-aza-8-fluoroindolo[2,1-b]quinazoline-6,12-dione. FIG. 12C is 4-azaindolo[2,1-b]quinazoline-6,12-dione. FIG. 12D is 4-aza-8-methoxyindolo[2,1-b]quinazoline-6,12-dione. The negative electrostatic potential at −1.0 kcal/mol indicates a distribution of electrons beyond the surface of a molecule (van der Waals surface) roughly about 1.4 Å away from the surface. Since this electronic distribution is away from the molecule it is recognizable from a distance for promoting long range intermolecular interactions. A cation being positively charged would find a strong electrostatic recognition interaction with this negative potential region and that is why it will be a guiding feature for tryptanthrin to interact with the cation.

As shown in FIG. 12, the pi-electrons of the D ring in the nitro-substituted tryptanthrin compound become more localized by the C11 atom due to strong electron withdrawing effect of the compound and thus, the cation is likely to prefer a binding site around this location. The trend, though not as strongly as the nitro-substituted, is also noticeable in the electron withdrawing fluoro-substituted tryptanthrin compound analog. As shown in FIG. 12, the large electron distribution over the D ring indicates that the pi electrons of the D ring in the unsubstituted tryptanthrin compound remain unaffected. Thus, the cation (sodium ion) in its optimized complexed structure remain over the centroid of the ring. In the methoxy ($OCH_3$—) substituted tryptanthrin compound, the D ring gets reinforced with electrons due to the electron donating nature of the methoxy substituent and is clearly noticeable from the large electron distribution. See FIG. 12. This reinforcement may be the cause of the binding energy with the cation (sodium ion) increase of about 1.1 kcal/mol as compared to the unsubstituted tryptanthrin compound.

To further understand the binding affinities observed, the complete structures of both hemin and tryptanthrin compounds have been considered and docking calculations using the Docking/affinity module in Insight II (Accelrys Inc., 9685 Scranton Road, San Diego, Calif. 92121-3752) were conducted. See Oprea, T. I. and Marshall, G. R. (1998) Receptor-based prediction of binding affinities. Perspectives in Drug Discovery and Design 9/10/11:35-61; and Insight II User Guide, San Diego: Accelrys Inc. (2002), which are herein incorporated by reference.

Docking/affinity module in Insight II allows calculating the nonbonded energy between two molecules using explicit van der Waals energy, explicit electrostatic (Coulombic) energy, or both van der Waals and electrostatic energies. The number of atoms included in the calculation can be limited by specifying a monomer- or residue-based cutoff. Other methods known in the art may be used, for example, the computation can be done using a pre-computed energy grid.

The force field that best describes the interaction between hemin and the tryptanthrin compounds was found to be "esff" as implemented in the software. Accordingly, the potentials of both hemin and each individual tryptanthrin analogues were fixed at the force field before carrying out the docking calculations. Since the distances between the $Fe^{2+}$ ion and the two protons in the D ring were found to be most affected in the NMR experiments, the calculated nonbonded distance between $Fe^{2+}$ and these two protons are presented in Table 6. The data shown in Table 6 clearly indicate a stronger interaction between hemin and the nitro-substituted tryptanthrin compound as compared with the other tryptanthrin compounds, which is consistent with the NMR experiments as well the experiments using the sodium ion instead the complete hemin molecule.

Preliminary results from NMR studies with some of the tryptanthrin analogues have shown positive indications toward inhibition of the hemin polymerization process (unpublished results). Thus, the present invention also provides a method for treating, preventing, or inhibiting malaria comprising inhibiting or modulating the haem polymerase from the *P. falciparum* tropozoites. In preferred embodiments, the method comprises inhibiting or modulating the haem polymerase with a tryptanthrin compound or a pharmacophore of the present invention.

Indolo[2,1-b]quinazoline-6,12-dione analogs are known to exhibit exceptional in vitro activity against both sensitive and multidrug-resistant malaria. Provided herein are the experimental and theoretical data for the hemin binding affinity of 4-azaindolo[2,1-b]quinazoline-6,12-dione analogs. In $^1$H NMR spectra, paramagnetic $Fe^{+3}$ species, such as in hemin, induce via the pseudocontact effect upfield chemical shifts of proton resonances of bound ligands with concurrent line broadening. There is good correlation between electron donating/withdrawing character of substituents at the 8-position of 4-azaindolo[2,1-b]quinazoline-6,12-dione analogs and hemin binding affinity; furthermore, there is correlation between hemin binding affinity and biological activity. Cation-pi binding affinities of the indolo[2,1-b]quinazoline-6,12-dione D ring were calculated using RHF/6-31G** ab initio quantum chemical method and are found to be consistent with the above observations. Relative binding energies and atomic charges of selected atoms corroborate the NMR data and indicate that the 8-nitro derivative binds in a different mode than the other analogs. Thus, the present invention also provides a method of optimizing hemin binding affinity of a tryptanthrin compound comprising changing or modulating the substituent on the 8-position of the tryptanthrin compound.

As provided in Example 6, the pharmacophore model of the present invention was used to search an in-house database, Chemical Information System (Chemical Information System, Division of Experimental Therapeutics, Walter Reed Army Institute of Research, Silver Spring, Md.) to screen for potential new antimalarial agents. Specifically, the three-dimensional pharmacophore of the present invention was used as a template for search three-dimensional multi-conformer databases. Three-dimensional multi-conformer databases of molecules comprise all possible conformations of the three-dimensional structure of each molecule in the database within an energy range of 0 to 25 kcal/mol. The three-dimensional structures in the databases were mapped to or compared with the three-dimensional pharmacophore of the present invention to identify compounds having the same or similar three-dimensional conformations.

The Chemical Information System database has over 240,000 compounds and was transformed into a multiconformer database in CATALYST® using the catDB® utility program as implemented in the software. The catDB® format allows a molecule to be represented by a limited set of conformations thereby permitting conformational flexibility to be included during the search of the database. Five amino-quinazoline compounds were identified as promising candidates. As provided in Example 6, all five candidate compounds were found to exhibit potent in vivo activity in mouse malarial screening test. See e.g. Hill, J, (1975) Ann. Trop. Med. Parasitol. 69:421-427, and U.S. Pat. No. 6,284,772, which are herein incorporated by reference. Therefore, the present invention also provides methods of treating malaria with an amino-quinazoline compound.

The present invention also provides a method of screening candidate compounds for antimalarial activity comprising using the pharmacophore of the present invention.

The pharmacophore models of the present invention can be used to evaluate antimalarial activity and potency of a candidate compound. The candidate compounds being evaluated may be designed de novo using the models of the invention, or alternatively, be a compound, e.g., chosen from a library of compounds. Using the pharmacophore model of the invention and the methods of identification disclosed herein, one may predict the antimalarial potency of a candidate compound based upon its fit with the pharmacophore model of the invention. Further, one may even predict the relative degree of antimalarial potency via, the methods of the invention by calculation of the $K_1$ (apparent) value for a compound.

After identifying a candidate compound to be evaluated for antimalarial potency, the three-dimensional structure of the compound may be determined. This may already have been done if, e.g., the compound was obtained from a structural database wherein three-dimensional x, y and z coordinates were used to define the compound. Alternatively, the three-dimensional structures of small molecules can be readily determined by methods known to those of skill in the art, including but not limited to, X-ray crystallography, nuclear magnetic resonance spectrometry, etc. The structures obtained from structural databases are usually the structures of compounds alone, uncompleted with other molecules. If the three-dimensional structure is not known, one may use computer programs, such as CATALYST™, to predict the three-dimensional structure of the compound. Three-dimensional conformers may be generated from a starting structure using methods well known in the art such as the Best or Fast Conformational Analyses (Molecular Simulations, Inc., San Diego, Calif.) with an energy set to a range of 0 to 50 Kcal/mol, preferably 0 to 35 Kcal/mole, and most preferably 0 to 10 Kcal/mole, and the maximum number of conformations set to 100, preferably 175, and most preferably 255. The pharmacophore model may be then compared to a given compound using tools to compare the structural features of each, such as COMPARE™ within the VIEW HYPOTHESIS™ workbench (Molecular Simulations, Inc., San Diego, Calif.).

The degree of fit of a particular compound structure to the pharmacophore model may be calculated by determining, using computer methods, if the compound possesses the chemical features of the model and if the features can adopt the necessary three-dimensional arrangement to fit the model. The modeling program will indicate those features in the model having a fit with the particular compound.

In preferred embodiments, the present invention encompasses compounds that exhibit antimalarial activity and map well to the pharmacophore model disclosed herein. For example, antimalarial compounds that may be suitably superimposed on a three-dimensional representation of the pharmacophore model of the present invention using computational methods well known to those of skill in the art. A superposition of structures and the pharmacophore model is defined as a minimization of the root mean square distances between the centroids of the corresponding features of the molecule and the pharmacophore. A van der Waals surface is then calculated around the superimposed structures using a computer program such as CERIUS™ (Molecular Simulations, Inc., San Diego, Calif.).

Although the tryptanthrin compounds have been shown to possess outstanding in vitro activity against *P. falciparum* (both W2 & D6 clones), prior art tryptanthrin compounds exhibit limited in vivo activity, indicating bioavailability problems. Thus, as described herein, different tryptanthrin compounds were synthesized and tested. One derivative, tryptanthrin compound C, exhibit a marked increase in solubility over prior art tryptanthrin compounds.

The experiments described in Examples 7-9 indicate that the biological activity of tryptanthrin compounds are related to the ability of the compounds to undergo reversible single electron transfers in a biological system. The results of Example 7-9 substantiate the pharmacophore model of the present invention. In particular the $IC_{50}$ values correlate with redox potentials and the redox potentials correlate with C6 carbonyl IR data, but not the C12 IR data. Therefore, in the pharmacophore model of the present invention, the C6 carbonyl.

The tryptanthrin compounds of the present invention may be made according to methods known in the art or as described herein. See e.g. Example 10.

In preferred methods, a tryptanthrin compound having the structural formula B may be made according to the following Scheme 1 using conventional methods known in the art:

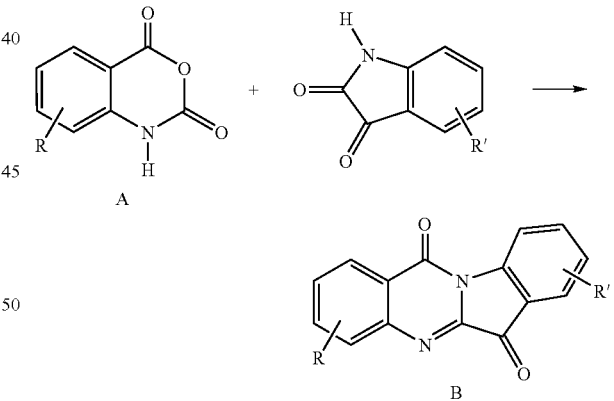

Isatoic anhydride A may be made according to the following Scheme 2 using conventional methods known in the art:

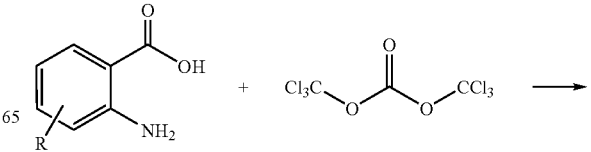

-continued

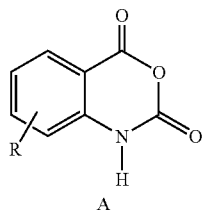

A

See Coppola, G. M. (1980) Synthesis 505, which is herein incorporated by reference. Alternatively, isatoic anhydride A may be obtained from commercial source. Isatin may be obtained commercially or by methods known in the art. See e.g. Popp, F. E. (1975) Adv. Het. Chem. 18:1; and Marvel, C. S. and Hiers, G. S. in Organic Syntheses, 2$^{nd}$ ed. Blat, A. H., ed. New York (1941) pp 327-330, which are herein incorporated by reference. Tryptanthrin compound B may be further derivatized to make a tryptanthrin compound C according to Scheme 3 of Example 10. See also U.S. Pat. No. 5,441,955, which is herein incorporated by reference.

The use of prior art tryptanthrin compounds as pharmaceuticals has been limited as the prior art tryptanthrin compounds suffer from poor solubility and poor bioavailability. Previous tryptanthrin compounds typically have limited solubility even in dimethyl sulfoxide (4-8 mg/mil) and have no appreciable (<0.1 mg/ml) solubility in hexanes, ethyl acetate, ether, toluene, dichloromethane, chloroform, methanol, ethanol, water, or acetone.

As provided in Example 11, the solubility of tryptanthrin compound in a given solvent is vastly improved by being associated with N—H, OH, and (hetero)aromatic functions. Therefore, the present invention provides tryptanthrin compounds that are more soluble and bioavailable than prior art tryptanthrin compounds. Specifically, the present invention provides a method for improving the solubility, bioavailability, or both of a tryptanthrin compound which comprises dissolving the tryptanthrin compound in a solvent having at least one N—H, OH, or (hetero)aromatic function such as pyrrole, indole, pyridine, isoquinoline, nitrobenzene, aniline, N-methylbenzylamine, piperidine, pyrrolidine, phenol, benzyly alcohol, benzoic acid, 1,4-dioxane, and the like, then adding to deionized water and then removing the solvent by evaporation.

Unlike prior art tryptanthrin compounds, tryptanthrin compound C exhibits solubility in chloroform in excess of 5 mg/ml. As close association with N—H, OH, and (hetero) aromatic functions improves the solubility and/or bioavailability of tryptanthrin compounds, the present invention also provides tryptanthrin compounds having such functions as substituents. For example, in some embodiments, the tryptanthrin compounds of the present invention have the following structural formula (IV)

(IV)

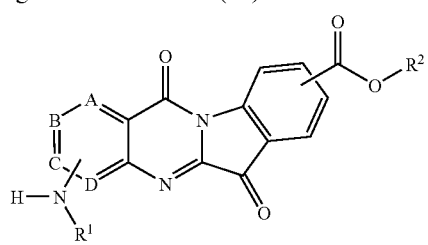

wherein A, B, C, and D are each independently selected from the group consisting of C, N, and S;

$R^1$ and $R^2$ are each independently selected from the group consisting of polypeptides, polyamines, polyethers or -L-$R^3$ wherein L is a linker and $R^3$ is substituted or unsubstituted

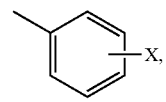

substituted or unsubstituted

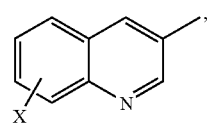

substituted or unsubstituted wherein X is one or more substituents selected from the group consisting of alkyl, hydroxyl, alkoxy, acyl, amino, alkylamino, dialkylamino, alkoxycarbonyl, carboxyl, carbamoyl, alkylaminocarboxyl, dialkylaminocarboxyl, alkylthio or mercapto and the linker comprises about 2 to about 18 carbon, nitrogen, oxygen or sulfur atoms in its chain selected from the group consisting of alkyl, alkylamino, dialkylamino, alkoxyl, alkoxycarbonyl, alkylaminocarbonyl, dialkylaminocarbonyl, alkylthio, and carbamoyl groups.

Therefore, the present invention provides soluble and/or bioavailable tryptanthrin compounds and pharmaceutical compositions comprising the soluble and/or bioavailable tryptanthrin compounds.

Tryptanthrin compounds have been found to exhibit activity against diseases and disorders associated with cell proliferation, bacterial infections, and protozoal infections. See U.S. Pat. No. 5,441,955 (activity against *Mycobacterium*); U.S. Pat. No. 6,284,772 (activity against *Plasmodium*) Honda, G. et al. (1979) Planta Med. 37(2):172-174 (antimicrobial specificity); Honda and Tabata (1979) Planta Med. 36(1):85-90 (antifungal); Honda, G. (1980) Planta Med. 38(3):275-276 (antidermatophytic); Seifert and Unger (1994) Z Naturforsch 49(1-2):44-48 (insecticidal and fungicidal); Mitscher and Baker (1998) Med. Res. Rev. 18(6): 363-374 (tuberculosis therapy); Hosoe, T. et al. (1999) Mycopathologia 146(1):9-12 (cytotoxicity against lymphoma cells); Kimoto, T. et al. (1999) Natural Medicines 53(2):72-79 (cytotoxic effects on malignant tumor cells); Yonghong, L. et al. (2000) Chinese Traditional and Herbal Drugs 31(7):531-545 (in vitro anticancer activity of tryptanthrin B); Koya-Miyata, S. et al. (2001) Anticancer Res. 21(5):3295-3300 (prevention of intestinal tumors); Kimoto, T. et al. (2001) Pathol. Int. 51(5):315-325 (apoptosis of leukemia cells); Kataoka, M. et al. (2001) J. Gastroenterol. 36(1):5-9 (activity against *Helobacter*); Micallef, M. J. et al. (2002) Int. Immunopharmacol 2(4):565-578 (treatment of colitis); and Scovill, J. et al. (2002) Antimicrob. Agents Chemother. 46(3):882-883 (antitrypanosomal activity); which are herein incorporated by reference. As prior art tryptanthrin compounds exhibit poor solubility and bioavailability, the present invention provides methods of treating, preventing, or inhibiting diseases and disorders associated with cell proliferation, bacterial infection, fungal infection, and protozoal infection which comprises administering at least one tryptanthrin compound made by the methods disclosed herein.

Diseases and disorders related to cell proliferation include cancer, papillomas, acute and chronic inflammation, rheumatoid arthritis, psoriasis, atherosclerosis, diabetic retinopathy, chronic obstrusive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crohn's disease, silicosis, and the like. In preferred embodiments, the cancer is leukemia, CNS cancer, renal cancer, non-small cell lung cancer, melanoma, prostate cancer, colon cancer, ovarian cancer, or breast cancer. Bacterial infections include *Streptococcal, Staphylococcal*, bacterial meningitis, *Yersinia pestis, Enterobacter, Helicobacter, Bacillus anthracis, Escherichia coli, Mycobacterium*, and the like. In preferred embodiments, the bacterial infection is caused by *Mycobacterium tuberculosis*. Fungal infections include histoplasmosis, coccidioidomycosis, blastomycosis, paracoccidioidomycosis, sporotrichosis, cryptococcosis, candidiasis, aspergillosis, mucormycosis, and the like. Protozoal infections include malaria, leishmaniasis, trypanosomiasis, and the like.

Since the pharmacophore of the present invention was created using a training set of tryptanthrin compounds, the present invention also provides methods of using the pharmacophore for treating, preventing, or inhibiting a bacterial infection or a disease or disorder associated with cell proliferation in a subject. The methods include using the pharmacophore of the present invention to screen for a compound that exhibits activity against a disease or disorder associated with cell proliferation or a bacterial infection and then administering the compound to a subject in need thereof.

Diseases and disorders related to cell proliferation include cancer, papillomas, acute and chronic inflammation, rheumatoid arthritis, psoriasis, atherosclerosis, diabetic retinopathy, chronic obstrusive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crolm's disease, silicosis, and the like. In preferred embodiments, the cancer is leukemia, CNS cancer, renal cancer, non-small cell lung cancer, melanoma, prostate cancer, colon cancer, ovarian cancer, or breast cancer. Bacterial infections include *Streptococcal, Staphylococcal*, bacterial meningitis, *Yersinia pestis, Enterobacter, Helicobacter, Bacillus anthracis, Escherichia coli, Mycobacterium*, and the like. In preferred embodiments, the bacterial infection is caused by *Mycobacterium tuberculosis*. Fungal infections include histoplasmosis, coccidioidomycosis, blastomycosis, paracoccidioidomycosis, sporotrichosis, cryptococcosis, candidiasis, aspergillosis, mucormycosis, and the like. Protozoal infections include malaria, leishmaniasis, trypanosomiasis, and the like.

Therefore, the present invention also provides tryptanthrin compounds having increased solubility, bioavailability, or both, and methods of making thereof.

In accordance with a convention used in the art, ⤴ is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl" is intended to mean a straight or branched chain monovalent radical of saturated and/or unsaturated carbon atoms and hydrogen atoms, such as methyl (Me), ethyl (Et), propyl (Pr), isopropyl (i—Pr), butyl (n—Bu), isobutyl (i—Bu), t—butyl (t—Bu), (sec—Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl" is intended to mean a non-aromatic monovalent monocyclic, bicyclic, or tricyclic radical comprising 3-14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

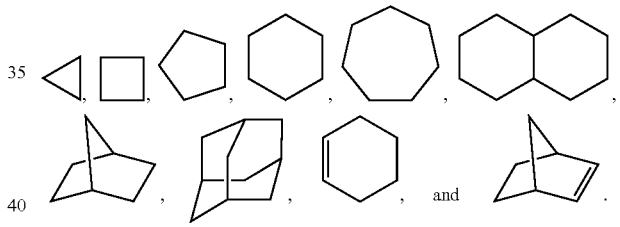

A "heterocycloalkyl" is intended to mean a non-aromatic monovalent monocyclic, bicyclic, or tricyclic radical, which is saturated or unsaturated, comprising 3-18 ring members, which includes 1-5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

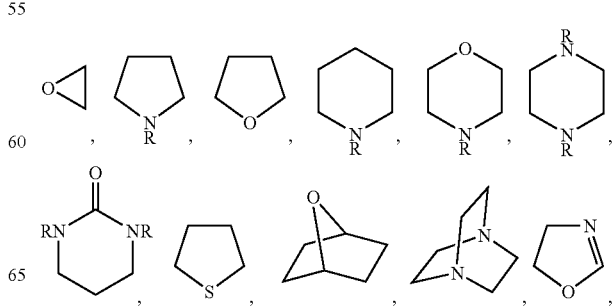

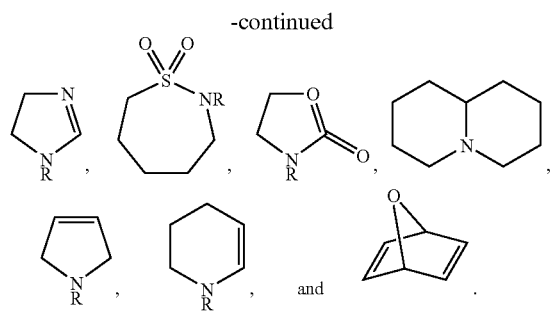

An "aryl" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

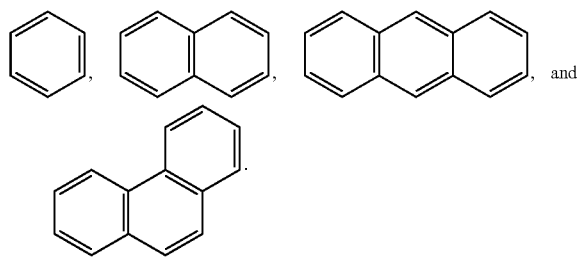

A "heteroaryl" is intended to mean an aromatic monovalent monocyclic, bicyclic, or tricyclic radical comprising 4-18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

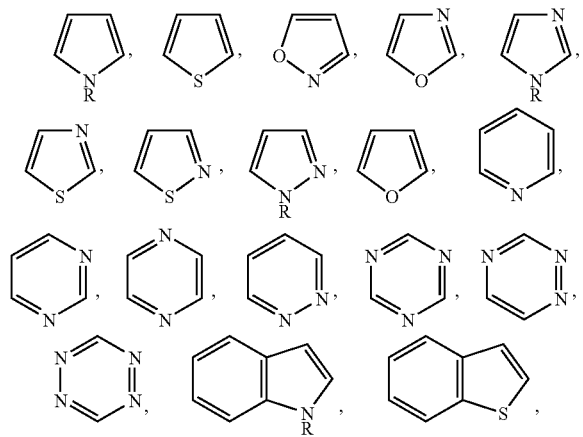

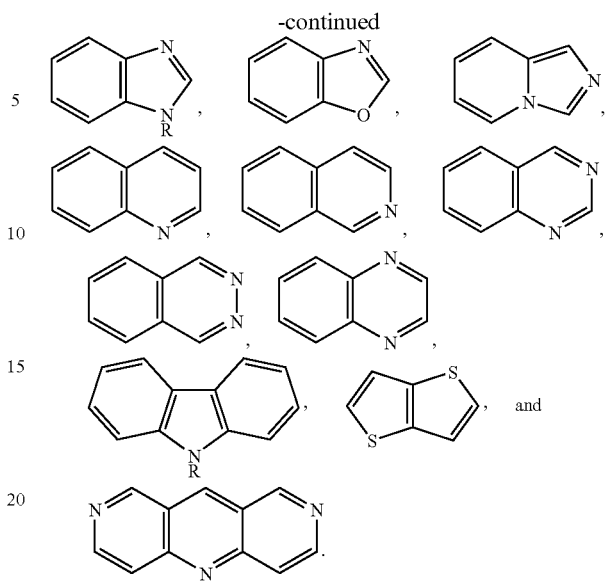

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl" is intended to mean a —C(O)—$R^a$ radical, where $R^a$ is a suitable substituent as defined below.

A "thioacyl" is intended to mean a —C(S)—$R^a$ radical, where $R^a$ is a suitable substituent as defined below.

A "sulfonyl" is intended to mean a —$SO_2R^a$ radical, where $R^a$ is a suitable substituent as defined below.

A "hydroxyl" is intended to mean the radical —OH.

An "amino" is intended to mean the radical —$NH_2$.

An "alkylamino" is intended to mean the radical —$NHR^a$, where $R^a$ is an alkyl group.

A "dialkylamino" is intended to mean the radical —$NR^aR^b$, where $R^a$ and $R^b$ are each independently an alkyl group.

An "alkoxyl" is intended to mean the radical —$OR^a$, where $R^a$ is an alkyl group. Exemplary alkoxyl groups include methoxyl, ethoxyl, propoxyl, and the like.

An "alkoxycarbonyl" is intended to mean the radical —$C(O)OR^a$, where $R^a$ is an alkyl group.

An "alkylsulfonyl" is intended to mean the radical —$SO_2R^a$, where $R^a$ is an alkyl group.

An "alkylaminocarbonyl" is intended to mean the radical —$C(O)NHR^a$, where $R^a$ is an alkyl group.

A "dialkylaminocarbonyl" is intended to mean the radical —$C(O)NR^aR^b$, where $R^a$ and $R^b$ are each independently an alkyl group.

A "mercapto" is intended to mean the radical —SH.

An "alkylthio" is intended to mean the radical —$SR^a$, where $R^a$ is an alkyl group.

A "carboxyl" is intended to mean the radical —C(O)OH.

A "carbamoyl group" is intended to mean the radical C(O)NH$_2$.

An "aryloxyl" is intended to mean the radical —OR$^c$, where R$^c$ is an aryl group.

A "heteroaryloxyl" is intended to mean the radical —OR$^d$, where R$^d$ is a heteroaryl group.

An "arylthio" is intended to mean the radical —SR$^c$, where R$^c$ is an aryl group.

A "heteroarylthio" is intended to mean the radical —SR$^d$, where R$^d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, 3$^{rd}$ edition, John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); C$_{1-6}$-alkyl; C$_{1-6}$-alkenyl; C$_{1-6}$-alkynyl; hydroxyl; C$_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl,-aryl; aryl-lower alkyl; CO$_2$CH$_3$; CONH$_2$; OCH$_2$CONH$_2$; NH$_2$; SO$_2$NH$_2$; OCHF$_2$; CF$_3$; OCF$_3$; and the like. Such moieties may also be optionally substituted by a fused-ring structure or bridge, for example OCH$_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See, for example, Lee et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or ©, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011-2016; Shan, D. et al., J. Pharm. Sci., 86(7):765-767; Bagshawe K., (1995) Drug Dev. Res. 34:220-230; Bodor, N., (1984) Advances in Drug Res. 13:224-331; Bundgaard, H., Design of Prodrugs (Elsevier Press, 1985); and Larsen, I. K., Design and Application of Prodrugs, Drug Design and Development (Krogsgaard-Larsen et al., eds., Harwood Academic Publishers, 1991).

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound of the present invention and salts may exist in different crystal or polymorphic forms, all of which are intended to be within the scope of the present invention and specified structural formulas.

The compounds of the present invention in accordance with the present invention are useful in the treatment of diseases and disorders associated with cell proliferation, bacterial infection, fungal infection, and protozoal infection. Diseases and disorders related to cell proliferation include cancer, papillomas, acute and chronic inflammation, rheumatoid arthritis, psoriasis, atherosclerosis, diabetic retinopathy, chronic obstrusive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crohn's disease, silicosis, and the like. In preferred embodiments, the cancer is leukemia, CNS cancer, renal cancer, non-small cell lung cancer, melanoma, prostate cancer, colon cancer, ovarian cancer, or breast cancer. Bacterial infections include *Streptococcal, Staphylococcal*, bacterial meningitis, *Yersinia pestis, Enterobacter, Helicobacter, Bacillus anthracis, Escherichia coli, Mycobacterium*, and the like. In preferred embodiments, the bacterial infection is caused by *Mycobacterium tuberculosis*. Fungal infections include histoplasmosis, coccidioidomycosis, blastomycosis, paracoccidioidomycosis, sporotrichosis, cryptococcosis, candidiasis, aspergillosis, mucormycosis, and the like. Protozoal infections include malaria, leishmaniasis, trypanosomiasis, and the like.

The antiproliferative, antibacterial, antifungal, and antiprotozoal activities of the compounds of the present invention may be measured by any of the methods available to those skilled in the art, including in vitro and in vivo assays. Examples of suitable assays for activity measurements are provided herein. Properties of the compounds of the present invention may be assessed, for example, by using one or more of the assays set out in the Examples below. Other pharmacological methods may also be used to determine the efficacy of the compounds as antiproliferative, antibacterial, antifungal, and antiprotozoal agents. The compounds of the present invention may be used in combination with or as a substitution for treatments of the above conditions.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

A compound of the present invention may be administered in a therapeutically effective amount to a mammal such as a human. Therapeutically effective amounts of the compounds of the present invention may be used to treat, modulate, attenuate, reverse, or affect malaria or cell proliferation in a mammal. An "effective amount" is intended to mean that amount of an agent that is sufficient to treat, prevent, or inhibit malaria or cell proliferation. Thus, e.g., a "therapeutically effective amount" of a compound of the present invention, a prodrug, an active metabolite, or a salt thereof, is a quantity sufficient to, when administered to a mammal, treat, prevent, or inhibit diseases and disorders associated with cell proliferation, bacterial infections, fungal infections, or protozoal infections. The amount of a given compound of the present invention that will correspond to such an amount will vary depending upon factors such as the given drug or compound, the pharmaceutical formulation and route of administration, the type of disease or disorder, the degree of the disease or disorder, and the identity of the subject or host being treated, but can nevertheless be routinely determined by one skilled in the art. Also, as used herein, a "therapeutically effective amount" of a compound of the present invention is an amount which prevents, inhibits, suppresses, or reduces a given clinical condition in a subject as compared to a control. For example, a "therapeutically effective amount" of a compound of the present invention is an amount which prevents, inhibits, suppresses, or reduces malaria (as determined by clinical symptoms or the amount of *Plasmodium* organisms) in a subject as compared to a control. As defined herein, a therapeutically effective amount of a compound of the present invention may be readily determined by one of ordinary skill by routine methods known in the art.

For example, a therapeutically effective amount of a compound of the invention ranges from about 0.1 to about 1,000 mg/kg body weight, preferably about 0.1 to about 500 mg/kg body weight, and more preferably about 0.1 to about 100 mg/kg body weight. The skilled artisan will appreciate that certain factors may influence the dosage required to effectively treat a subject, including but not limited to the severity of the disease or disorder, previous treatments, the general health and/or age of the subject, and other diseases present.

Preferred topical concentrations include about 0.1% to about 10% of at least one compound of the present invention in a formulated salve. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the compound of the present invention may consist of a single administration, or alternatively comprise a series of applications. For example, a subject may be treated with a compound of the present invention at least once. However, the subject may treated with the compound from about one time per week to about once daily for a given treatment period. The length of the treatment period will depend on a variety of factors such as the severity of the disease or disorder, the concentration and activity of the compounds of the present invention, or a combination thereof. It will also be appreciated that the effective dosage of the compound used for treatment may increase or decrease over the course of a particular treatment. Changes in dosage may result and become apparent by standard diagnostic assays known in the art. In some instances chronic administration may be required. The compounds of the present invention may be administered before, during, after, or a combination thereof exposure to malaria or an agent that induces cell proliferation.

The pharmaceutical formulations of the invention comprise at least one compound of the present invention and may be prepared in a unit-dosage form appropriate for the desired mode of administration. The pharmaceutical formulations of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen compound of the present invention.

It will be appreciated that the actual dosages of the compounds used in the pharmaceutical formulations of this invention will vary according to the particular complex being used, the particular composition formulated, the mode of administration, and the particular site, host, and disease being treated. Optimal dosages for a given set of conditions may be ascertained by those skilled in the art using conventional dosage determination tests in view of the experimental data for a given compound. Administration of prodrugs may be dosed at weight levels that are chemically equivalent to the weight levels of the fully active forms.

The compounds of the present invention can be incorporated into pharmaceutical formulations suitable for administration. Pharmaceutical formulations of this invention comprise a therapeutically effective amount of at least one compound of the present invention, and an inert, pharmaceutically or cosmetically acceptable carrier or diluent. As used herein the language "pharmaceutically or cosmetically acceptable carrier" is intended to include any and all solvents, dispersion media, coatings, antibacterial and antifungal agents, isotonic and absorption delaying agents, and the like, compatible with pharmaceutical or cosmetic administration. The pharmaceutical or cosmetic carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically or cosmetically active substances is well known in the art.

Except insofar as any conventional media or agent is incompatible with the active compound, use thereof in the formulation is contemplated. Supplementary active compounds can also be incorporated into the formulations. Supplementary active compounds include antibiotics, antiprotozoal agents, antifungal agents, and antiproliferative agents known in the art, analgesics and other compounds commonly used to treat diseases and disorders associated with cell proliferation, bacterial infection, fungal infection, and protozoal infection.

Antibiotics include penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, ocolistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Antiprotozoal agents include chloroquine, doxycycline, mefloquine, metroni dazole, eplornithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like.

Antifungal agents include amphotericin B, fluconazole, itraconazole, ketoconazole, potassium iodide, flucytosine, and the like.

Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemicitabine, gemtuzumab-ozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, steroids, and the like.

A pharmaceutical or cosmetic formulation of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from 0-60% of the total volume.

The pharmaceutical formulation may also be in the form of a solution of a salt form of the active ingredient in an appropriate aqueous vehicle such as water or isotonic saline or dextrose solution.

The pharmaceutical formulations of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical formulations may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds of the present invention can be formulated readily by combining with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (compound), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum □horoi, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds and agents.

Pharmaceutical formulations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the formulations may take the form of tablets or lozenges formulated in conventional manner.

Oral formulations generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral formulations can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds of the present invention may be formulated for parenteral administration by injection, e.g., by bolus injection or continuous infusion. Formulations for injection may be presented in unit-dosage form, e.g., in ampoules or in multi-dose containers, with an added preservative. The formulations may take such forms as suspensions, solutions or emulsions in oily or aqueous vehicles, and may comprise formulatory agents such as suspending, stabilizing and/or dispersing agents.

Pharmaceutical formulations suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the formulation. Prolonged absorption of the injectable compositions can be brought about by including in the formulation an agent which delays absorption, for example, aluminum monostearate and gelatin.

Sterile injectable solutions can be prepared by incorporating a therapeutically effective amount of at least one compound of the present invention in an appropriate solvent with one or a combination of ingredients enumerated above, as required, followed by filtered sterilization. Generally, dispersions are prepared by incorporating the compound of the present invention into a sterile vehicle which comprises a basic dispersion medium and the required other ingredients from those enumerated above. In the case of sterile powders for the preparation of sterile injectable solutions, the preferred methods of preparation are vacuum drying and freezedrying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients or cosmetically acceptable carriers and additives include solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compounds of the present invention of the present invention may delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroids/retina and selera. The pharmaceutically acceptable ophthalmic vehicle may be an ointment, vegetable oil, or an encapsulating material. Compounds of the present invention may also be injected directly into the vitreous and aqueous humor.

Alternatively, compounds of the present invention may be in powder form for constitution with a suitable vehicle, e.g., sterile pyrogen-free water, before use. The compounds of the present invention may also be formulated in rectal compositions such as suppositories or retention enemas, e.g., comprising conventional suppository bases such as cocoa butter or other glycerides.

In addition to the formulations described above, compounds of the present invention may also be formulated as a depot preparation. Such long-acting formulations may be administered by implantation (for example, subcutaneously or intramuscularly) or by intramuscular injection. Thus, for example, the compounds of the present invention may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical formulations may be employed. Liposomes and emulsions are known examples of delivery vehicles or carriers for hydrophobic drugs and cosmetics. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical formulations also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, and the like. Salts tend to be more soluble in aqueous or other protonic solvents than are the corresponding free-base forms.

In one embodiment, the compounds of the present invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

It is especially advantageous to formulate oral or parenteral formulations in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The following Examples are intended to illustrate, but not to limit the present invention.

EXAMPLE 1

Antimalarial Activity Assay

The tryptanthrin compounds were examined for $IC_{50}$ values against either the *P. falciparum* W2 (Indochina) or D6 (Sierra Leone) clones in vitro. See U.S. Pat. No. 6,284,772, which is herein incorporated by reference. The in vitro assays were conducted by using the semiautomated microdilution technique of Desjardins, et al. (1979) Antimicrob. Agents Chemther. 16:710-718 and the [$^3$H]hypoxanthine incorporation techniques of Chulay et al. (1983) Exp. Parasitol. 55:138-146, both of which are herein incorporated by reference. The W2 clone is susceptible to mefloquine but resistant to chloroquine, sulfadoxine, pyrimethamine, and quinine. The D6 clone is resistant to mefloquine but susceptible to chloroquine, sulfadoxine, pyrimethamine, and quinine. The clones were derived by direct visualization and micromanipulation from the patient isolates.

Test tryptanthrin compounds were initially dissolved in DMSO and diluted 400-fold in RPMI 1640 culture medium supplemented with 25 mM Hepes, 32 mM $NaHCO_3$ and 10% Albumax I (GIBCO BRL, Grand Island, N.Y.). These solutions were subsequently serially diluted 2-fold with a Biomek 1000 (Beckman, Fullerton, Calif.) over 11 different concentrations. The parasites were exposed to serial dilutions of each compound for 48 hours and incubated at 37° C. with 5% $O_2$, 5% $CO_2$, and 90% $N_2$ prior to the addition of [$^3$H]hypoxanthine. After a further incubation of 18 hours, parasite DNA was harvested from each microtiter well using a Packard Filtermate 196 Harvester (Meriden, Conn.) onto glass filters. Uptake of [$^3$H]hypoxanthine was measured with a Packard topcount scintillation counter. Concentration-response data were analyzed by a nonlinear regression logistic dose-response model and the $IC_{50}$ values (50% inhibitory concentrations) for each compound were determined.

Based on $IC_{50}$ data, tryptanthrin compounds (II) having subtle substitutions that replace H at $R^1$ through $R^4$ of tryptanthrin (I) provide substantial effects on antimalarial activity. Tryptanthrin compounds (II) wherein Z is N or $R^3$ or $R^4$ are F provides antimalarial activities that are greater than tryptanthrin (I). Different substitutents for $R^5$ through $R^8$ do not significantly affect antimalarial activity. Tryptanthrin compounds wherein $R^6$ is F exhibit the greatest antimalarial activity. Alterations in the core of tryptanthrin (the nitrogen and oxygens in the center of the molecule) make tryptanthrin compounds inactive, except when the double bonds are maintained.

Tryptanthrin compounds possessing one or more carbonyl, amine, alcohol or sulfone substitutents were obtained and tested. See Example 2 of U.S. Pat. No. 6,284,772, which is herein incorporated by reference.

EXAMPLE 2

3D-QSAR & Pharmacophore Generation

The molecular modeling software, CATALYST® 4.6 software (Accelrys Inc., San Diego, Calif.) was used to construct a three-dimensional QSAR pharmacophore model for the antimalarial activities exhibited by tryptanthrin compounds. A training set of 17 structurally diverse indolo(2,1-b)quinazoline-6,12-dione analogues having a broad range of antimalarial activities was used to construct the pharmacophore model.

The pharmacophore model was developed by placing suitable constraints on the number of available features such as, aromatic hydrophobic or aliphatic hydrophobic interactions, hydrogen bond donors, hydrogen bond acceptors, hydrogen bond acceptors (lipid), and ring aromatic sites to describe the antimalarial activity of the tryptanthrin compounds. Earlier reported quantum chemical calculations of the stereoelectronic properties of these compounds provided the foundation for selection of these physico-chemical features. See Bhattacharjee, A. K., et al. (2002) Bioorg. Med. Chem. 10:1979-1989.

During this pharmacophore or hypothesis generation, the molecules were mapped to the features with their predetermined conformations generated earlier using the "fast fit" techniques in the CATALYST®. The procedure resulted in the generation of 10 alternative hypotheses for antimalarial activity of the compounds and appeared to perform quite well for the training set. The correlation coefficients were found to be between 0.89 to 0.87 for six of the ten models, and the RMS values ranged between 1.47 and 1.71. The total costs of the hypotheses varied over a narrow range between 88 to 95 bits. The difference between the fixed cost and the null cost is 77.0. Thus, both of the differences, the total cost of the first and the tenth hypothesis, and the fixed cost and the null cost were found to be within the acceptable range recommended in the cost analysis of the CATALYST® procedure.

EXAMPLE 3

Cross Validation of Pharmacophore Model

The pharmacophore model was cross-validated by generating a test set of 15 different indolo(2,1-b)quinazoline-6, 12-dione analogues (Table 1). The test set compounds were screened for antimalarial activity against D6 and W2 clones of P. falciparum identical to the original training set in viva. This test set was not used for automatic generation of the pharmacophore and thus, the test set of the tryptanthrin compounds were not used in determining the features of the pharmacophore generated from the original training set.

Regression analysis was performed by mapping this test set onto the features of the pharmacophore and showed remarkable consistency of the model (R=0.92). Regression information is used to estimate activity of the training set of the compounds as well as to estimate the unknown compounds. The greater is the fit of the pharmacophore with the compound more likely the compound to be active. The regression for both the training set and the test set is calculated by the following equation:

$$-log(\text{activity})_{Est} = \text{Fit} * \text{Slope} + Y \text{ intercept}$$

See Catalyst® Tutorials, Release 4.5, August 1999, Accelrys Scientific Support. 9685 Scranton Road, San Diego, Calif. 92121-3752, which is herein incorporated by reference.

EXAMPLE 4

Validation of Pharmacophore Model

The validity of the pharmacophore model to other commonly used antimalarial drugs was examined. The pharmacophore features were mapped onto a series of eight antimalarial drugs, quinine, chloroquine, mefloquine, primaquine, hydroxychloroquine, pyrimethamine, sulfadoxine, and doxycycline, which are currently used in the United States. See Vroman, J. A. et al. (1999) Curr. Pharm. Design 5:101-138, which is herein incorporated by reference.

EXAMPLE 5

Hemin Binding Activity Assay

The hemin binding affinity for a series of tryptanthrin compounds with functional groups at the 8-position with different electron donating/withdrawing characteristics corresponding with the pharmacophore model of the present invention was determined using $^1$H NMR. The binding interaction was measured as a function of the induced up-field shift in the chemical shift as a function of increasing hemin concentration. $^1$H spectra of each analog with an increasing concentration of hemin were collected and analyzed for the effect of the pseudocontact shifts.

Samples were prepared for the NMR studies using the tryptanthrin compounds listed in Table 5 in 500 µl of DMSO-$d_6$. To each sample, a 100 or 200 µl aliquot of a known concentration of hemin dissolved in 1.0 ml of DMSO-d6 was added. The concentrations of the tryptanthrin compounds compounds ranged from 3.0 to 8.0 mg per 500 µl of DMSO. A corresponding solution of hemin in DMSO was prepared to maintain a molar ratio of tryptanthrin compounds to hemin in the range of 1:1.0 to 1:1.5.

All $^1$H NMR data was collected using a Bruker Avance-600 spectrometer using methods known in the art. See e.g. Wang, J., et al. (2001) J. Am. Chem. Soc. 123:8080-8088, which is herein incorporated by reference. The proton spectra were collected at 300 K, using a spectral width of 9090.9 Hz. All spectra were acquired with 64k data points in F2. All chemical shifts were referenced internally to TMS (0.00 ppm). The spectra were processed using XWINNMR (Bruker BioSpin Corporation, Billerica, Mass.) on a Silicon Graphics O2 workstation (Silicon Graphics, Mountain View, Calif.). Each data set was multiplied by a Gaussain window function with 0.3 Hz line broadening in each dimension before transformation.

In order to provide a theoretical model for the NMR observations, the cation binding affinities of the D ring for the four tryptanthrin compounds in Table 6 using sodium ion as the cationic probe were calculated.

Ab initio quantum chemical method at restricted HF level with 6-31G doubly polarized basis set was used for complete optimization of geometry of the sodium-tryptanthrin complexes and the uncomplexed tryptanthrin molecules. The calculations were performed using RHF/6-31G basis set of quantum chemical theory as implemented in the Gaussian 94 package (Gaussian 94, Revision A.1 (1995) Gaussian Inc., Pittsburgh Pa.) on the binding of sodium cation to the pi-face of the aromatic "D" ring of the tryptanthrin compounds. Sodium ion was chosen as the probe cation as hemin (implicitly $Fe^{++}$) could not be tackled at this level of theory. Complete optimization of geometry of each of the complexes was carried out using the above basis set. Similar calculations were performed using the geometry of the uncomplexed tryptanthrin compounds and sodium ion separately as described in similar earlier studies. See Bhattacharjee, A. K. (2000) J. Mol. Struct. (Theochem) 529:193-201, which is herein incorporated by reference. The HF/6-31G** basis set has been documented as adequate enough for such studies and substantially higher basis sets produce similar trends. See Mecozzi, S. et al. (1996) J. Am. Chem. Soc. 118:2307, which is herein incorporated by reference. Electrostatic potential profiles at a constant −1.0 kcal/mol were generated to provide a profile beyond the van der Waals surface (about 1.4 to about 1.5 Å away) encountered by an approaching molecule.

EXAMPLE 6

Pharmacophore Compound Screening and In Vivo Testing

A. Database Pharmacophore Compound Screening

The Chemical Information System database of the Division of Experimental Therapeutics, WRAIR is a database of more than 245,000 proprietary compounds. By using the catDB utility program of the CATALYST®, we have transformed it into a multi-conformer based 3D database. The database searching protocol in the CATALYST® involves a rapid 3D screening process followed by a rigorous atom-by-atom mapping in which a fairly comprehensive set of features including the chemical features of the pharmacophore are considered. In addition to the traditional pharmacophore based searching, 3D shape similarity and partial match searching are also performed. See Y. Kurogi and O. F. Gunner (2001) Current Medicinal Chemistry 8:1035-1055, which is herein incorporated by reference.

The following six compounds were selected to be screened for in vivo activity:

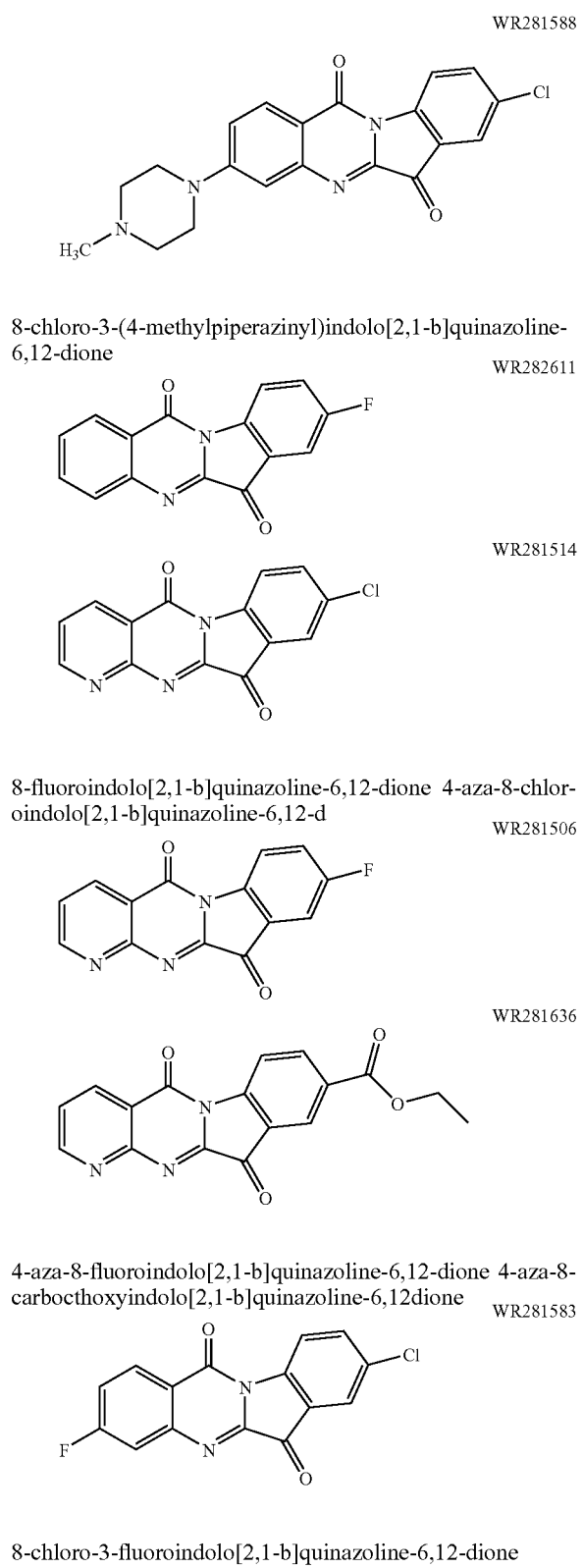

8-chloro-3-(4-methylpiperazinyl)indolo[2,1-b]quinazoline-6,12-dione 8-fluoroindolo[2,1-b]quinazoline-6,12-dione   4-aza-8-chloroindolo[2,1-b]quinazoline-6,12-d 4-aza-8-fluoroindolo[2,1-b]quinazoline-6,12-dione  4-aza-8-carbocthoxyindolo[2,1-b]quinazoline-6,12dione 8-chloro-3-fluoroindolo[2,1-b]quinazoline-6,12-dione B. In Vivo Testing (Thompson Test)

The in vivo efficacy of the compounds of the present invention alone or in combination with an adjuvant can be determined in a modified Thompson test. This test measures the survivability of mice and parasitemia clearance following administration of the compound or composition of the invention on days 3-5 post infection. In brief, 5×105 malaria parasites of one or more of the four described strains are inoculated intraperitoneally to female mice that weight approximately 24-30 g. Each compound was dissolved in 5% sodium bicarbonate, and was administered p.o. twice daily from day 3 to day 5 postinfection. Total dosage of the compounds of the invention is 0.001 to 1000 mg/kg. The percent suppression of parasitemia in the treated mice compared to untreated controls is determined for each test compound. Survival of mice to day 60 post infection is considered a cure. Compounds are considered active when the survival time of the treated mice is greater than twice the control mice.

The test of the six compounds identified above were conducted by subcutaneous dosing in peanut oil. Formulated in peanut oil and injected s.c. (N=8) at various doses up to 190 mg/kg. No toxicity was noted for up to 190 mg/kg maximum dosage. WR$^{282611}$ was exhibited activity at max. dosage (190 mg/kg). Although parasites were not cleared, the survival of infected mice doubled that of the control. Life expectancy was 12-14 days compared to 6-7 days in the control (parasitized, untreated).

EXAMPLE 7

Quantum Chemical Procedure

Computational calculations at the semi-empirical AM1 level were performed using SPARTAN version 5.0 running on a Silicon Graphics Octane workstation to determine the chemical descriptors.

A fairly good correlation is observed between antimalarial activity and selected calculated electronic properties such as LUMO (lowest unoccupied molecular orbital) energy and redox potentials.

Conformation search calculations using the "systematic search" technique via the single-point AMI method of SPARTAN (SPARTAN version 5.1, Wavefunction, Inc., 18401 Von Karman Ave., #370, Irvine, Calif. 92715) was used to generate different conformers for each of the molecules. The minimum energy conformer with highest abundance (a Boltzman population density greater than 70.0%) was chosen for full geometry optimization using the AMI algorithm. See Dewar, M. J. S., et al. (1985) J. Am. Chem. Soc. 107:3902-3909. Molecular electronic properties such as molecular orbital energies, lowest unoccupied molecular orbital energy (LUMO) and highest occupied orbital energy (HOMO) and electrostatic potentials, atomic charges, and structural parameters were calculated on the optimized geometry of each of the molecules using the algorithm in SPARTAN.

EXAMPLE 8

Cyclic Voltammetry

The redox potentials associated with electron transfer to the oxygen atoms in compounds was measured. Experiments were performed on a CV-50W Voltammetric analyzer with a C2 cell stand (Bioanalytical systems, West Lafayette Ind.).

The carbonyl group of the 5-member C ring and the ability of this oxygen atom to participate in electron transfer appears to be crucial for activity.

Cyclic voltammetry experiments were performed on a CV-50W Voltammetric analyzer with a C2 cell stand (Bioanalytical systems, West Lafayette Ind.). A glassy carbon working, an Ag—AgCl reference electrode and a Pt auxiliary electrode were used in a 5 ml glass cell. All samples were dissolved in dry acetonitrile (Aldrich, St. Louis, Mo.) with 0.1 M tetrabutylammonium hexafluorophosphate (Aldrich, St. Louis, Mo.) as the supporting electrolyte. Each analog was prepared at a concentration of 1 mM and was degassed with nitrogen for 5 minutes prior to analysis. Samples were run at several scan rates ranging from 20 to 1000 mV/s. See Smyth, M. R., and Vos, J. G. *Analytical Voltammetry*; Elsevier: New York, 1992; Chapter 1, which is herein incorporated by reference.

EXAMPLE 9

Vibrational Spectroscopy

The stretching frequencies of the two carbonyl moieties were measured and the vibrations were correlated to measured and calculated electrostatic properties. Experiments were performed on an BIO-RAD FTS3000 FTIR spectrophotometer fitted with an ATR (Sensor Technologies, Danbury, Conn.).

Vibrational spectroscopy indicates the stretching frequency of the 5-member ring carbonyl is intimately linked to the measured redox potentials and calculated LUMO energy which supports the addition of a proton during the first redox step (−0.75 V). The 6-member ring carbonyl indicates no such correlation.

Figure 13A:
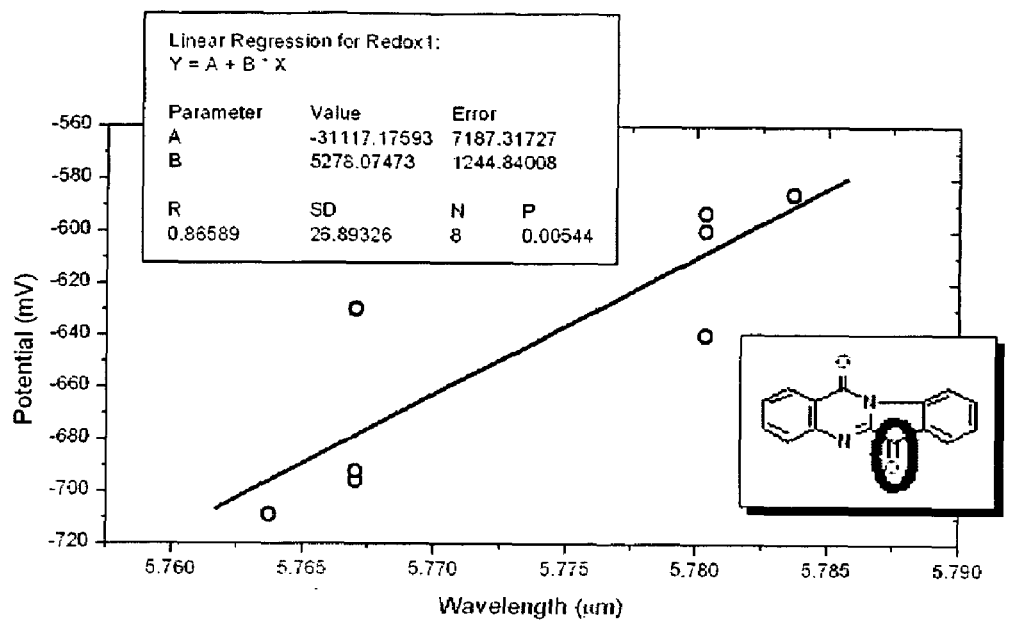
FIGS. 13A-13F show correlation plots of both redox potentials and calculated LUMO energies versus IR stretching frequency of indolo[2,1-b]quinazoline-6,12-dione for both the C6 carbonyl and the C12 carbonyl.
Figure 13B:
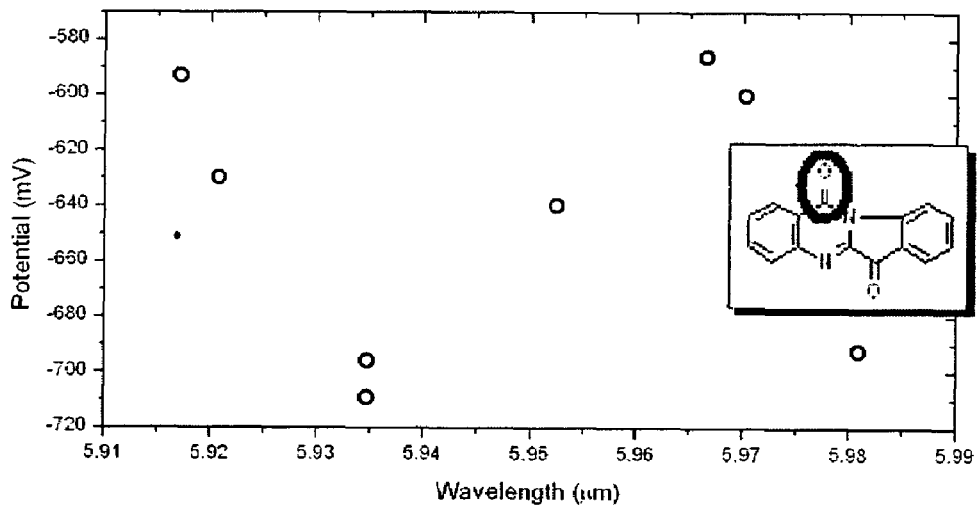
Figure 13C:
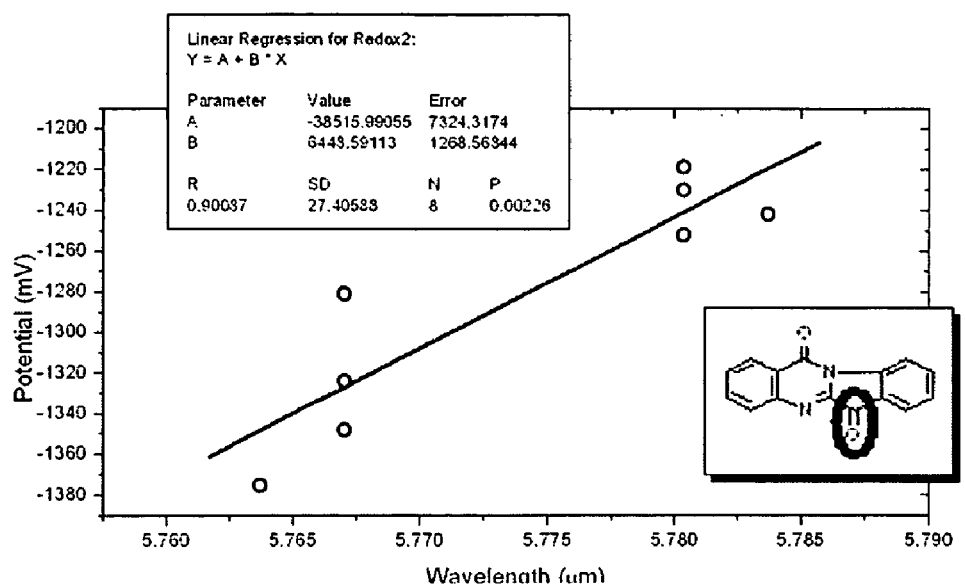
Figure 13D:
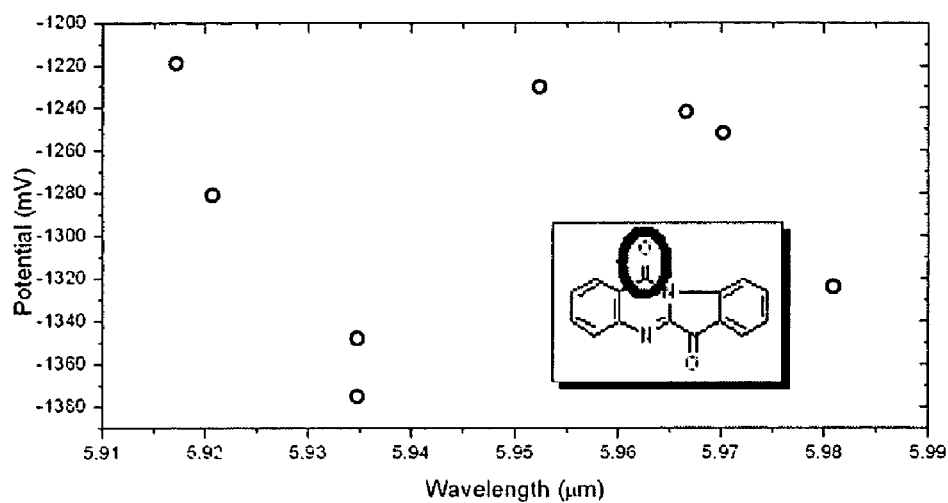
Figure 13E:
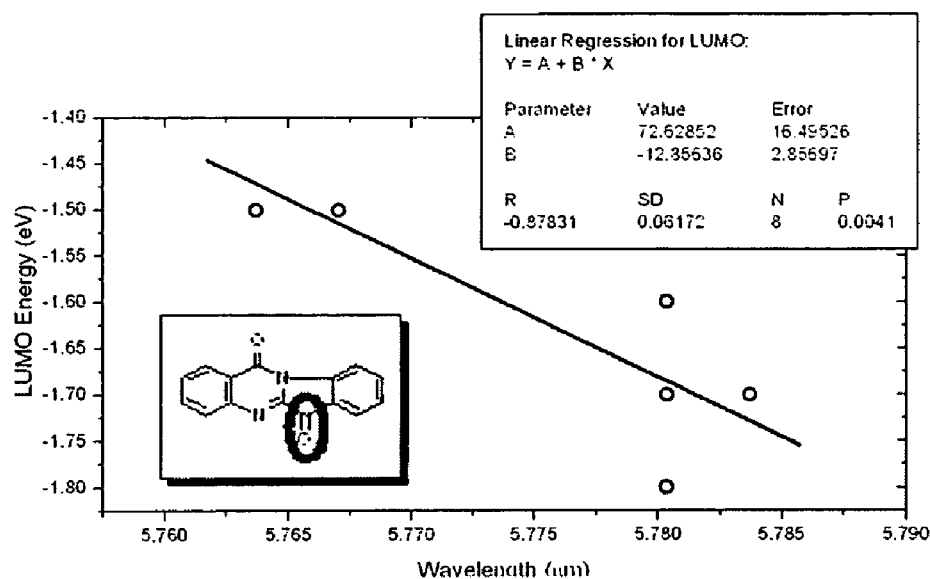
Figure 13F:
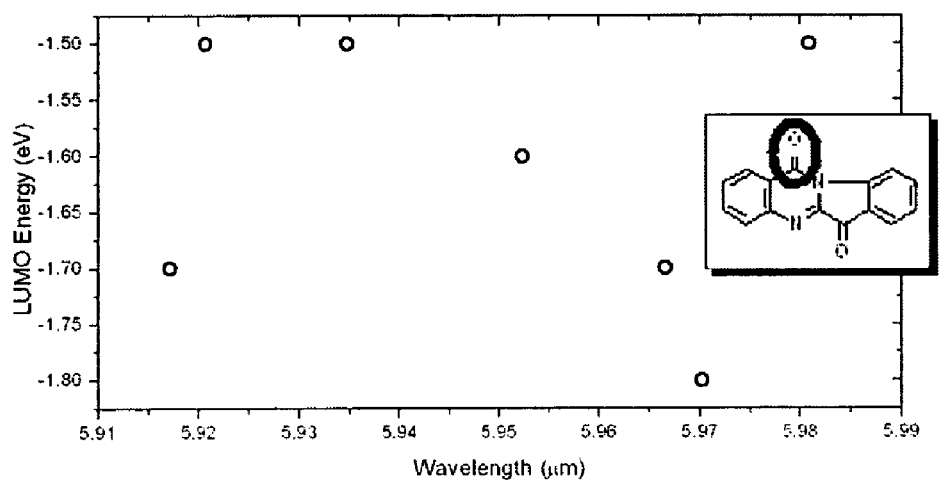

Vibrational spectroscopy experiments were performed on an BIO-RAD FTS3000 FTIR spectrophotometer fitted with an ATR (Sensor Technologies, Danbury, Conn.). Tryptanthrin compounds were taken up in a minimal volume of acetonitrile (HPLC grade, Aldrich, St. Louis, Mo.) and transferred to the surface of the ATR. The solvent was allowed to evaporate and solid-state FTIR spectra were collected as an average of 64 to 128 scans. See FIG. 13. FIGS. 13A and 13B show the first redox potential. FIGS. 13C and 13D show the second redox potential. FIGS. 13E and 13F show the lowest unoccupied molecular orbital (LUMO) energy. FIGS. 13A, 13C, and 13E show the C6 carbonyl and FIGS. 13B, 13D, and 13F show the C12 carbonyl. FIGS. 13A and 13B show a direct correlation of the vibrational (IR) frequency of the C6 carbonyl with the $1^{st}$ redox potential, $2^{nd}$ redox potential and the LUMO energy. FIGS. 13C and 13D show no correlation of the vibrational (IR) frequency of the C12 carbonyl with the $1^{st}$ redox potential, $2^{nd}$ redox potential and the LUMO energy.

The following eight compounds were tested:

WR281635

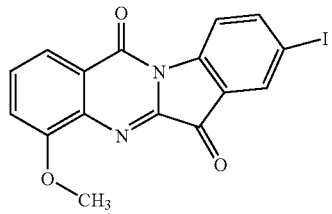

8-iodo-4-methoxyindolo[2,1-b]quinazoline-6,12-dione,

WR281588

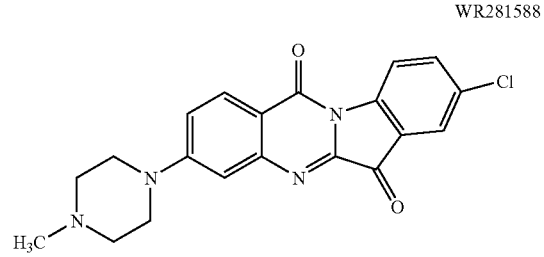

8-Chloro-3-(4-methyl-piperazin-1-yl)-indolo[2,1-b]quinazoline-6,12-dione,

WR281591

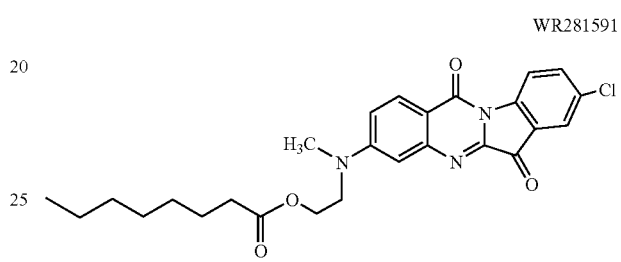

Octanoic acid 2-[(8-chloro-6,12-dioxo-6,12-dihydro-indolo[2,1-b]quinazolin-3-yl)-netliyl-amino]-eth,

WR281523

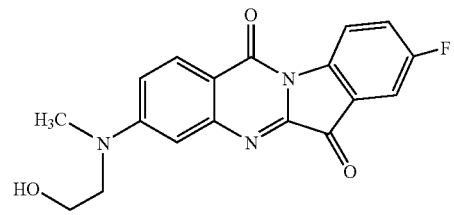

8-Fluoro-3-[(2-hydroxy-ethyl)-methyl-amino]-indolo[2,1-b]quinazoline-6,12-dione,

WR281631

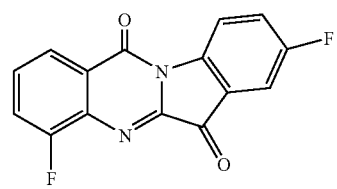

WR281583

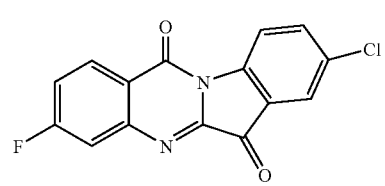

4,8-difluoroindolo[2,1-b]quinazoline-6,12-dione   8-chloro-3-fluoroindolo[2,1-b]quinazoline-6,12-dione,

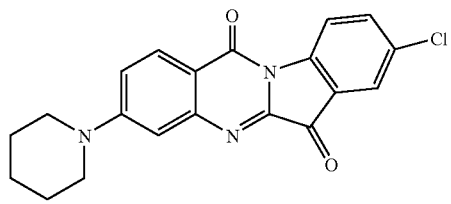

8-chloro-3-piperidin-1-ylindolo[2,1-b]quinazoline-6,12-dione, and

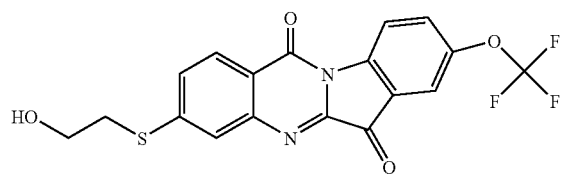

3-(2-Hydroxy-ethylsulfanyl)-8-trifluoromethoxy-indolo[2,1-b]quinazoline-6,12-dione.

The results are provided in the following Table 7:

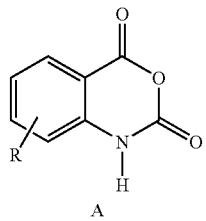

The isatoic anhydride A formed was reacted with isatins to form tryptanthrin compound B using a modification of Bergman's procedure. See Bergman, J. et al. (1985) Tetrahedron 41 2879-2883, which is here in incorporated by reference.

Synthesis of Tryptanthrin B

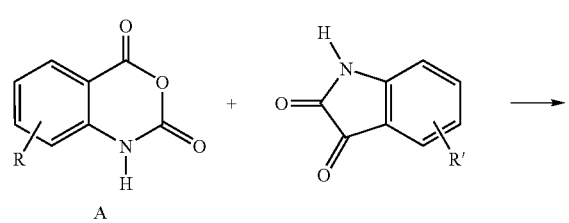

TABLE 7

| | | | Physico-chemical Parameters | | | | | FTIR Vibrations | | | |
|---|---|---|---|---|---|---|---|---|---|---|---|
| Tryptanthrin | W-2 | D-6 | Dipole | HOMO | LUMO | Redox1 | Redox 2 | C6 (cm-1) | C12 (cm-1) | C6 (um) | C12 (um) |
| WR281631 | 1.584 | 2.569 | 3.45 | −9.2 | −1.7 | −593 | −1219 | 1730 | 1690 | 5.78035 | 5.91716 |
| WR281635 | 35.649 | 95.331 | 1.31 | −9 | −1.6 | −640 | −1230 | 1730 | 1680 | 5.78035 | 5.95238 |
| WR281583 | 4.741 | 6.767 | 2.2 | −9.4 | −1.7 | −586 | −1242 | 1729 | 1676 | 5.78369 | 5.96659 |
| WR281647 | 58.1 | 97.106 | 3.58 | −8.9 | −1.5 | −696 | −1348 | 1734 | 1685 | 5.76701 | 5.93472 |
| WR281588 | 4.272 | 10.461 | 2.9 | −8.9 | −1.5 | −692 | −1324 | 1734 | 1672 | 5.76701 | 5.98086 |
| WR281523 | 2.455 | 4.121 | 3.3 | −8.9 | −1.5 | −630 | −1281 | 1734 | 1689 | 5.76701 | 5.92066 |
| WR281591 | 36.831 | 70.142 | 4.3 | −8.9 | −1.5 | −709 | −1375 | 1735 | 1685 | 5.76369 | 5.93472 |
| WR281525 | 1.252 | 2.31 | 3.7 | −8.9 | −1.8 | −600 | −1252 | 1730 | 1675 | 5.78035 | 5.97015 |

EXAMPLE 10

Synthesis of Trypthanthrin Compound C

Tryptanthrin compound C, was synthesized as follows. 2-aminobenzoic acid analogs were reacted with triphosgene to synthesize the corresponding isatoic anhydride A.

Synthesis of Isatoic Anhydride A

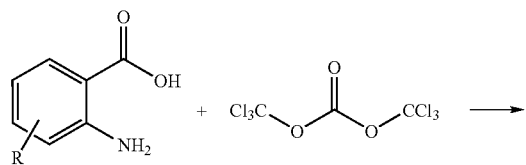

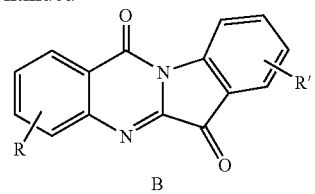

Specifically, an oven-dried 50 ml round-bottom flask was cooled with magnetic stirrer and air condenser under nitrogen gas. 1-methylpiperidine (3 drops, about 1.5 mmol, about 0.3 eq) was added dropwise. Diisopropylcarbodiimide (0.5 ml, 3.2 mmol, 0.64 eq) was then added. After 5 minutes, anhydrous pyridine (about 6 ml) was added. The mixture was placed in an oil bath at 70° C. for 30 minutes. Isatin (5 mmol, 1.0 eq) and isatoic anhydride (5 mmol, 1.0 eq) were sequentially added and the temperature was maintained at 70° C. for 30 minutes. After about 20 minutes all reagents were dissolved and then the temperature was raised to 80° C.

for 10 minutes. Then the temperature was raised to 95° C. for 40 minutes or until a solid product was observed. The solid product was cooled to room temperature and filtered through a coarse-fritted filter funnel under vacuum. The solid product was washed with methanol several times and then dried under vacuum filtration.

Tryptanthrin compound C is formed using tryptanthrin compound B and various bases according to Scheme 3. The identity of tryptanthrin compound C was supported by 1H and 13C NMR spectroscopy, LC/MS, and melting point.

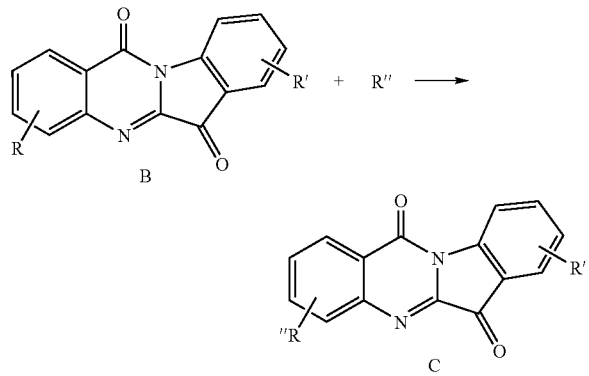

Scheme 3: Derivatization of Tryptanthrin B into Tryptanthrin C

Unlike prior art tryptanthrin compounds, tryptanthrin compound C exhibits solubility in chloroform in excess of 5 mg/ml. Previous tryptanthrin compounds typically have limited solubility even in dimethyl sulfoxide (4-8 mg/ml) and have no appreciable (<0.1 mg/ml) solubility in hexanes, ethyl acetate, ether, toluene, dichloromethane, chloroform, methanol, ethanol, water, or acetone.

All chemicals were obtained from Aldrich chemical company and used without further purification. Glassware was oven dried for 0.5 hour prior to use. Reactions were carried under an inert nitrogen atmosphere.

During the duration of the synthetic process, a UV/VIS lamp was used to observe TLC plates. A 600 MHz NMR spectrometer was used to confirm the structures of various compounds involved in the synthesis. GC/MS and LC/MS were carried out both as an effective way to monitor reaction progress and to confirm or disconfirm the presence of a desired product. Where possible, melting points of products were compared with literature values.

EXAMPLE 11

Solubility and Bioavailability Assays

A. Solubility

The solubility of DN49 (WR288510) was tested in various solvents to determine the properties encouraging solubility. Initial results indicated that an N—H, O or aromatic group encourage solubility. An N—H group on an aromatic compound might be forming a complex with tryptanthrin.

In the following experiments, solubility was defined as achieving 25 mg/ml. (200 mM) concentration in a solvent. The temperature is a close approximation to the temperature required to achieve solubility. Color is the color of the solution; DN49 is a yellow compound and colors other than yellow indicate close interaction between solvent and solute. Precipitate is whether or not DN49 precipitated out upon cooling to room temperature. These results shown in Table 8 indicate that solubility of tryptanthrins in a given solvent is vastly improved by N—H, OH, and (hetero)aromatic functions.

TABLE 8

| Solvent | Soluble | Temperature | Color | Precipitate |
|---|---|---|---|---|
| Pyrrole | Yes | 0 | Red | No |
| Indole | Yes | 53 | Red | Solidified |
| Pyridine | Yes | 80 | Yellow | Yes |
| Isoquinoline | Yes | 60-70 | Yellow | Solidified |
| Nitrobenzene | Yes | 80 | Yellow | Yes |
| Dimethylsufoxide | No | Na | Yellow | Na |
| Aniline | Yes | 18 | Red | No |
| N-methylbenzylamine | Yes | 18 | Green | No |
| Piperidine | Yes | 18 | Green | No |
| N-methylpiperidine | No | N/A | Yellow | N/A |
| Pyrrolidine | Yes | 18 | Green | No |
| Diethylamine | No | N/A | Green | N/A |
| Triethylamine | No | N/A | Yellow | N/A |
| Toluene | No | N/A | Yellow | N/A |
| Phenol | Yes | 47 | Yellow | solidified |
| Benzyly alcohol | Yes | 30 | Yellow | No |
| Benzoic acid | Yes | 50-60 | Yellow | Yes |
| 3,4-dihydro-2H-pyran | No | N/A | Yellow | N/A |
| Tetrahydrofuran | No | N/A | Yellow | N/A |
| 1,4-dioxane | Yes | 80-90 | Yellow | yes |

B. Bioavailability

Fifty-six (56) female mice (7 groups of 8 mice each) were used to test the bioavailability and efficacy of DN49. On day 0, each mouse in groups 1 to 7 was inoculated intraperitoneally with 0.1 ml, $1.0 \times 10^6$ P. berghei P-line infected red blood cell from donor mice diluted in PBS.

DN49 was a yellow powder and dissolved completely in hot DMSO. The hot DMSO solution was then diluted 1:10 in PBS. The characteristics of DN49 at each dosage are provided in Table 9:

TABLE 9

| Group | Drug # | Dosage | Vehicle | Solubility | Supernatant | Sediment |
|---|---|---|---|---|---|---|
| 1 | None | None | PBS | N/A | Clear, colorless | None |
| 2 | WR288510 | 2.5 | Hot DMSO and further diluted in PBS | Partial | Clear yellow (+1) with small amount of suspending particles | Light yellow, fine particles (+3) |
| 3 | | 1.25 | | | | Light yellow, fine particles (+2) |
| 4 | | 0.625 | | | | Light yellow, fine particles (+1) |
| 5 | | 30 | | | | Light yellow, fine particles (+2) |

TABLE 9-continued

| Group | Drug # | Dosage | Vehicle | Solubility | Supernatant | Sediment |
| --- | --- | --- | --- | --- | --- | --- |
| 6 | | 15 | | | | Light yellow, fine particles (+1) |
| 7 | | 7.5 | | | | Light yellow, fine particles (+1) |

On days 3 to 5, 0.2 ml of the three dosages at 2.5, 1.25, 0.625 mg/kg of DN49 were administered intravenously by a 29G, 0.5-inch needle (Groups 2 to 4). In addition, 0.2 ml of the three dosages at 30, 15, 7.5 mg/kg of DN49 were administered orally by a 20G, 2.5-inch needle (Groups 5 to 7). Drug administrations were performed once daily for 3 days. Group 1 served as vehicle control, and PBS was administered orally. There were no acute toxicity or other deaths prior to day 6.

Necropsies were performed in all dead animals. All mice showed typical gross lesions such as gray swollen liver, dark spleen, and pale emaciated carcass (similar to control mice of Group 1), which indicated fatal malaria infection.

On day 3, all 56 mice were positive between 0.1 to 1.1%. On day 3, all 56 mice were positive between 0.1 to 1.1%. All infected control mice (Group 1) showed positive parasitemia on day 3 and high parasite count on day 6 (mean parasitemia 55.93%). The mice died between days 6 to 8.

For the mice that received IV DN49 (Groups 2 to 4):

Group 2 mice died between days 6 to 10 (2, 3, 2 and 1 mice on days 6, 8, 9 and 10, respectively). They showed high parasitemia on day 6 (mean 54.75%). Gross necropsy lesions confirmed that mice died from malaria.

Group 3 mice died between days 6 to 8. They showed high parasitemia on day 6 (mean 55.75%). Gross necropsy lesions confirmed that mice died from malaria.

Group 4 mice died between days 6 to 9. They showed high parasitemia on day 6 (mean 61.18%). Gross necropsy lesions confirmed that mice died from malaria.

For the mice that received oral DN49 (Groups 5 to 7):

Group 5 mice died between days 6 to 10 (1, 4, 2 and 1 mice on days 6, 7, 8 and 10, respectively). They showed high parasitemia on day 6 (mean 56.11%). Gross necropsy lesions confirmed that mice died from malaria.

Group 6 and 7 mice died between days 6 to 9. They showed high parasitemia on day 6 (mean 54.26 and 64.23%, respectively). Gross necropsy lesions confirmed that mice died from malaria.

In summary, DN49 extended the life of mice for 2 days at 2.5 mg/kg intravenously or at 30 mg/kg orally when given once daily at study days 3 to 5. At lower dosages, DN49 exhibited no significant activity. Toxic effects of the DN49 were not observed at the dosages given in this experiment.

C. Further Solubility Experiments

After determining that heterocycles and hydroxy or amine substituted aromatics dissolve tryptanthrin compounds, the following was conducted to determine if once dissolved the compounds would remain in solution in aqueous environments. To this end 10 mg of DN49 was dissolved in 1.0 ml of piperidine to obtain a green solution. This solution was then added dropwise to 2.0 ml of deionized water without precipitation of the compound. The solution was placed in a chemical fume hood so that the piperidine could evaporate slowly. After a week, the piperidine had evaporated and the resulting solution had no solid in the aqueous environment and had turned from the green color of the piperidne complex back to the yellow color of uncomplexed DN49 solutions.

Further experiments were conducted with other solvents as follow:

A 200 mM (25 mg/mL) green stock solution of DN49 in 1-(3-aminopropyl)imidazole was formed. To 1.95 ml of a given solvent listed below, 50 microliter of the stock solution was added and the resulting solution was vortexed for a second to ensure rapid mixing; this provided a 5 mM solution. The results by solvent follow:

1. Chloroform: Solution goes from green to yellow in less than 30 minutes; no solid after more than three months at ambient conditions.
2. Methanol: Solution goes from green to yellow between 5 and 12 hours after mixing; no solid.
3. 1,4-dioxane: Solution goes from green to yellow in approximately 1 hour; no solid.
4. Deionized water: Solution goes from pink to colorless over the course of several days; no solid.
5. Acetonitrile: Solution goes from green to yellow in about 3 hours; no solid.
6. 0.1 M aqueous citric acid: Solution stays green indefinitely; has green solid fall out of solution after about 12 hours.
7. 10% aqueous sodium bicarbonate: Solution goes from green to yellow between 5 and 12 hours; green precipitate after 8 hours.

These results indicate (by the color change in the organic solvents) that the complex between the DN49 and 1-(3-aminopropyl)imidazole causing dissolution of DN49 falls apart with time, but this does not force precipitation of DN49 at a 5 mM concentration. Furthermore, this holds true in water. In summary, preventing intermolecular stacking of these molecules allows for dissolution, and that once dissolved the tryptanthrin compounds do not precipitate out at 5 mM concentration in water. Thus, attachment of groups to tryptanthrins which disrupt these intermolecular forces, such as presented in this invention, improve the solubility and/or bioavailability of the compounds to a pharmaceutically useful level not previously attainable.

EXAMPLE 12

Antibacterial Assay

The activity of the compounds of the present invention against *Mycobacterium tuberculosis* may be determined using the assays known in the art such as that described in U.S. Pat. No. 5,441,955, which is herein incorporated by reference, or the following assays that are conducted by the National Institute of Allergy and Infectious Diseases (NIAID) supports a TB drug acquisition and screening program, the TAACF.

1. In Vitro Evaluation of Anti-*Mycobacterium tuberculosis* Activity

To determine the percent inhibition the following assay may be conducted. Primary screening is conducted at 6.25 µg/ml (or the molar equivalent of highest molecular weight compound in a given series of congeners) against *Mycobacterium tuberculosis* $H_{37}Rv$ (ATCC 27294) in BACTEC 12B medium using the Microplate Alamar Blue Assay (MABA). See Collins, L. and S. G. Franzblau. 1997. Microplate alamar blue assay versus BACTEC 460 system for high-throughput screening of compounds against *Mycobacterium tuberculosis* and *Mycobacterium avium*. Antimicrob Agents Chemother 41:1004-9, which is herein incorporated by reference.

Compounds exhibiting fluorescence are tested in the BACTEC 460-radiometric system. Compounds effecting less than about 90% inhibition in the primary screen (MIC>6.25 µg/ml) are not generally evaluated further. Minimum compound requirements: 1.0 mg.

2. Minimum Inhibitory Concentration (MIC)

Compounds that demonstrate at least about 90% inhibition in the primary screen are re-tested at lower concentrations against *M. tuberculosis* H37Rv to determine the actual minimum inhibitory concentration (MIC) in the MABA. The MIC is defined as the lowest concentration effecting a reduction in fluorescence of 90% relative to controls.

3. Cytotoxicity

Concurrent with the determination of MICs, compounds are tested for cytotoxicity ($IC_{50}$) in VERO cells at concentrations less than or equal to 62.5 µg/ml or 10 times the MIC for *M. tuberculosis* $H_{37}Rv$. After 72 hours exposure, viability was assessed on the basis of cellular conversion of MTT into a formazan product using the Promega CellTiter 96 Non-radioactive Cell Proliferation Assay.

4. In Vivo Evaluation of Anti-*Mycobacterium tuberculosis* Activity

The in vivo activity of the compounds of the present invention may be determined using conventional methods known in the art. For example, activity against *Mycobacterium avium* (ATCC 25291) and the maxium tolerated dose (MTD) may be determined as follows:

C57BL/6 female mice (6-8 weeks in age) are administered a one-time dose (oral gavage) of the compound at concentrations of 100, 300 or 1000 mg/Kg. The compounds are dissolved in an appropriate vehicle (ETOH, DMSO or methylcellulose), administered in a solution if necessary. There are 3 animals per dose and they are observed post-administration for 4 hours again 6 hours later then twice daily for the duration of the study (1 week). If an animal exhibits obvious signs of distress (hunched posture, ruffled fur etc.), it is euthanized. The surviving mice are sacrificed day 7 post-administration and the critical organs are observed for evidence of drug toxicity. If abnormalities exist or there were other animals in the same group which did not survive to day 7, the tissues from the liver, heart, and kidneys are extracted and placed into 10% formalin solution. These fixed tissues are sectioned and examined for abnormalities resulting from drug toxicity. The MTD (mg/Kg) is the highest dose that results in no lethality/tissue abnormality.

EXAMPLE 13

Antiproliferative Screening Assay

A. Cancer Cell Line Screening

The activity of numerous compounds of the present invention against various cancer cell lines may be determined by submitting to the Developmental Therapeutics Program (DTP) at the National Cancer Institute (NCI) of the National Institutes of Health (NIH) for screening or by using methods known in the art.

The DTP Human Tumor Cell Line Screen utilizes 60 different human tumor cell lines, representing leukemia, melanoma and cancers of the lung, colon, brain, ovary, breast, prostate, and kidney according to conventional methods known in the art. See e.g. Alley, M. C., et al. (1988) Cancer Research 48:589-601; Grever, M. R., et al. (1992) Seminars in Oncology 19(6):622-638; and Boyd, M. R., and Paull, K. D. (1995) Drug Development Research 34:91-109, which are herein incorporated by reference.

Generally, the human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µl at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 hours prior to addition of the compounds to be tested.

After 24 hours, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 hours at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements (time zero, (Tz), control growth, (C), and test growth in the presence of drug at the five concentration levels (Ti)), the percentage growth is calculated at each of the drug concentrations levels. Percentage growth inhibition is calculated as:

((Ti-Tz)/(C-Tz))×100 for concentrations for which Ti>/=Tz ((Ti-Tz)/Tz)×100 for concentrations for which Ti<Tz.

Three dose response parameters are calculated for each experimental agent. Growth inhibition of 50% ($GI_{50}$) is calculated from ((Ti-Tz)/(C-Tz))×100=50, which is the drug concentration resulting in a 50% reduction in the net protein increase (as measured by SRB staining) in control cells during the drug incubation. The drug concentration resulting in total growth inhibition (TGI) is calculated from Ti=Tz. The $LC_{50}$ (concentration of drug resulting in a 50% reduction in the measured protein at the end of the drug treatment as compared to that at the beginning) indicating a net loss of cells following treatment is calculated from $((Ti-Tz)/Tz) \times 100 = -50$. Values are calculated for each of these three parameters if the level of activity is reached; however, if the effect is not reached or is exceeded, the value for that parameter is expressed as greater or less than the maximum or minimum concentration tested.

B. Hollow Fiber Assay

Generally, as a preliminary in vivo screening tool, the following assay is conducted. A standard panel of 12 tumor cell lines are used for the routine hollow fiber screening of the in vitro activities. These include NCI-H23, NCI-H522, MDA-MB-231, MDA-MB-435, SW-620, COLO 205, LOX, UACC-62, OVCAR-3, OVCAR-5, U251 and SF-295 according to conventional methods known in the art. See e.g. Hollingshead, M., et al. (1995) Life Sciences 57:131-141, which is herein incorporated by reference. The cell lines are cultivated in RPMI-1640 containing 10% FBS and 2 mM glutamine. On the day preceeding hollow fiber preparation, the cells are given a supplementation of fresh medium to maintain log phase growth. For fiber preparation, the cells are harvested by standard trypsinization technique and resuspended at the desired cell density ($(2-10 \times 10^6$ cells/ml). The cell suspension is flushed into 1 mm (internal diameter) polyvinylidene fluoride hollow fibers with a molecular weight exclusion of 500,000 Da. The hollow fibers are heat-sealed at 2 cm intervals and the samples generated from these seals are placed into tissue culture medium and incubated at 37° C. in 5% $CO_2$ for 24 to 48 hours prior to implantation. A total of 3 different tumor lines are prepared for each experiment so that each mouse receives 3 intraperitoneal implants (1 of each tumor line) and 3 subcutaneous implants (1 of each tumor line). On the day of implantation, samples of each tumor cell line preparation are quantitated for viable cell mass by a stable endpoint MTT assay so that the time zero cell mass is known. Mice are treated with experimental agents starting on day 3 or 4 following fiber implantation and continuing daily for 4 days. Each agent is administered by intraperitoneal injection at 2 dose levels. The fibers are collected from the mice on the day following the fourth compound treatment and subjected to the stable endpoint MTT assay. The optical density of each sample is determined spectrophotometrically at 540 nm and the mean of each treatment group is calculated. The percent net growth for each cell line in each treatment group is calculated and compared to the percent net growth in the vehicle treated controls.

A 50% or greater reduction in percent net growth in the treated samples compared to the vehicle control samples is considered a positive result. Each positive result is given a score of 2 and all of the scores are totaled for a given compound. The maximum possible score for an agent is 96 (12 cell lines×2 sites×2 dose levels×2 (score)). A compound is referred for xenograft testing if it has a combined IP+SC score of 20 or greater, a SC score of 8 or greater, or produces cell kill of any cell line at either dose level evaluated.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A tryptanthrin compound having the following structural formula (IV)

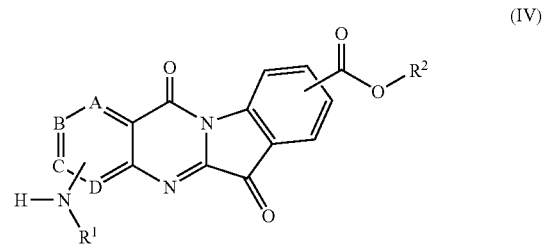

wherein A, B, C, and D are each independently selected from the group consisting of C, N, and S;

$R^1$ and $R^2$ are each independently selected from the group consisting of polyamines, polyethers and —L-$R^3$ wherein $R^3$ is substituted or unsubstituted

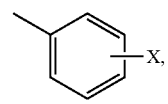

substituted or unsubstituted,

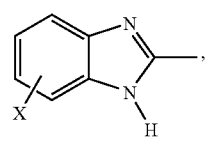

substituted or unsubstituted

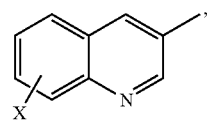

wherein X is one or more substituents selected from the group consisting of alkyl, hydroxyl, alkoxy, acyl, amino, alkylamino, dialkylamino, alkoxycarbonyl, carboxyl, carbamoyl, alkylaminocarboxyl, dialkylaminocarboxyl, alkylthio or mercapto and L is a linker selected from the group consisting of alkyl, alkylamino, dialkylamino, alkoxyl, alkoxycarbonyl, alkylaminocarbonyl, dialkylaminocarbonyl, alkylthio, and carbamoyl groups and wherein L contains about 2 to about 18 carbon, nitrogen, oxygen or sulfur atoms in its chain.

2. A pharmaceutical composition comprising the tryptanthrin compound of claim 1 and a pharmaceutically acceptable carrier.

3. The pharmaceutical composition of claim 2, wherein the tryptanthrin compound was dissolved a solvent selected from the group consisting of pyrrole, indole, pyridine, isoquinoline, nitrobenzene, aniline, N-methylbenzylamine, piperidine, pyrrolidine, phenol, benzyly alcohol, benzoic acid, and 1,4-dioxane then added to an aqueous solution, and then the solvent was evaporated.

4. The pharmaceutical composition of claim 3, wherein the solvent is pyrrole, indole, pyridine, isoquinoline, nitrobenzene, aniline, N-methylbenzylamine, piperidine, pyrrolidine, phenol, benzyly alcohol, benzoic acid, or 1,4-dioxane.

5. The pharmaceutical composition of claim 3, wherein the aqueous solution is deionized water.

6. A method of treating or inhibiting malaria, leishmaniasis, trypanosomiasis and tuberculosis in a subject which comprises administering to the subject a therapeutically effective amount of at least one tryptanthrin compound of claim 1.

7. A method of treating or inhibiting infection caused by Plasmodium, Leishmania, Trypanosoma or Mycobacterium in a subject which comprises administering to the subject a therapeutically effective amount of at least one tryptanthrin compound of claim 1.

* * * * *